United States Patent
Lee et al.

(10) Patent No.: US 9,653,690 B2
(45) Date of Patent: May 16, 2017

(54) ORGANIC COMPOUND, ORGANIC OPTOELECTRONIC DEVICE AND DISPLAY DEVICE

(71) Applicant: SAMSUNG SDI CO., LTD., Yongin-si, Gyeonggi-do (KR)

(72) Inventors: Han-Ill Lee, Suwon-si (KR); Eun-Sun Yu, Suwon-si (KR); Dong-Min Kang, Suwon-si (KR); Eui-Su Kang, Suwon-si (KR); Soo-Hyun Min, Suwon-si (KR); Yong-Tak Yang, Suwon-si (KR); Jae-Jin Oh, Suwon-si (KR); Dong-Kyu Ryu, Suwon-si (KR); Sang-Shin Lee, Suwon-si (KR); Yu-Na Jang, Suwon-si (KR); Soo-Young Jeong, Suwon-si (KR); Young-Kyoung Jo, Suwon-si (KR); Su-Jin Han, Suwon-si (KR); Jin-Seok Hong, Suwon-si (KR)

(73) Assignee: SAMSUNG SDI CO., LTD., Yongin-Si, Gyeonggi-Do (KR)

( * ) Notice: Subject to any disclaimer, the term of this patent is extended or adjusted under 35 U.S.C. 154(b) by 0 days.

(21) Appl. No.: 14/820,805

(22) Filed: Aug. 7, 2015

(65) Prior Publication Data

US 2015/0349270 A1  Dec. 3, 2015

Related U.S. Application Data

(63) Continuation-in-part of application No. PCT/KR2013/007166, filed on Aug. 8, 2013.

(30) Foreign Application Priority Data

Jun. 13, 2013 (KR) .......... 10-2013-0067929

(51) Int. Cl.
*H01L 51/00* (2006.01)
*C07D 409/04* (2006.01)
(Continued)

(52) U.S. Cl.
CPC ........ *H01L 51/0067* (2013.01); *C07D 307/77* (2013.01); *C07D 307/91* (2013.01);
(Continued)

(58) Field of Classification Search
CPC ............ H01L 51/0067; H01L 51/0073; H01L 51/0074; H01L 51/0052
See application file for complete search history.

(56) References Cited

U.S. PATENT DOCUMENTS 8,987,462 B2 * 3/2015 Kim ..................... H01L 51/006
546/276.7
2015/0144938 A1  5/2015 Lee et al.

FOREIGN PATENT DOCUMENTS

CN  102558121 A  7/2012
CN  104583202 A  4/2015
(Continued)

OTHER PUBLICATIONS

Jeon, et al., "Fluorenobenzofuran as the Core Structure of High Triplet Energy Host Materials for Green Phosphorescent Organic Light-Emitting Diodes", Journal of Materials Chemistry, vol. 22, No. 21, (2012), pp. 10537-10541.
(Continued)

*Primary Examiner* — Mamadou Diallo
(74) *Attorney, Agent, or Firm* — Lee & Morse, P.C.

(57) ABSTRACT

An organic compound represented by Chemical Formula 1, an organic optoelectric device including the organic compound, and a display device are disclosed.

17 Claims, 1 Drawing Sheet

(51) Int. Cl.
  *C07D 307/93*  (2006.01)
  *C07D 333/78*  (2006.01)
  *C07D 405/04*  (2006.01)
  *C09K 11/06*  (2006.01)
  *C07D 405/14*  (2006.01)
  *C07D 405/10*  (2006.01)
  *C07D 407/04*  (2006.01)
  *C07D 409/10*  (2006.01)
  *C07D 409/14*  (2006.01)
  *C07D 307/77*  (2006.01)
  *C07D 307/91*  (2006.01)
  *H01L 51/50*  (2006.01)

(52) U.S. Cl.
  CPC ......... *C07D 307/93* (2013.01); *C07D 333/78* (2013.01); *C07D 405/04* (2013.01); *C07D 405/10* (2013.01); *C07D 405/14* (2013.01); *C07D 407/04* (2013.01); *C07D 409/04* (2013.01); *C07D 409/10* (2013.01); *C07D 409/14* (2013.01); *C09K 11/06* (2013.01); *H01L 51/0052* (2013.01); *H01L 51/0072* (2013.01); *H01L 51/0073* (2013.01); *H01L 51/0074* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

FOREIGN PATENT DOCUMENTS

| | | | |
|---|---|---|---|
| CN | 104903421 A | 9/2015 | |
| EP | 2 889 296 A1 | 7/2015 | |
| JP | 2010-045281 A | 2/2010 | |
| JP | 2011-148780 A | 8/2011 | |
| JP | 2012-028548 A | 2/2012 | |
| JP | 2012-107005 A | 6/2012 | |
| JP | 5357150 B2 | 12/2013 | |
| JP | 2015-534258 A | 11/2015 | |
| KR | 10-2009-0086057 A | 8/2009 | |
| KR | 10-2011-0073326 A | 6/2011 | |
| KR | 10-2011-0097784 A | 8/2011 | |
| KR | 10-2011-0122129 A | 11/2011 | |
| KR | 10-2012-0029751 A | 3/2012 | |
| KR | 10-2012-0047706 A | 5/2012 | |
| KR | 10-2012-0049135 A | 5/2012 | |
| KR | EP 2450975 A2 * | 5/2012 | ......... H01L 51/0061 |
| KR | 10-2012-0078301 A | 7/2012 | |
| KR | 10-2013-0011955 A | 1/2013 | |
| KR | 10-2013-0018725 A | 2/2013 | |
| KR | 10-2014-0049186 A | 4/2014 | |
| WO | WO 2010-061824 A1 | 6/2010 | |
| WO | WO 2011/057701 A1 | 5/2011 | |
| WO | WO 2011-122132 A1 | 10/2011 | |
| WO | WO 2013/012298 A1 | 1/2013 | |
| WO | WO 2013-081416 A1 | 6/2013 | |
| WO | WO 2014-034584 A1 | 3/2014 | |
| WO | WO 2014/061963 A1 | 4/2014 | |
| WO | WO 2014-104514 A1 | 7/2014 | |

OTHER PUBLICATIONS

Chinese Search Report dated Jul. 25, 2016 in Corresponding Chinese Patent Application No. 201380075021.3.

Extended European Search Report dated Aug. 9, 2016 in Corresponding European Patent Application No. 13886879.9.

* cited by examiner

ORGANIC COMPOUND, ORGANIC OPTOELECTRONIC DEVICE AND DISPLAY DEVICE

CROSS-REFERENCE TO RELATED APPLICATION

This application is a continuation-in-part of pending International Application No. PCT/KR2013/007166, entitled "Organic Compound, Organic Optoelectronic Device and Display Device," which was filed on Aug. 8, 2013, the entire contents of which are hereby incorporated by reference.

Korean Patent Application No. 10-2013-0067929, filed on Jun. 13, 2013, in the Korean Intellectual Property Office, and entitled: "Organic Compound, Organic Optoelectronic Device and Display Device," is incorporated by reference herein in its entirety.

BACKGROUND

1. Field

An organic compound, an organic optoelectric device, and a display device are disclosed.

2. Description of the Related Art

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectric device may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an anode and a cathode. Herein, an organic layer may include an emission layer and optionally an auxiliary layer, and the auxiliary layer may include, for example at least one selected from a hole injection layer, a hole transport layer, an electron blocking layer, an electron transport layer, an electron injection layer and a hole blocking layer in order increase efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY

Embodiments are directed to CLAIM LANGUAGE TO BE ADDED

One embodiment provides an organic compound capable of realizing an organic optoelectric device having high efficiency and long life-span.

Another embodiment provides an organic optoelectric device including the organic compound.

Yet embodiment provides a display device including the organic optoelectric device.

According to one embodiment, an organic compound represented by the Chemical Formula 1 is provided:

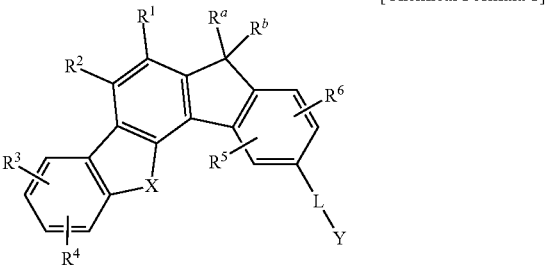

[Chemical Formula 1]

In Chemical Formula 1,

X is O, S, Se, SO, $SO_2$, PO, or CO,

Y is a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, or a combination thereof, L is a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, a substituted or unsubstituted C3 to C30 heteroarylene group, a substituted or unsubstituted C6 to C30 aryleneamine group, a substituted or unsubstituted C6 to C30 heteroaryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, $R^a$ and $R^b$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof, $R^1$ to $R^6$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof.

According to another embodiment, provided an organic optoelectric device including an anode and a cathode facing each other, at least one organic layer between the anode and the cathode, wherein the organic layer includes the organic compound.

According to yet another embodiment, a display device including the organic optoelectric device is provided.

An organic optoelectric device having high efficiency long life-span may be realized.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
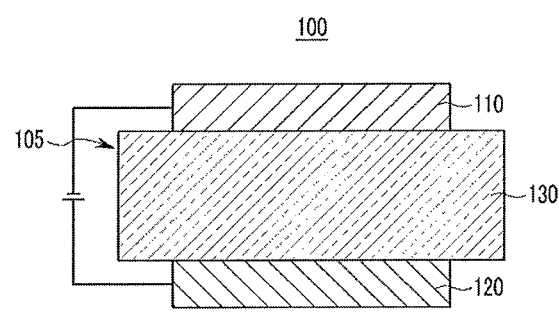
FIGS. 1 and 2 illustrate cross-sectional views showing organic light emitting diodes according to one embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted a halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as a trifluoromethyl group, or cyano group may be fused to each other to form a ring. For example, the substituted C6 to C30 aryl group may be fused with another adjacent substituted C6 to C30 aryl group to provide a substituted or unsubstituted fluorene ring.

In the present specification, when specific definition is not otherwise provided, "hetero" refers to one including 1 to 3 hetero atoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, the term "heteroaryl group" refers to an aryl group including at least one heteroatoms selected from N, O, S, P, and Si, and remaining carbons. When the heteroaryl group is a fused ring, the entire ring or each ring of the heteroaryl group may include 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof, but are not limited thereto.

In the specification, hole characteristics refer to characteristics capable of donating an electron when an electric field is applied and that a hole formed in the anode is easily injected into the emission layer and transported in the emission layer due to conductive characteristics according to highest occupied molecular orbital (HOMO) level.

In addition, electron characteristics refer to characteristics capable of accepting an electron when an electric field is applied and that an electron formed in the cathode is easily injected into the emission layer and transported in the emission layer due to conductive characteristics according to lowest unoccupied molecular orbital (LUMO) level.

Hereinafter, an organic compound according to one embodiment is described.

An organic compound according to one embodiment is represented by Chemical Formula 1.

[Chemical Formula 1]

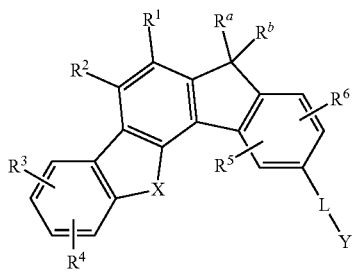

In Chemical Formula 1,

X is O, S, Se, SO, $SO_2$, PO, or CO,

Y is a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, or a combination thereof, L is a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, a substituted or unsubstituted C3 to C30 heteroarylene group, a substituted or unsubstituted C6 to C30 aryleneamine group, a substituted or unsubstituted C6 to C30 heteroaryleneamine group, a substituted or unsubstituted C to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, $R^a$ and $R^b$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof, and $R^1$ to $R^6$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof.

In Chemical Formula 1, Y is a functional group having hole characteristics or electron characteristics, and may be, for example selected from substituted or unsubstituted functional groups listed in Group 1.

[Group 1]

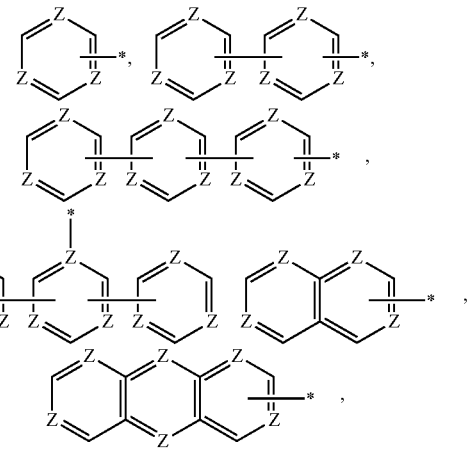

-continued

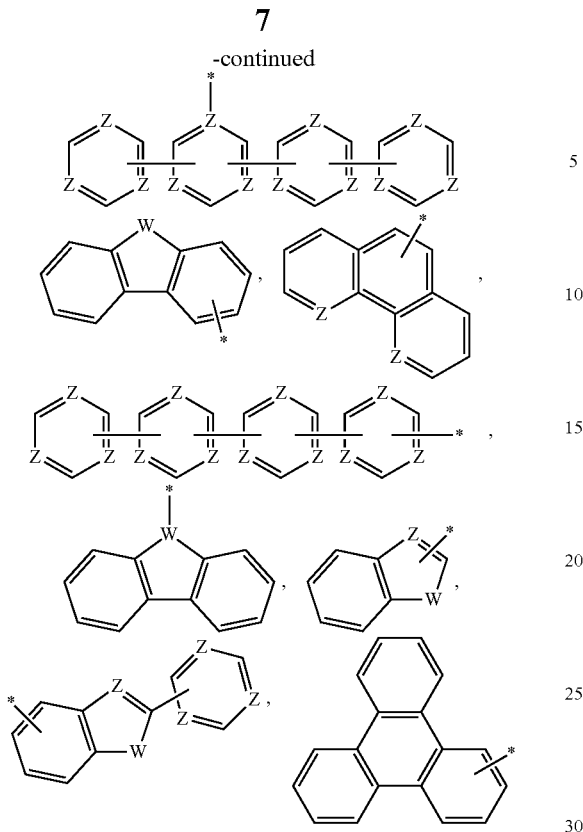

In Group 1,

W is N, O, S, SO, SO$_2$, CR$^c$, CR$^d$R$^e$, SiR$^f$, or SiR$^g$R$^h$,

Z is N, C or CR$^i$, wherein R$^c$ to R$^i$ are each independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and

* is a linking point, and may be positioned at one of elements consisting of the functional group.

The Y may be, for example an aryl group or a heteroaryl group of a substituted or unsubstituted one ring, and may be, for example represented by one of Chemical Formulae A1 to A8.

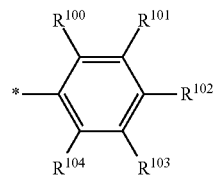
[Chemical Formula A1]

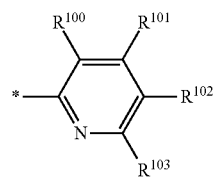
[Chemical Formula A2]

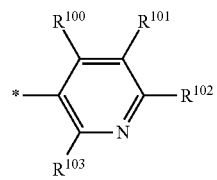
[Chemical Formula A3]

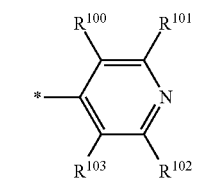
[Chemical Formula A4]

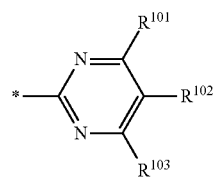
[Chemical Formula A5]

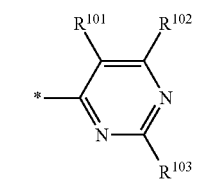
[Chemical Formula A6]

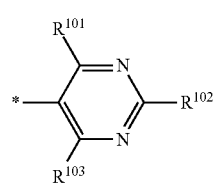
[Chemical Formula A7]

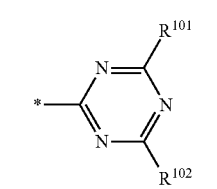
[Chemical Formula A8]

In Chemical Formulae A1 to A8, $R^{100}$ to $R^{104}$ are each independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and * is a linking point.

The Y may be, for example an aryl group and/or a heteroaryl group of a substituted or unsubstituted two rings, and may be, for example represented by one of Chemical Formulae A9 to A22.

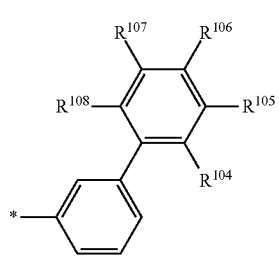
[Chemical Formula A9]

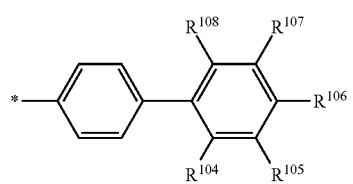
[Chemical Formula A10]

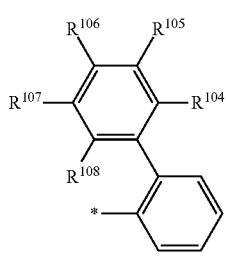
[Chemical Formula A11]

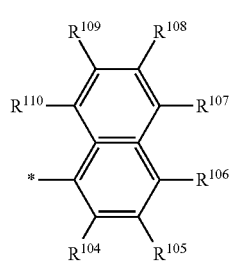
[Chemical Formula A12]

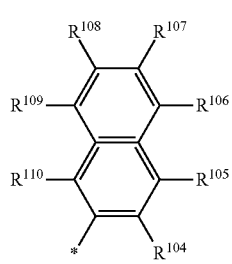
[Chemical Formula A13]

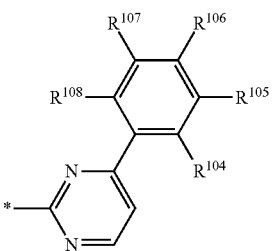
[Chemical Formula A14]

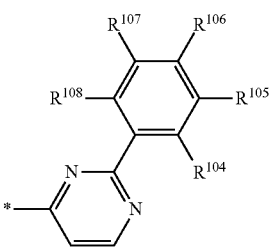
[Chemical Formula A15]

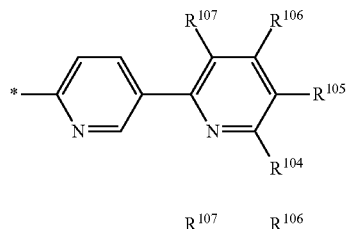
[Chemical Formula A16]

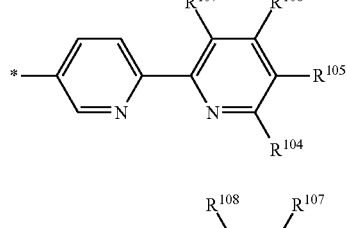
[Chemical Formula A17]

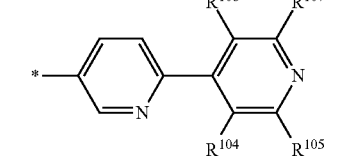
[Chemical Formula A18]

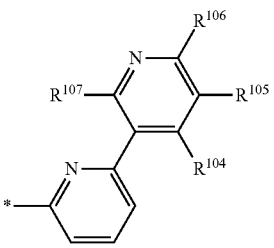
[Chemical Formula A19]

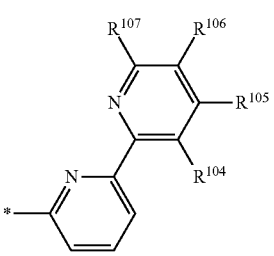
[Chemical Formula A20]

-continued

[Chemical Formula A21]

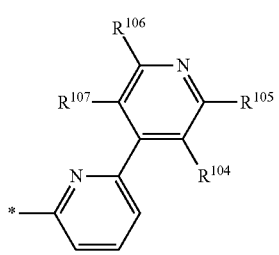

[Chemical Formula A22]

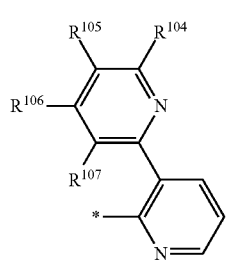

In Chemical Formulae A9 to A22, $R^{104}$ to $R^{108}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and * is a linking point.

The Y may be, for example an aryl group and/or a heteroaryl group of a substituted or unsubstituted three ring, and may be, for example represented by one of Chemical Formulae A23 to A32.

[Chemical Formula A23]

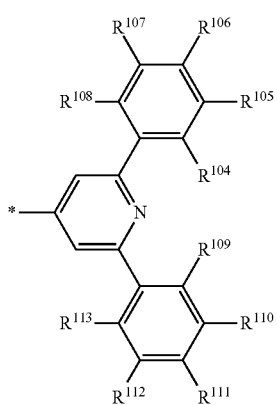

[Chemical Formula A24]

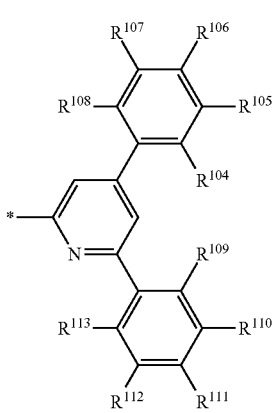

[Chemical Formula A25]

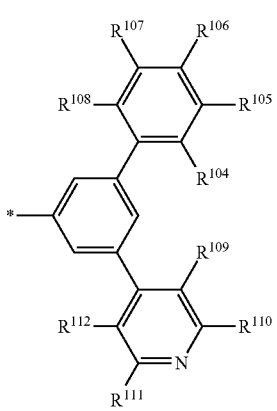

[Chemical Formula A26]

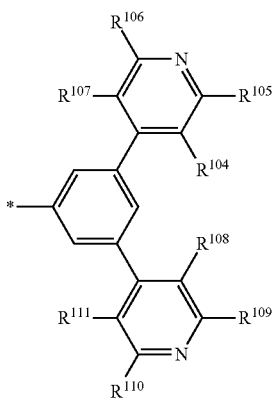

[Chemical Formula A27]

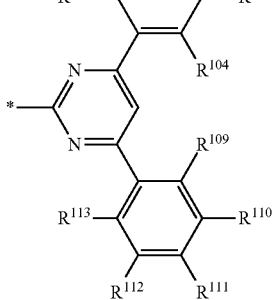

[Chemical Formula A28]
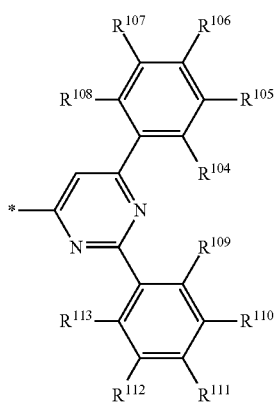

[Chemical Formula A29]
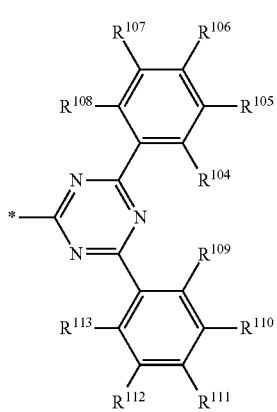

[Chemical Formula A30]
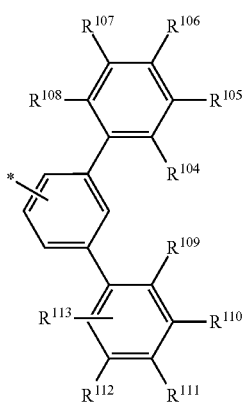

[Chemical Formula A31]
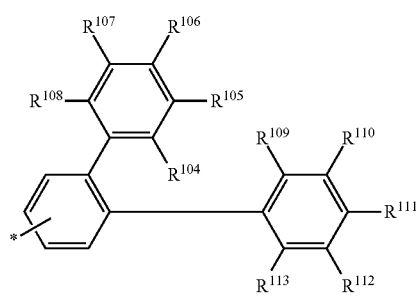

[Chemical Formula A32]
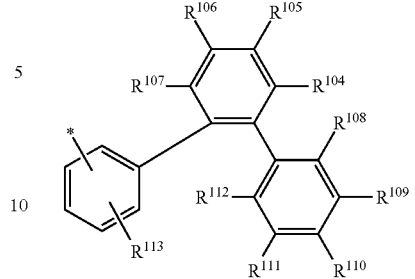

In Chemical Formulae A23 to A32, $R^{104}$ to $R^{113}$ are independently hydrogen, deuterium, a substituted or unsubstituted C1 to C30 alkyl group, a substituted or unsubstituted C6 to C30 aryl group, * is a linking point.

The Y may be, for example an aryl group and/or a heteroaryl group of a substituted or unsubstituted four ring, and may be, for example represented by one of Chemical Formulae A33 to A35.

[Chemical Formula A33]
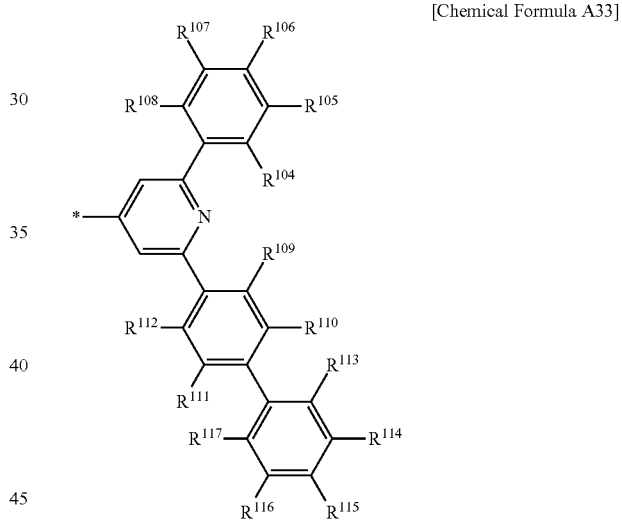

[Chemical Formula A34]
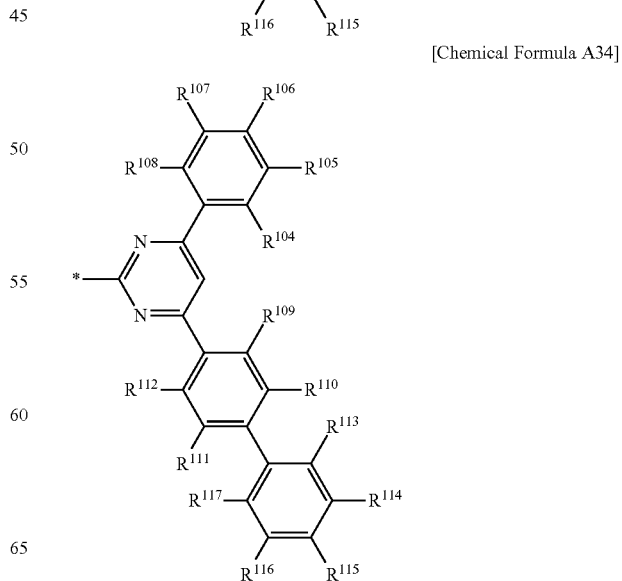

-continued

[Chemical Formula A35]

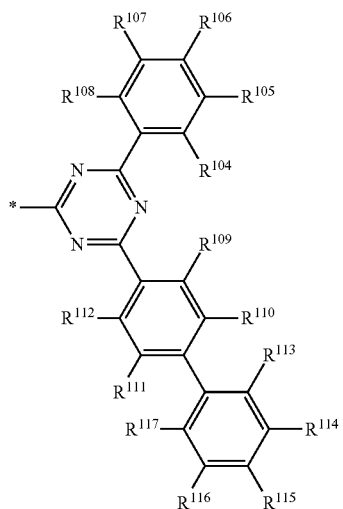

[Chemical Formula A39]

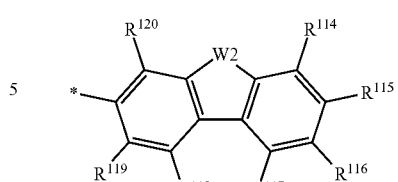

In Chemical Formulae A33 to A35, $R^{104}$ to $R^{117}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and * is a linking point.

The Y may be, for example an aryl group and/or a heteroaryl group of a substituted or unsubstituted fused ring, and may be, for example represented by one of Chemical Formulae A36 to A41.

[Chemical Formula A36]

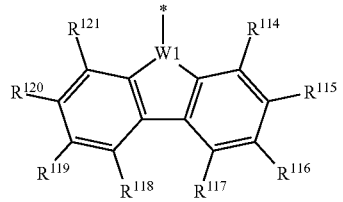

[Chemical Formula A37]

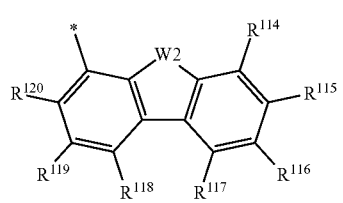

[Chemical Formula A38]

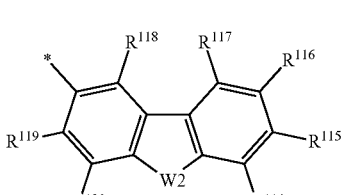

[Chemical Formula A40]

[Chemical Formula A41]

In Chemical Formulae A36 to A41,

W1 is N, $CR^c$ or $SiR^f$,

W2 is O, S, SO, $SO_2$, $CR^dR^e$, or $SiR^gR^h$,

Ar is a substituted or unsubstituted C6 to C30 arylene group, a substituted or unsubstituted C3 to C30 heteroarylene group, a substituted or unsubstituted C6 to C30 aryleneamine group, a substituted or unsubstituted C6 to C30 heteroaryleneamine group, a substituted or unsubstituted C1 to C30 aryloxylene group, or a combination thereof, $R^{114}$ to $R^2$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and

* is a linking point.

The Y may be, for example an aryl group and/or a heteroaryl group of a substituted or unsubstituted fused ring, and may be, for example represented by one of Chemical Formulae A42 to A50.

[Chemical Formula A42]

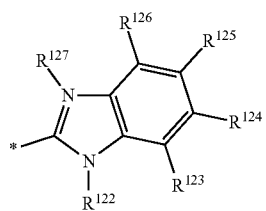

[Chemical Formula A43]

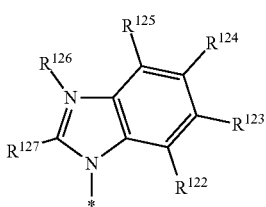

[Chemical Formula A44]

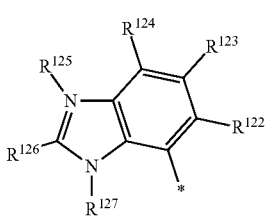

[Chemical Formula A45]

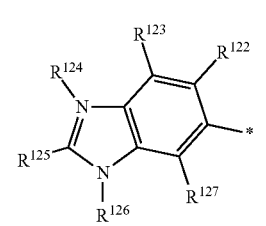

[Chemical Formula A46]

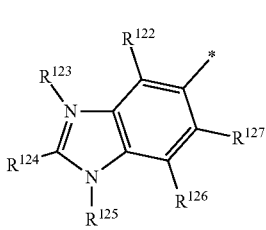

[Chemical Formula A47]

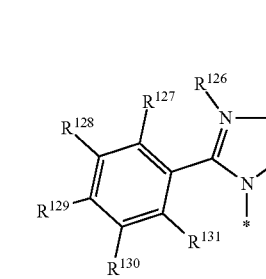

[Chemical Formula A48]

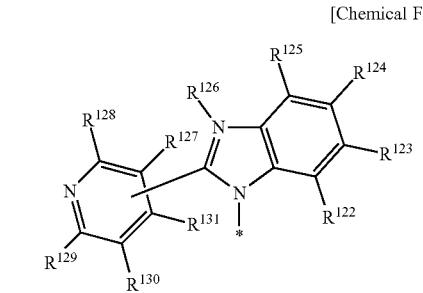

[Chemical Formula A49]

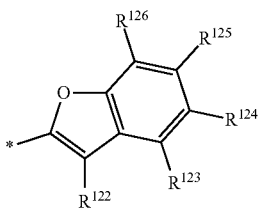

[Chemical Formula A50]

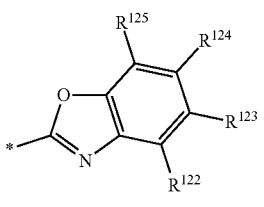

In Chemical Formulae A42 to A50, $R^{122}$ to $R^{131}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and * is a linking point.

For example, in Chemical Formula 1, the Y may be an organic compound of a substituted or unsubstituted pyridinyl group, a substituted or unsubstituted pyrimidinyl group, a substituted or unsubstituted triazinyl group, a substituted or unsubstituted phenyl group, a substituted or unsubstituted biphenyl group, a substituted or unsubstituted naphthyl group, a substituted or unsubstituted triphenyl group, a substituted or unsubstituted dibenzofuranyl group, a substituted or unsubstituted dibenzothiophenyl group, a substituted or unsubstituted fluorenyl group, a substituted or unsubstituted benzopyridinyl group, a substituted or unsubstituted benzoimidazolyl group, or a substituted or unsubstituted benzofuranyl group. In Chemical Formula 1, L may be a single bond, or a substituted or unsubstituted phenyl group, or a substituted or unsubstituted biphenyl group.

For example, in Chemical Formula 1, $R^a$ and $R^b$ may be independently a methyl group or a substituted or unsubstituted phenyl group.

For example, in Chemical Formula 1, $R^3$ and $R^4$ may be independently hydrogen or a substituted or unsubstituted phenyl group.

The organic compound represented by Chemical Formula 1 has a structure that a fused ring is bonded with the functional group represented by Y and having hole characteristics or electron characteristics directly or through a linking group L.

The organic compound represented by Chemical Formula 1 may appropriately control a charge flow in itself, since the functional group represented by Y and having hole characteristics or electron characteristics is bonded at a particular position of the fused ring. Accordingly, the organic compound may be applied to an organic optoelectric device and thus, lower driving voltage of the organic optoelectric device and improve luminous efficiency and life-span characteristics of the organic optoelectric device In addition, the organic compound may appropriately control a charge flow and thus, reduce resonance in the organic compound and thereby, increase triplet energy TI. Accordingly, the organic compound may improve efficiency of an organic optoelectric device, when applied to the organic optoelectric device. In addition, the triplet energy TI may be in an appropriate range enough to be used, for example, as a phosphorescent host and specifically in a range of about 3.1 to 2.5 eV.

The functional group having hole characteristics or electron characteristics represented by Y may be directly linked to the fused ring, wherein the linking group L may be a single bond.

The functional group having hole characteristics or electron characteristics represented by Y may be linked through a linking group L. The linking group L may be, for example a substituted or unsubstituted C6 to C30 arylene group, a substituted or unsubstituted C3 to C30 heteroarylene group, or a combination thereof, and may have, for example a kink structure in the center of the arylene group and/or heteroarylene group.

The kink structure indicates a structure that two linking points of an arylene group and/or a heteroarylene group are not linearly linked. For example, as for phenylene, ortho phenylene (o-phenylene) and meta phenylene (m-phenylene) have a kink structure that the phenylene has no linear structure at its linking points, while para phenylene (p-phenylene) does not have a kink structure that the phenylene has a linear structure at its linking points.

In this way, the linking group L has the kink structure and thus, may further effectively control a charge flow in the organic compound.

The linking group L may be, for example selected from substituted or unsubstituted linking groups L listed in Group 2.

[Group 2]

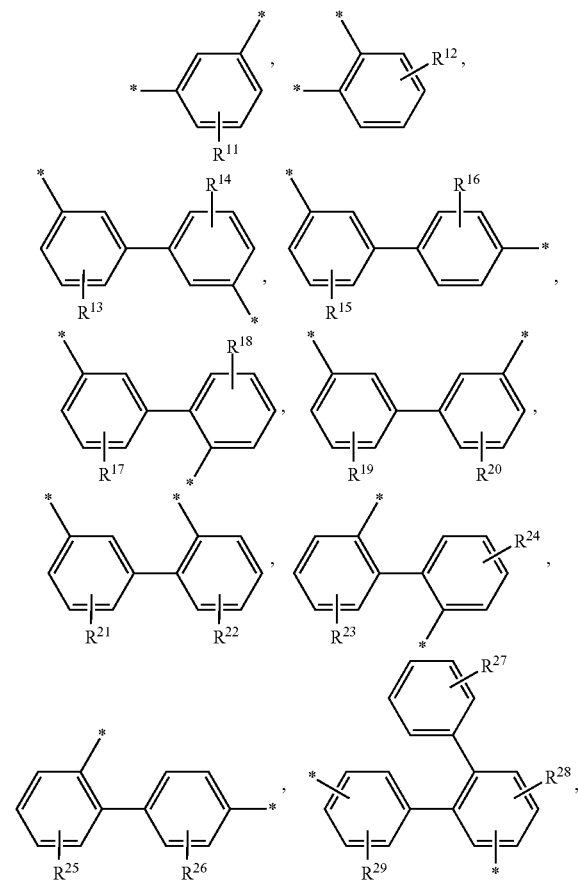

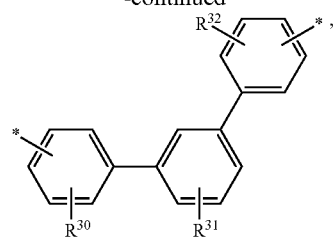

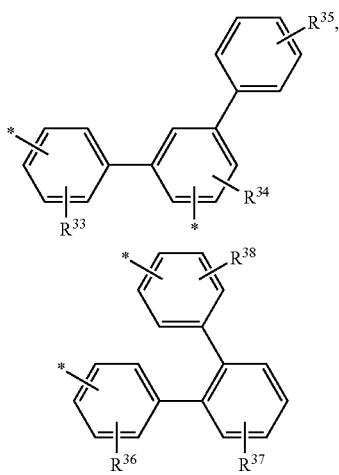

the $R^{11}$ to $R^{38}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof, and

* is a linking point.

The organic compound may have, for example a molecular weight of about 400 to 800. The organic compound having a molecular weight within the range may allow a deposit process to be performed at a relatively low temperature, lower a process temperature and thus, improve processibility.

The organic compound represented by Chemical Formula 1 has various functional groups and/or substituents and thus, may be designed to have desired characteristics. For example, when the Y in the above Chemical Formula 1 is a functional group having hole characteristics, the organic compound may be designed to have strong hole characteristics, but when the Y in the above Chemical Formula 1 is a functional group having electron characteristics, the organic compound includes both of moieties having electron characteristics and hole characteristics and thus, may be designed to have bipolar characteristics.

The organic compound may be, for example compounds listed in the following Group 3, but is not limited thereto.

[Group 3]
1
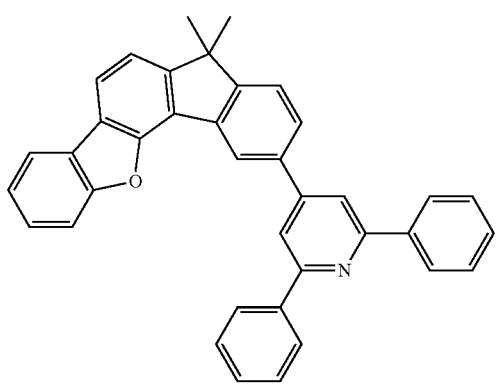
2
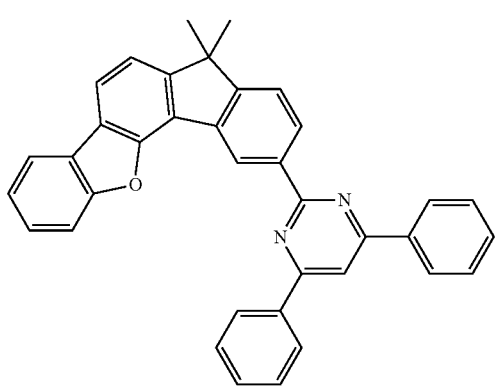
3
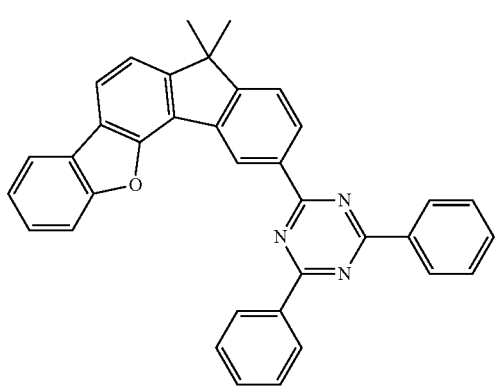
4
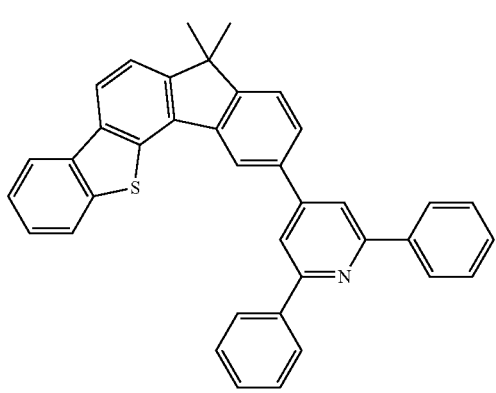
5
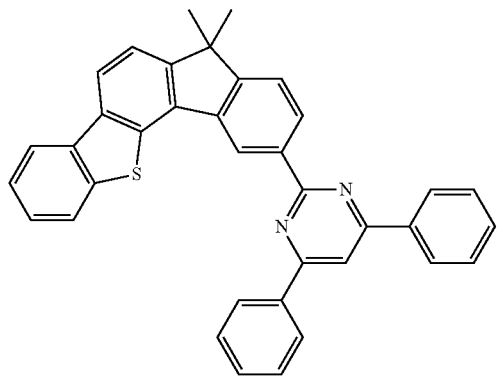
6
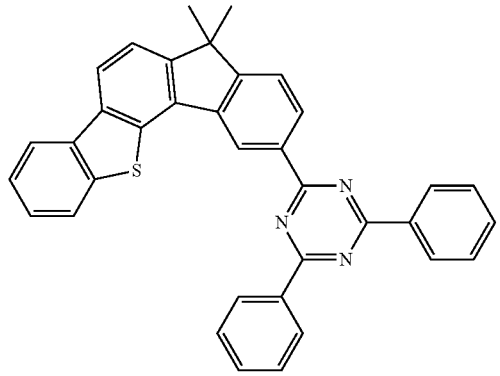
7
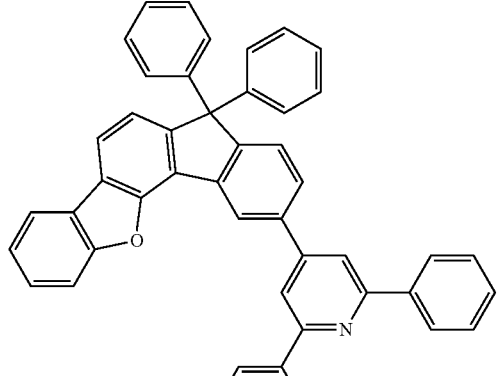
8
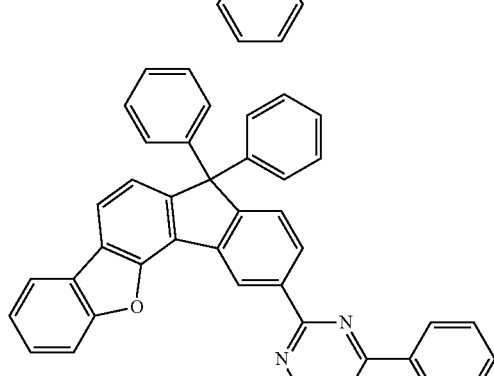

9
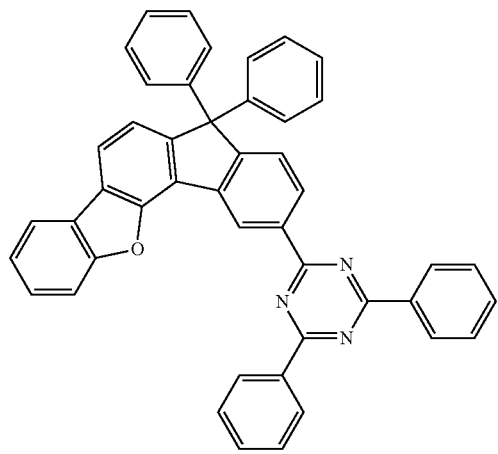
10
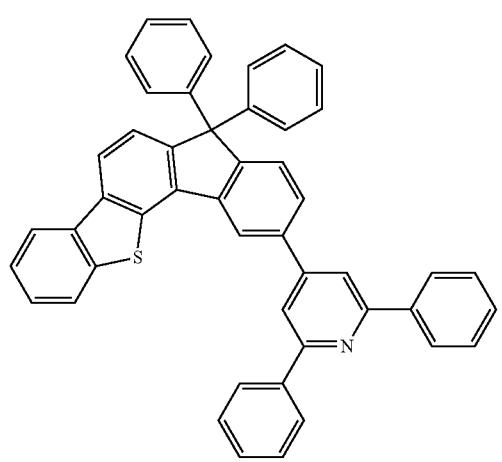
11
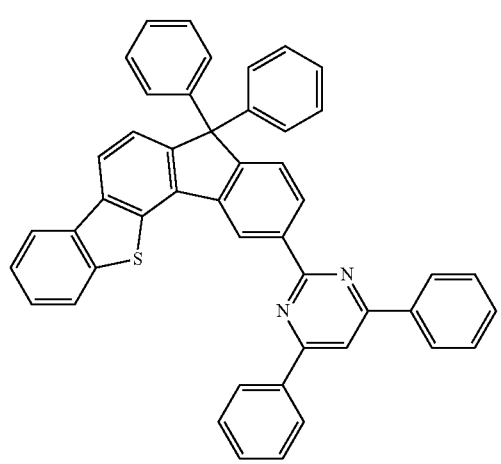
12
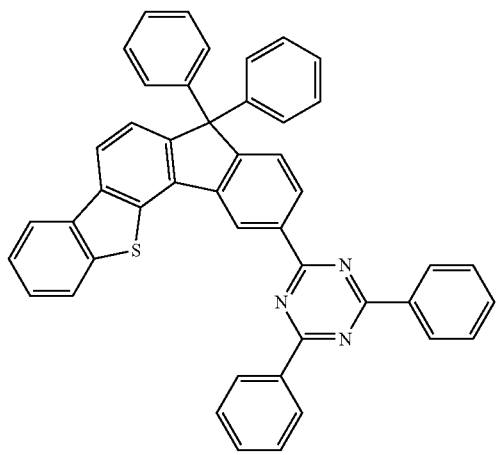
13
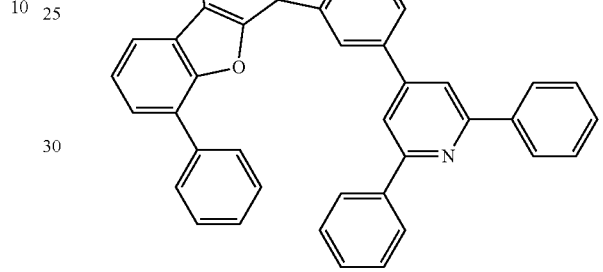
14
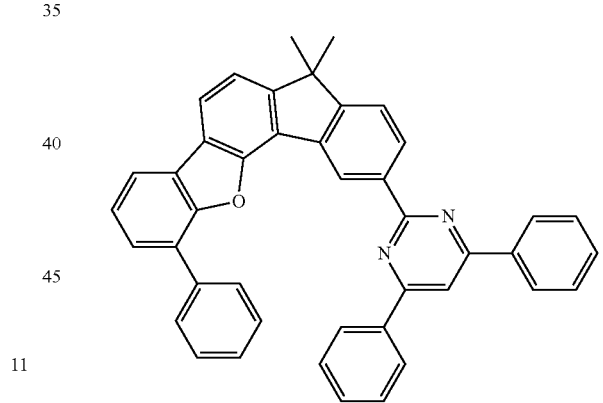
15

16
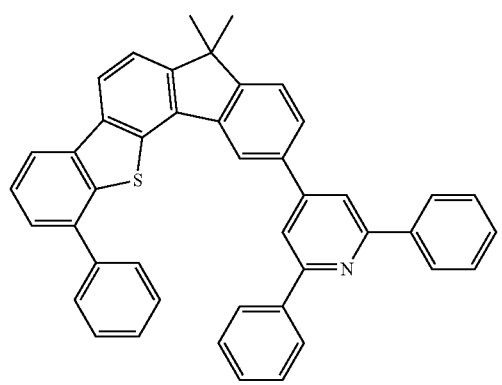
17
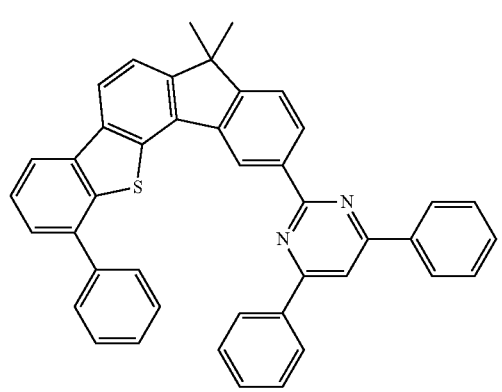
18
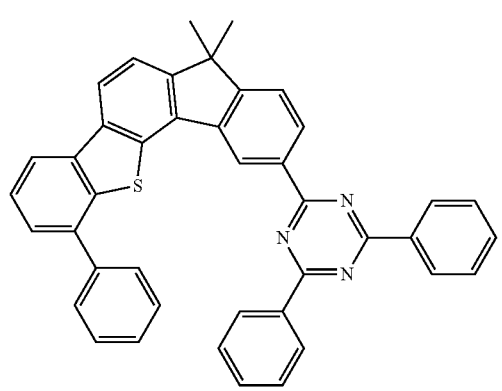
19
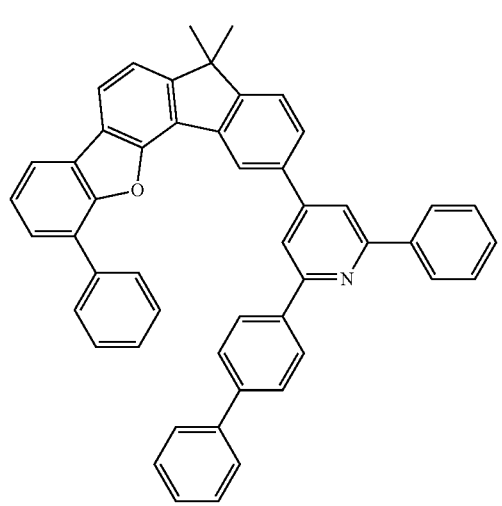
20
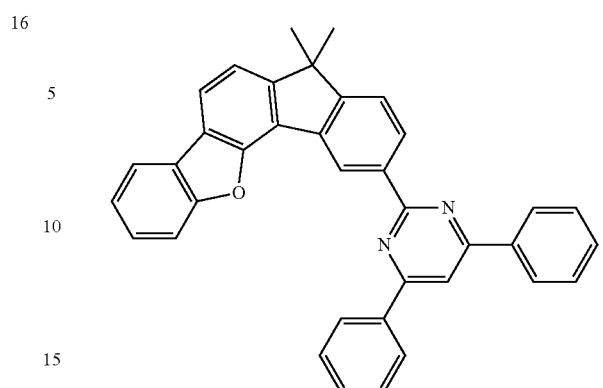
21
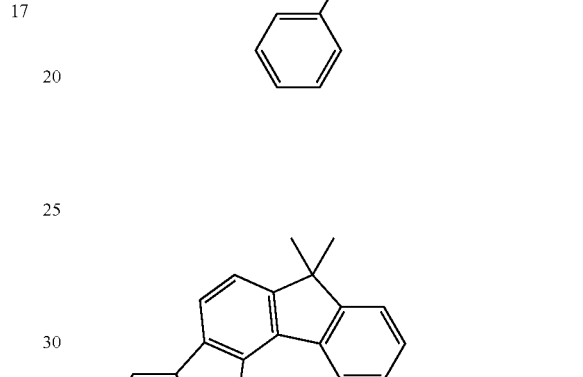
22
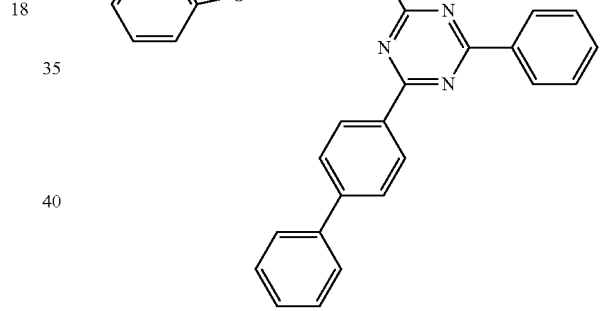
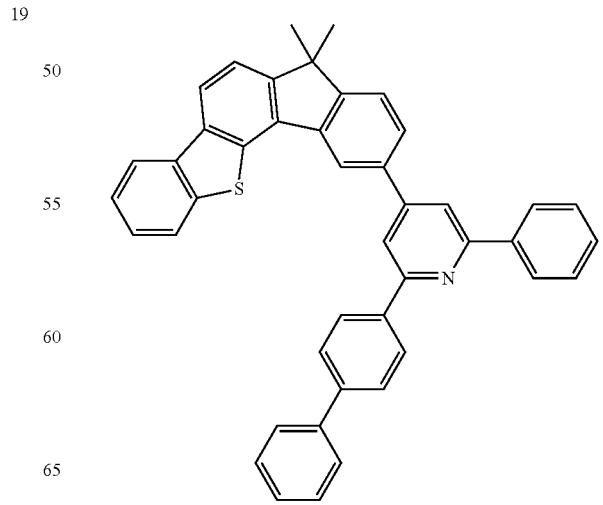

23
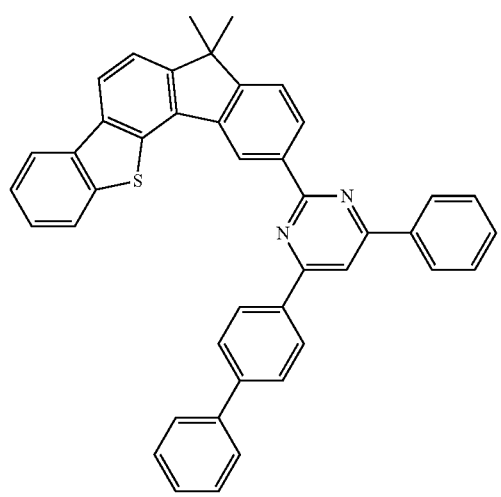
24
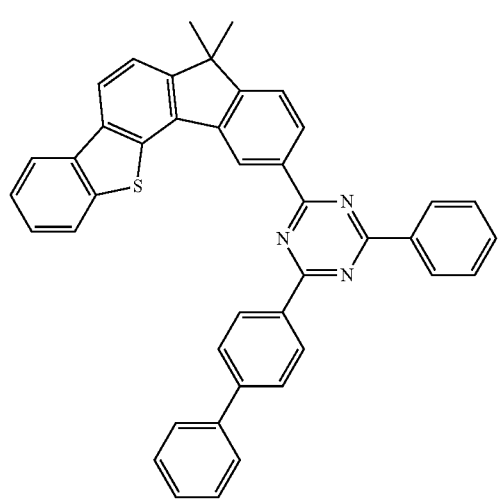
25
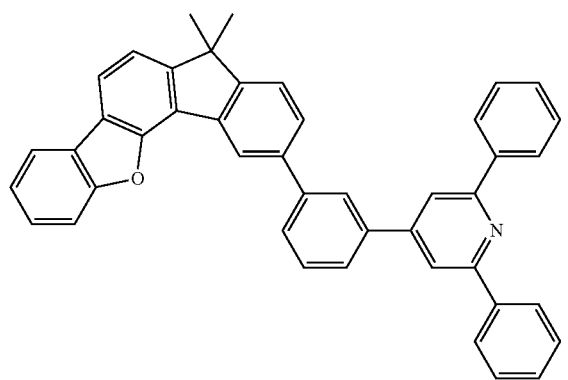
26
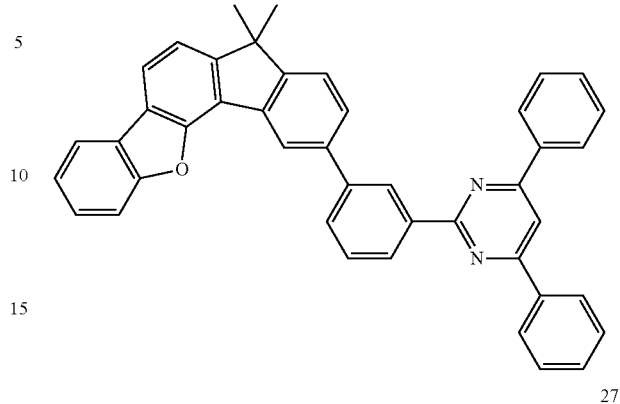
27
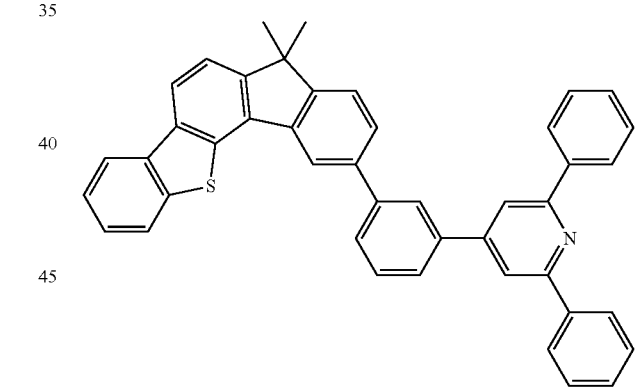
28
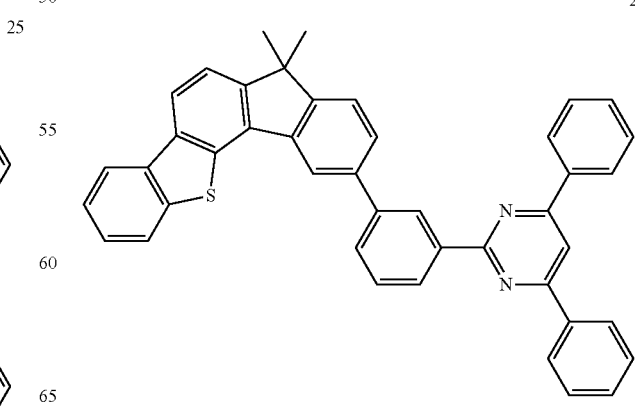
29

30
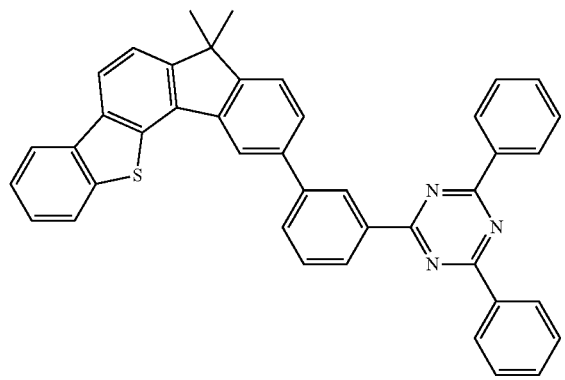
31
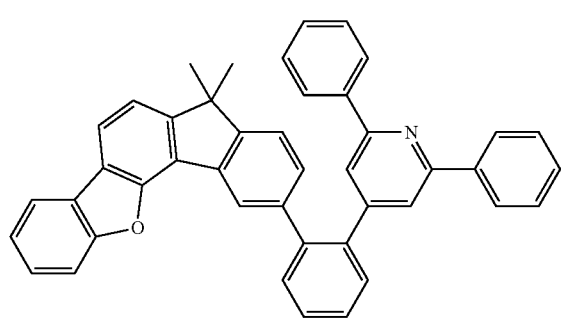
32
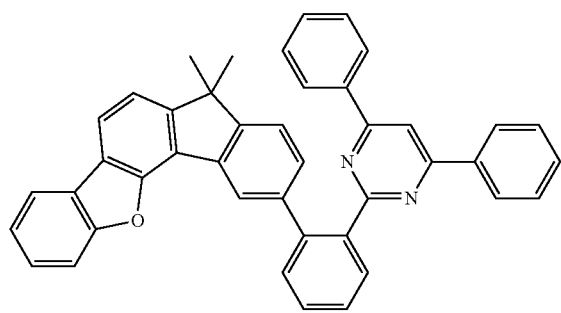
33
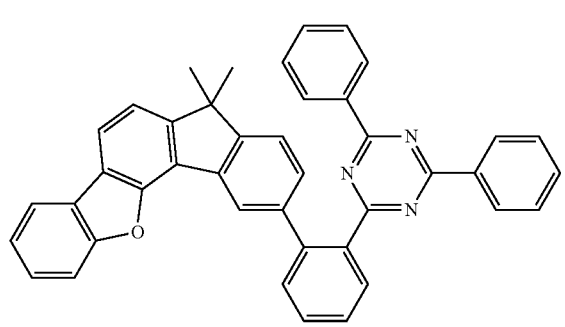
34
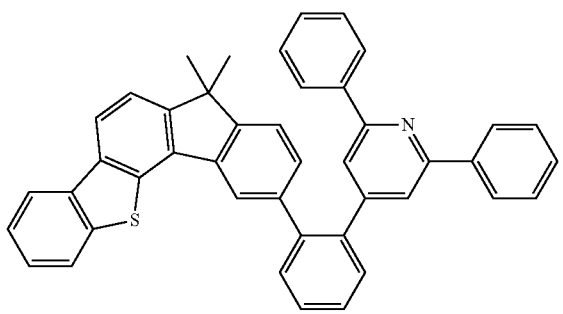
35
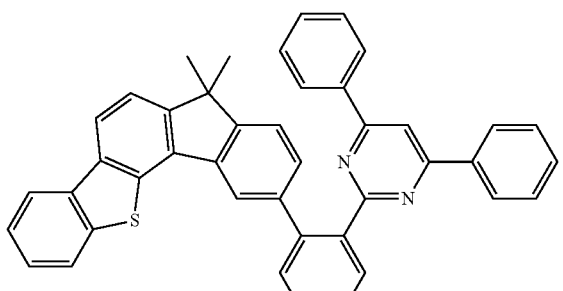
36
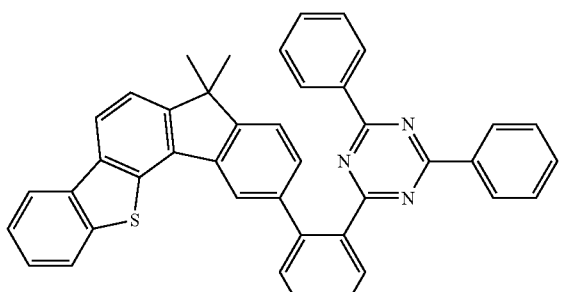
37
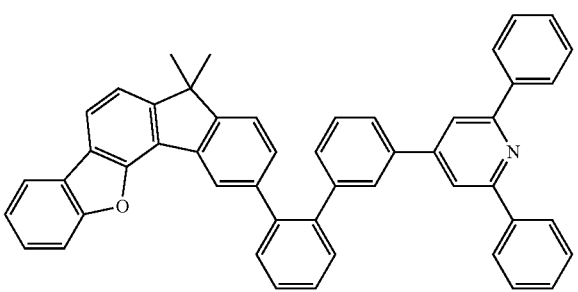
38
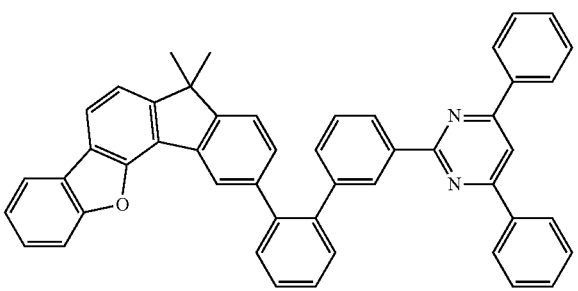

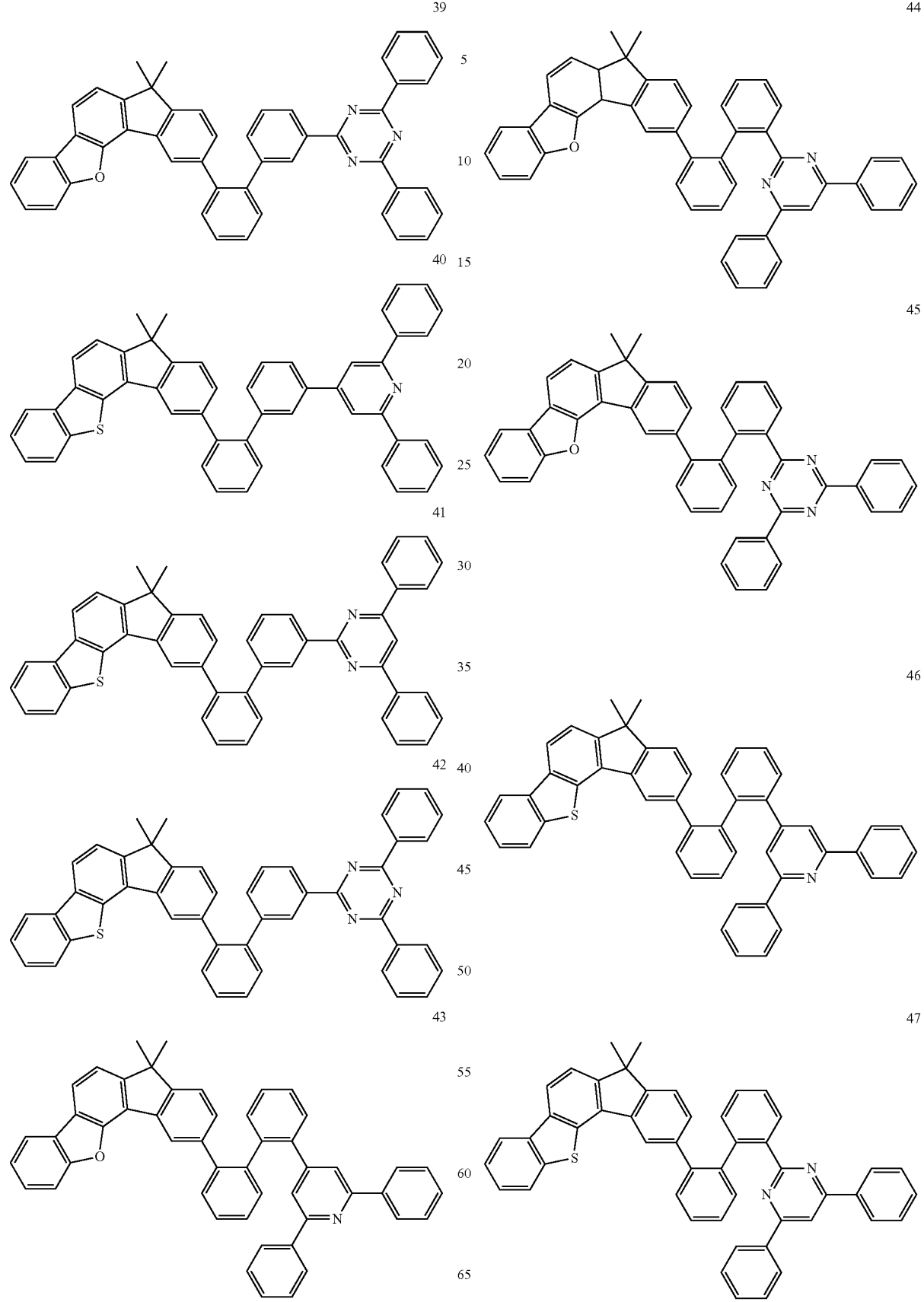

48
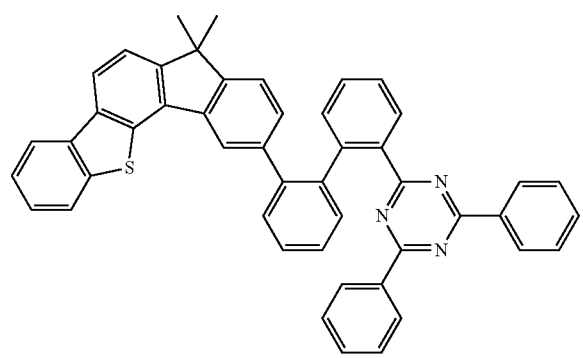
49
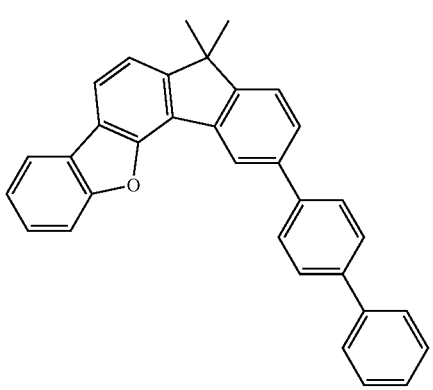
50
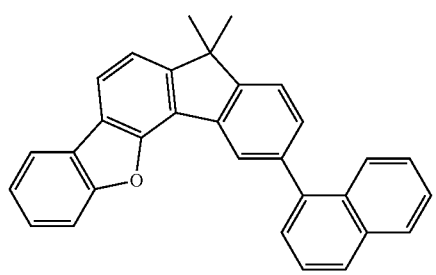
51
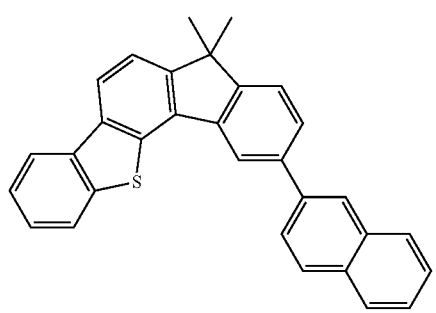
53
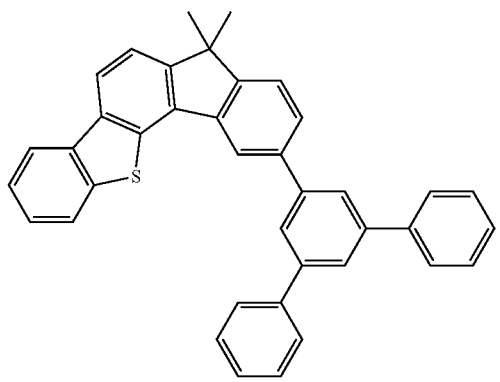
54
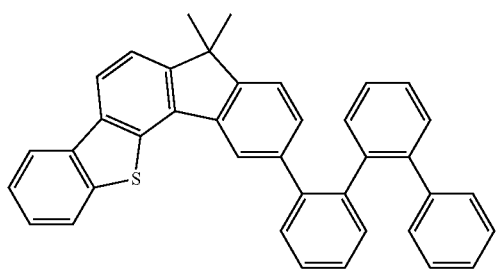
55
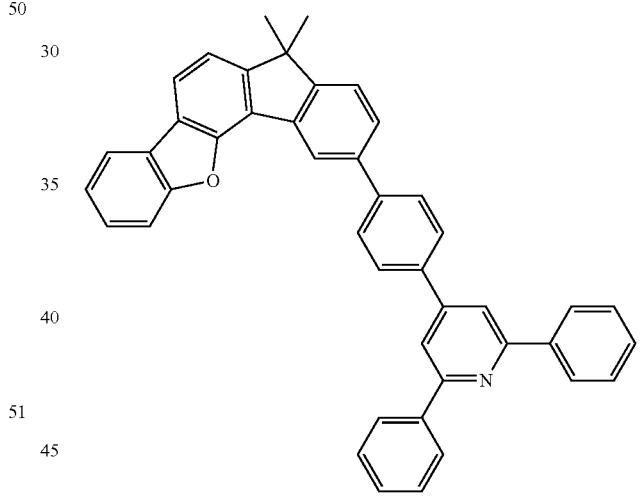
56
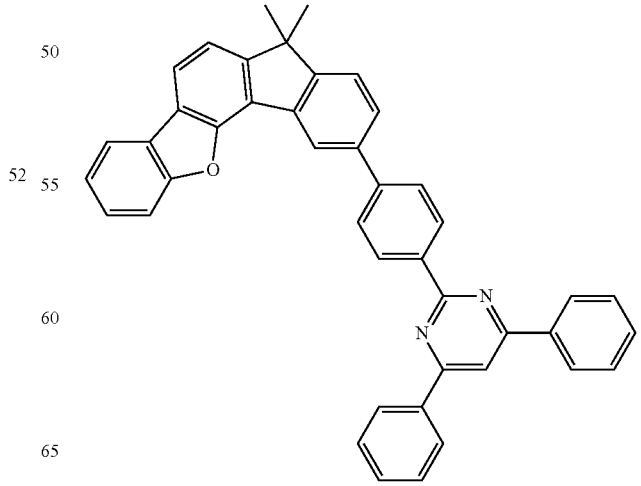

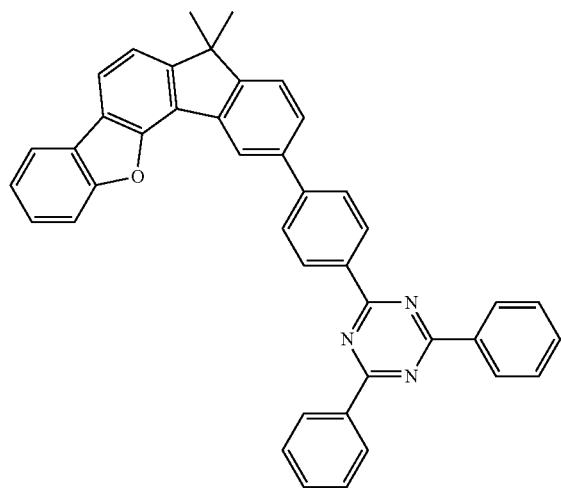
57
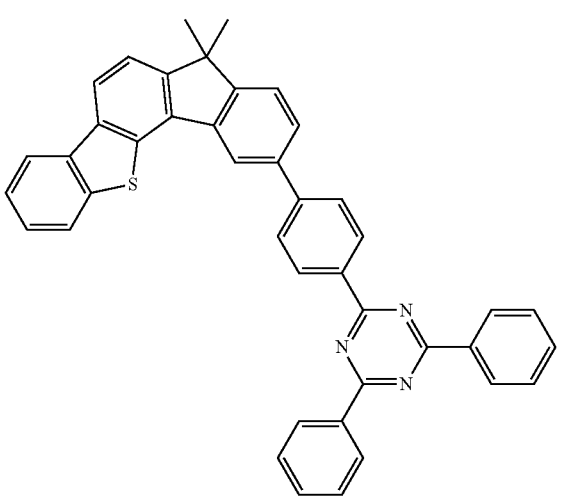
60
58
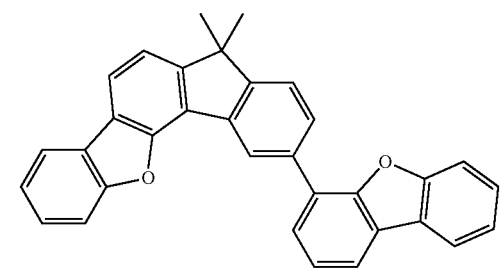
61
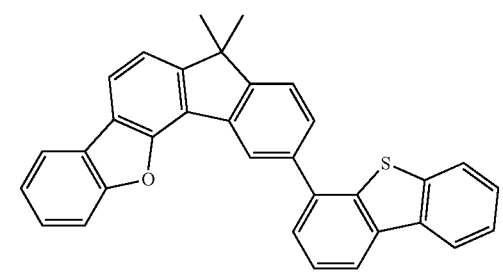
62
59
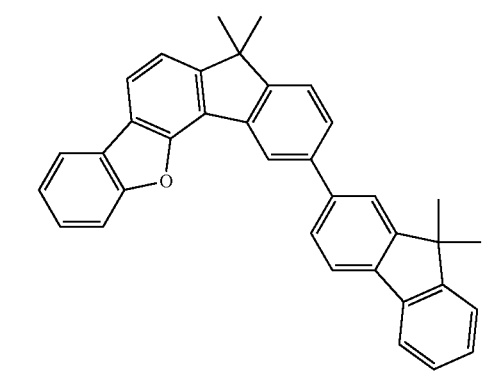
63

64
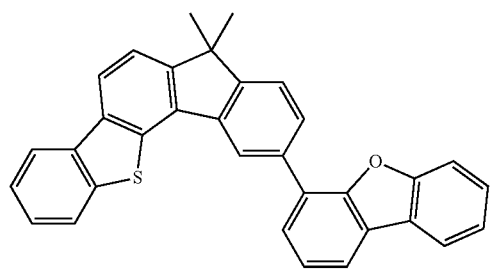
65
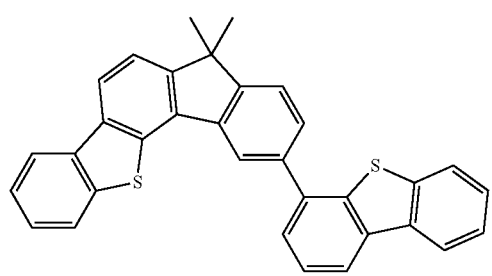
66
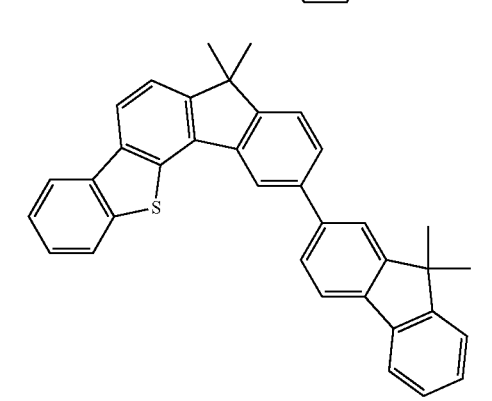
67
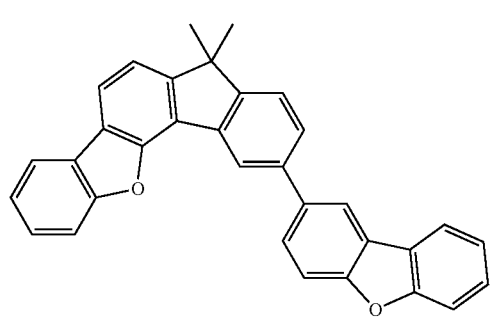
68
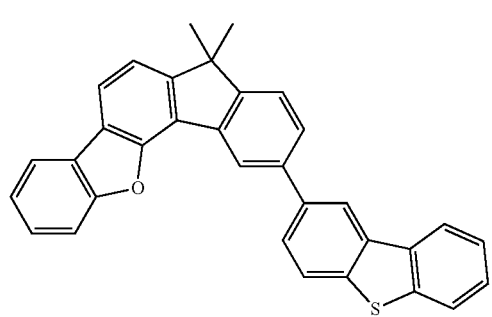
69
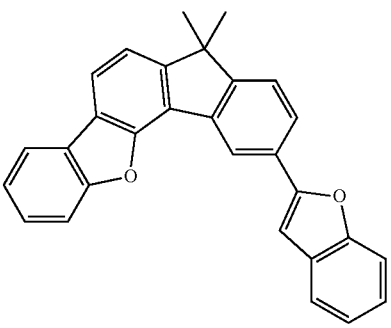
70
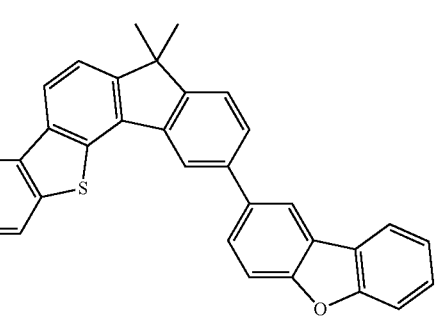
71
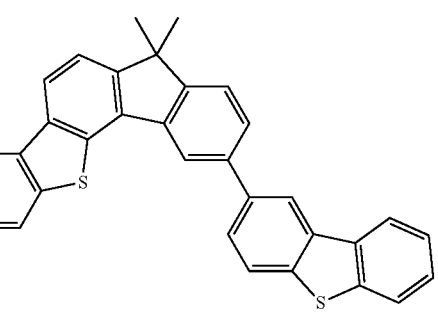
72
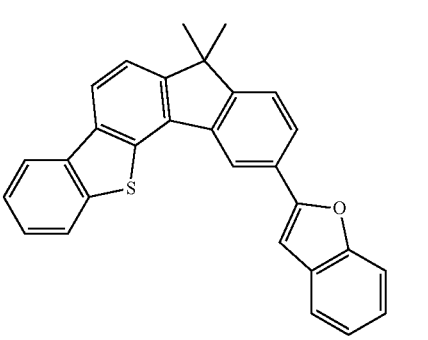
73
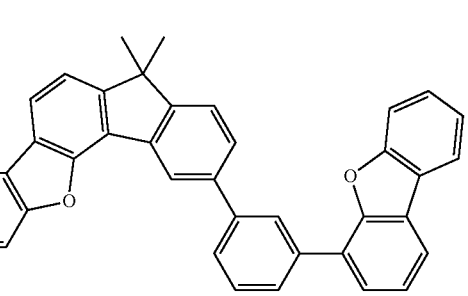

74
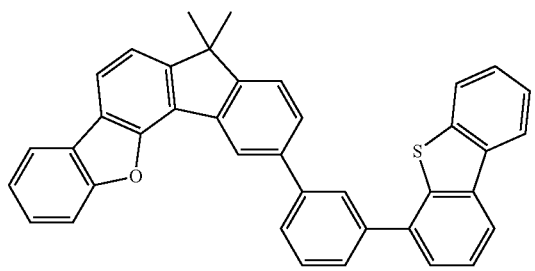
75
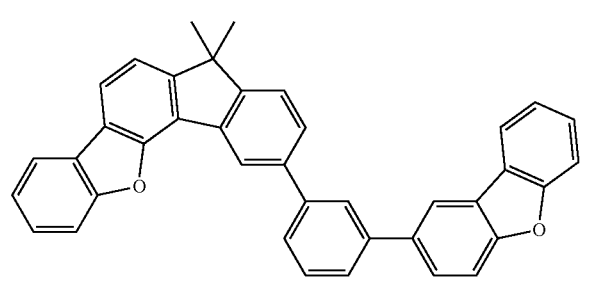
76
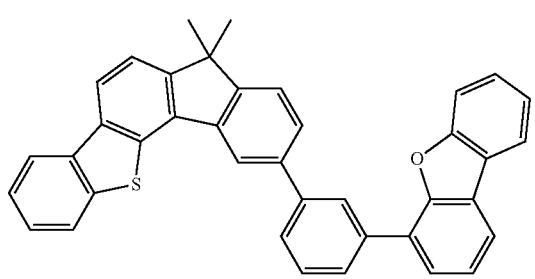
77
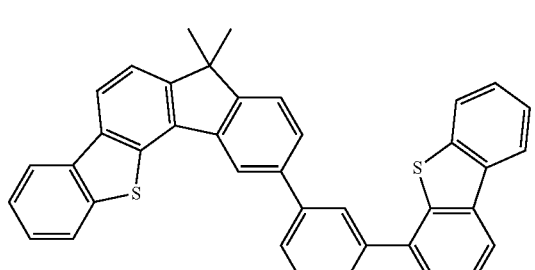
78
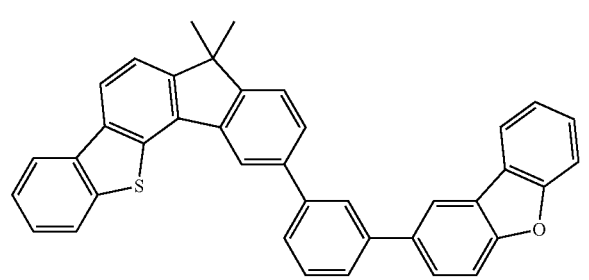
79
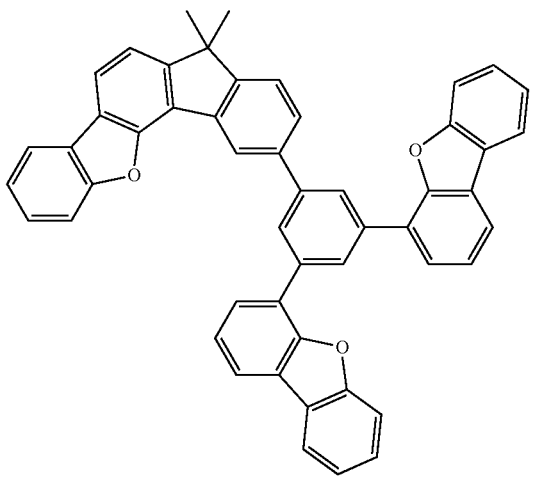
80
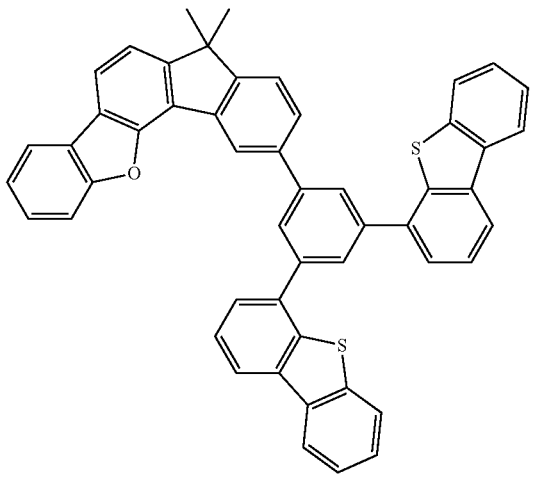
81
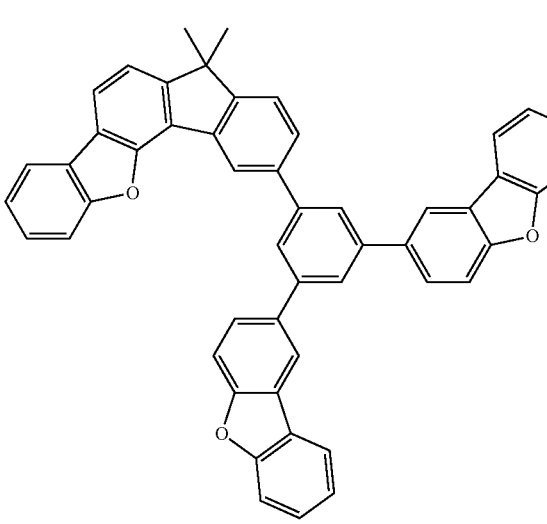

82
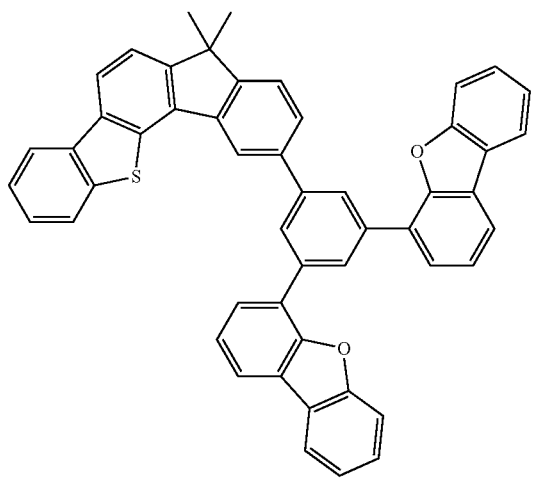
83
85
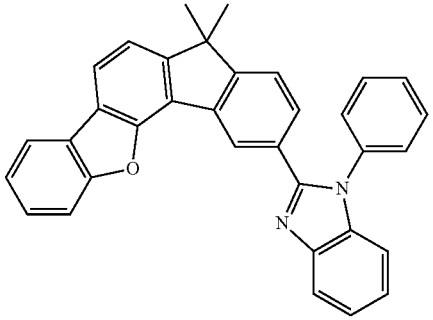
86
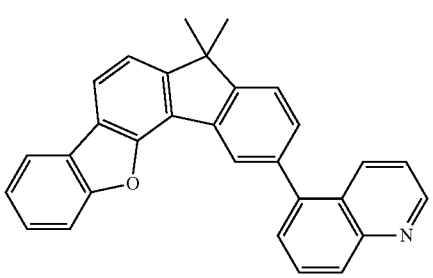
87
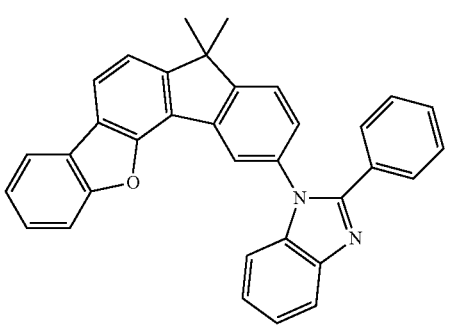
88
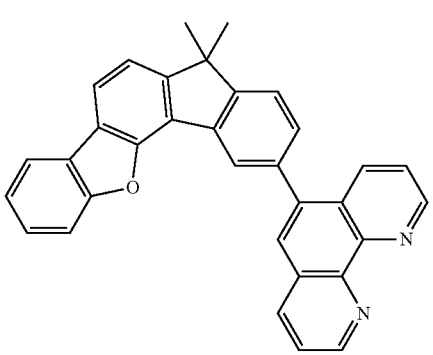
89
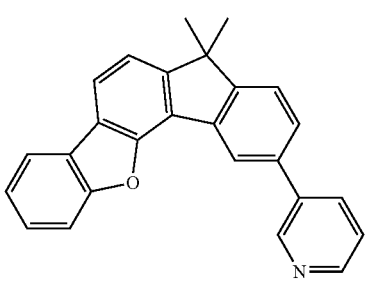

-continued

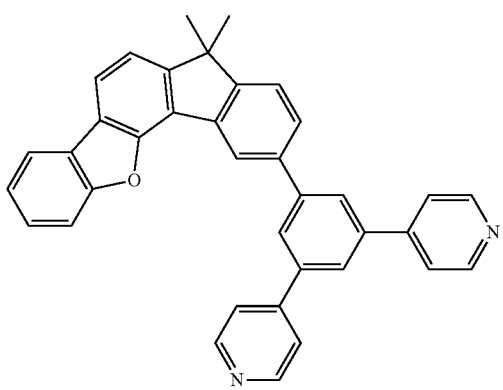

Hereinafter, an organic optoelectric device including the organic compound is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectric device is described referring to drawings.

Figure 2:
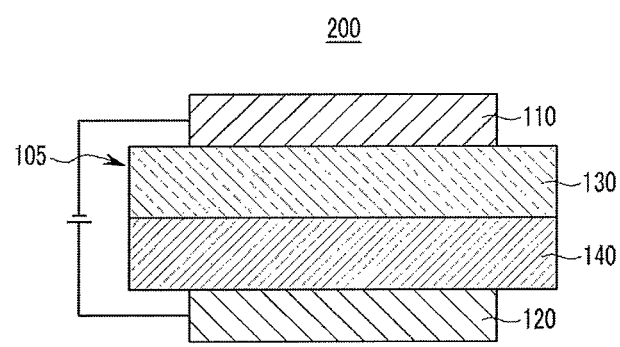

FIGS. 1 and 2 are cross-sectional views of each organic light emitting diode according to one embodiment.

Referring to FIG. 1, an organic optoelectric device 100 according to one embodiment includes an anode 120 and a cathode 110 facing each other and an organic layer 105 interposed between the anode 120 and cathode 110.

The anode 120 may be made of a conductor having a high work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like, a multi-layer structure material such as LiF/Al, LiO$_2$/Al, LiF/Ca, LiF/Al and BaF$_2$/Ca, but is not limited thereto.

The organic layer 105 includes an emission layer 130 including the organic compound.

The emission layer 130 may include, for example the organic compound at alone, a mixture of at least two kinds of the organic compound, or a mixture of the organic compound and another compound. In the case of the mixture of the organic compound and another compound, for example they may be included as a host and a dopant, and the organic compound may be, for example included as a host. The host may be, for example a phosphorescent host or fluorescent host, and may be, for example a phosphorescence host.

When the organic compound is included as a host, the dopant an inorganic, organic, or organic/inorganic compound, and may be selected known dopants.

Referring to FIG. 2, the organic light emitting diode 200 further include a hole auxiliary layer 140 as well as an emission layer 130. The hole auxiliary layer 140 increases hole injection and/or hole mobility between the anode 120 and the emission layer 230, and blocks electrons. The hole auxiliary layer 140 may be, for example a hole transport layer, a hole injection layer and/or an electron blocking layer, and may include at least one layer. The organic compound may be included in the emission layer 130 and/or the hole auxiliary layer 140. Even not shown in FIG. 1 or 2, the organic layer 105 may further include an electron injection layer, an electron transport layer, an electron auxiliary transport layer, a hole transport layer, a hole auxiliary transport layer, a hole injection layer, and a combination thereof, and each layer may include the organic compound of the present invention.

The organic light emitting diodes 100 and 200 may be manufactured by forming an anode or a cathode on a substrate, forming an organic layer in accordance with a dry coating method such as evaporation, sputtering, plasma plating, and ion plating or a wet coating method such as spin coating, dipping, and flow coating; and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

Synthesis of Organic Compound

Representative Synthesis Method

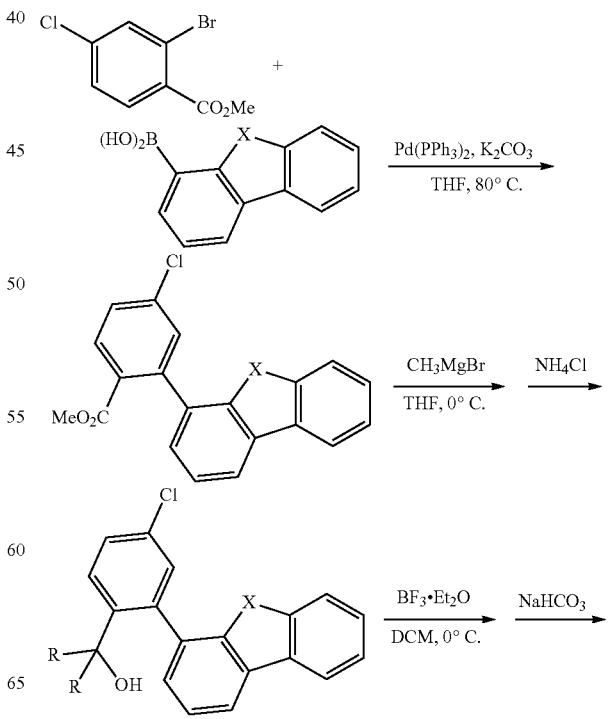

-continued

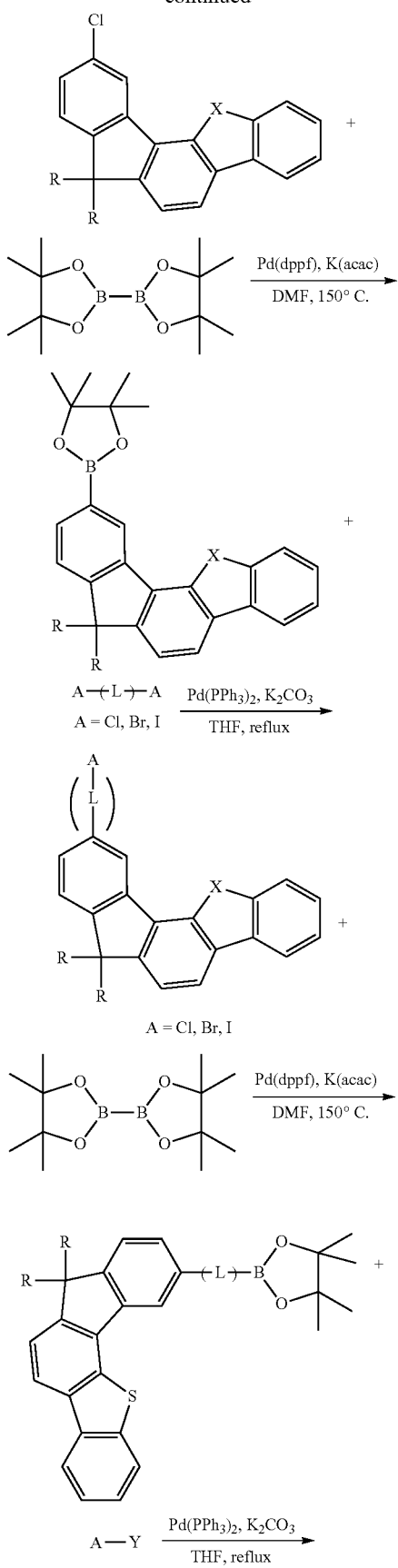

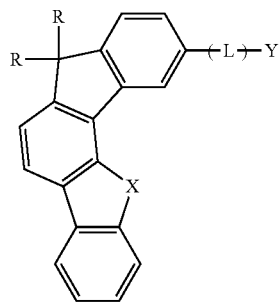

Synthesis Example 1

Preparation of Intermediate I-1

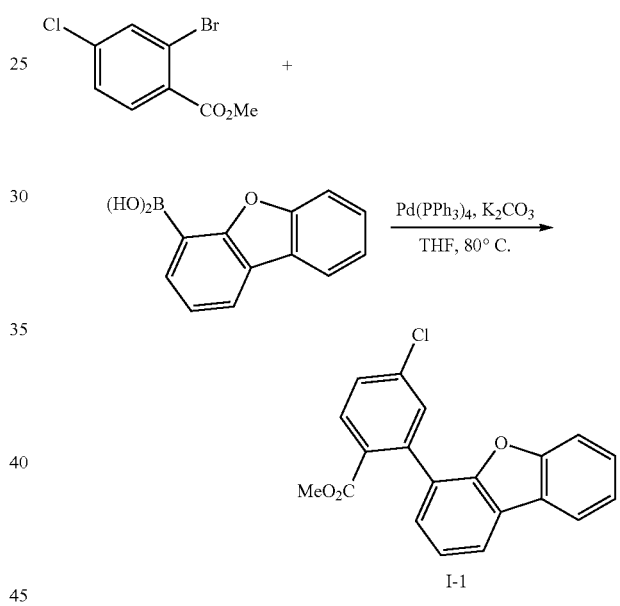

50 g (200 mmol) of methyl-2-bromo-4-chlorobenzoate was dissolved in 0.5 L of tetrahydrofuran (THF) under a nitrogen atmosphere, 46.7 g (220 mmol) of dibenzofuran-4-ylboronic acid and 4.63 g (4.01 mmol) of tetrakis(triphenylphosphine) palladium were added thereto, and the mixture was agitated. Then, 59.0 g (401 mmol) of potassium carbonate saturated in water was added thereto, and the obtained mixture was heated and refluxed at 80° C. for 21 hours. When the reaction was complete, water was added thereto, and the mixture was extracted with dichloromethane (DCM) and treated with anhydrous MgSO$_4$ to remove moisture and then, filtered and concentrated under a reduced pressure.

Then, a residue obtained therefrom was separated and purified through flash column chromatography, obtaining 47.7 g (71%) of the intermediate I-1.

HRMS (70 eV, EI+): m/z calcd for C20H13ClO3: 336.0553. found: 336.

Elemental Analysis: C, 71%; H, 4%

Synthesis Example 2

Preparation of Intermediate I-2

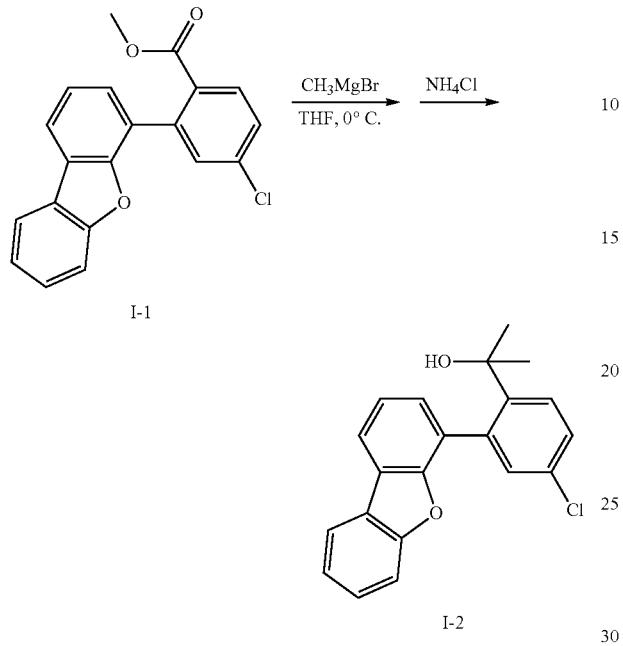

47.7 g (142 mmol) of the intermediate I-1 was dissolved in 0.5 L of tetrahydrofuran (THF) and then, cooled down to 0° C. under a nitrogen atmosphere. Then, 3.0 M (0.12 L, 354 mmol) of methyl magnesium bromide dissolved in diethyl ether was slowly added thereto in a dropwise fashion over one hour. The obtained mixture was agitated at room temperature for 19 hours. When the reaction was complete, 22.7 g (425 mmol) ammonium chloride dissolved in 0.12 L of water was added thereto to neutralize the reaction solution. The neutralized reaction solution was extracted with dichloromethane (DCM) and treated with anhydrous MgSO$_4$ to remove moisture and then, filtered and concentrated under a reduced pressure. 49.4 g (104%) of the intermediate I-2 was obtained.

HRMS (70 eV, EI+): m/z calcd for C21H17ClO2: 336.0917. found: 336.

Elemental Analysis: C, 75%; H, 5%

Synthesis Example 3

Preparation of Intermediate I-3

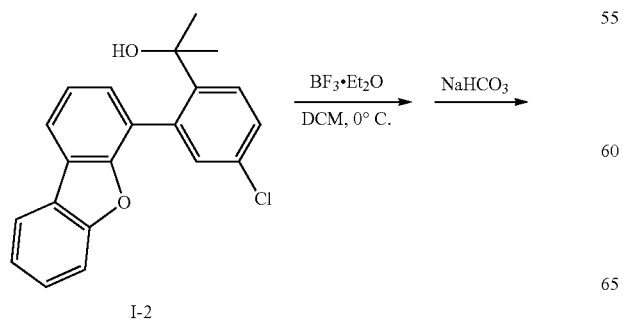

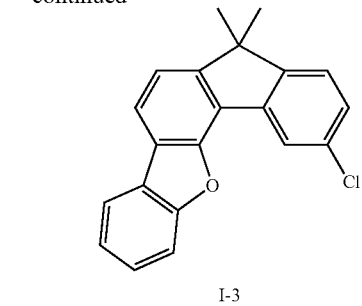

49.4 g (147 mmol) of the intermediate I-2 was dissolved in 0.25 L of dichloromethane (DCM) under a nitrogen atmosphere and then, cooled down to 0° C. Then, 22.9 g (161 mmol) of boron trifluoride dissolved in diethyl etherate was slowly added thereto in a dropwise fashion over one hour. The mixture was agitated at room temperature for 6 hours. When the reaction was complete, 13.6 g (161 mmol) of sodium bicarbonate dissolved in 0.14 L of water was added thereto to neutralize the reaction solution. The resulting mixture was extracted with dichloromethane (DCM) and then, treated with anhydrous MgSO$_4$ to remove moisture, and the obtained residue was separated and purified through flash column chromatography, obtaining 34 g (73%) of the intermediate I-3.

HRMS (70 eV, EI+): m/z calcd for C21H15ClO: 318.0811. found: 318.

Elemental Analysis: C, 79%; H, 5%

Synthesis Example 4

Synthesis of Intermediate I-4

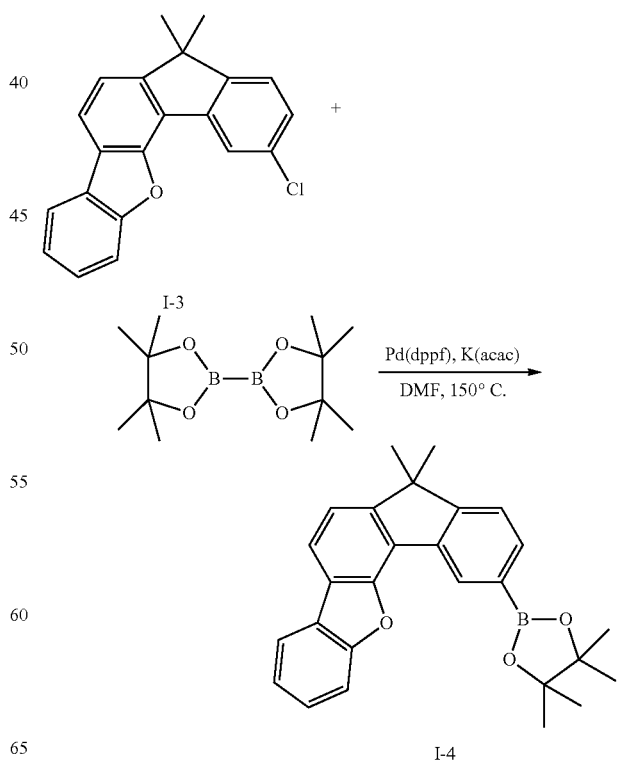

100 g (314 mmol) of the intermediate I-3 was dissolved in 1.0 L of dimethyl formamide (DMF) under a nitrogen atmosphere, 95.6 g (376 mmol) of bis(pinacolato)diboron, 2.56 g (3.14 mmol) of (1,1'-bis(diphenylphosphine)ferrocene)dichloropalladium (II) and 77.0 g (784 mmol) of potassium acetate were heated and refluxed at 150° C. for 65 hours. When the reaction was complete, was added to the reaction solution, and the mixture was filtered and then, dried in a vacuum oven. Then, a residue obtained therefrom was separated and purified through flash column chromatography, obtaining 81.4 g (63%) of the intermediate I-4.

HRMS (70 eV, EI+): m/z calcd for C27H27BO3: 410.2053. found: 410.

Elemental Analysis: C, 79%; H, 7%

Synthesis Example 5

Preparation of Intermediate I-5

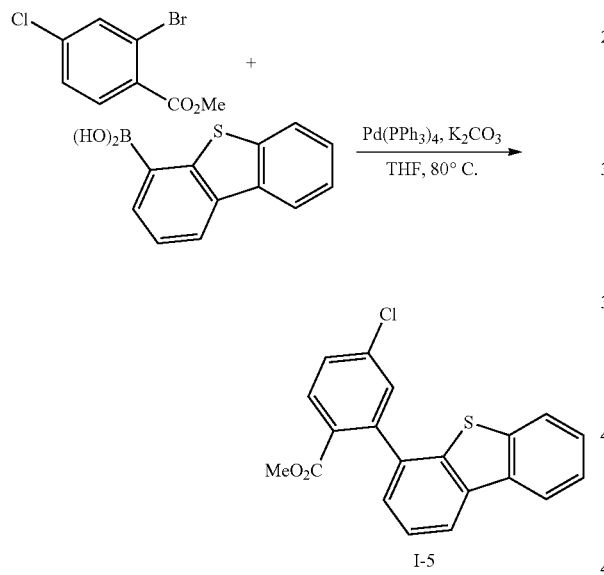

I-5

50 g (200 mmol) of methyl-2-bromo-4-chlorobenzoate was dissolved in 0.5 L of tetrahydrofuran (THF) under a nitrogen atmosphere, 50.2 g (220 mmol) of dibenzofuran-4-ylboronic acid and 4.63 g (4.01 mmol) of tetrakis(triphenylphosphine)palladium were added thereto, and the mixture was agitated. Then, 59.0 g (401 mmol) of potassium carbonate saturated in water was added thereto, and the obtained mixture was heated and refluxed at 80° C. for 18 hours. When the reaction was complete, water was added to the reaction solution, and the mixture was extracted with dichloromethane (DCM) and treated with anhydrous MgSO4 to remove moisture and then, filtered and concentrated under a reduced pressure. Then, a residue obtained therefrom was separated and purified through flash column chromatography, obtaining 56.5 g (80%) of the intermediate I-5.

HRMS (70 eV, EI+): m/z calcd for C20H13ClO2S: 352.0325. found: 352.

Elemental Analysis: C, 68%; H, 4%

Synthesis Example 6

Preparation of Intermediate I-6

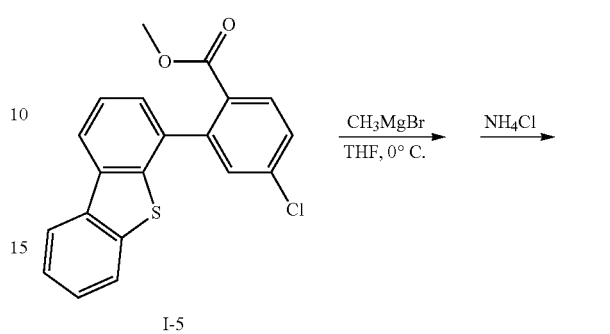

I-5

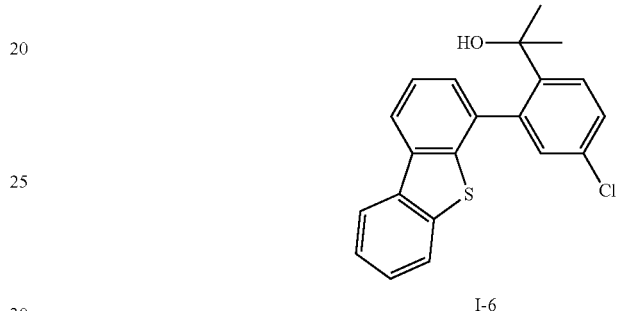

I-6

50 g (142 mmol) of the intermediate I-5 was dissolved in 0.5 L of tetrahydrofuran (THF) under a nitrogen atmosphere and then, cooled down to 0° C. Then, 3.0 M (0.12 L, 354 mmol) of methyl magnesium bromide dissolved in diethyl ether was slowly added thereto in a dropwise fashion over one hour. Then, the mixture was agitated at room temperature for 19 hours. When the reaction was complete, 22.7 g (425 mmol) of ammonium chloride dissolved in 0.12 L of water was added thereto to neutralize the reaction solution. Then, the obtained mixture was extracted with dichloromethane (DCM) and treated with anhydrous MgSO4 to remove moisture and then, filtered and concentrated under a reduced pressure. 49.1 g (98%) of the intermediate I-6 was obtained.

HRMS (70 eV, EI+): m/z calcd for C21H17ClOS: 352.0689. found: 352.

Elemental Analysis: C, 71%; H, 5%

Synthesis Example 7

Preparation of Intermediate I-7

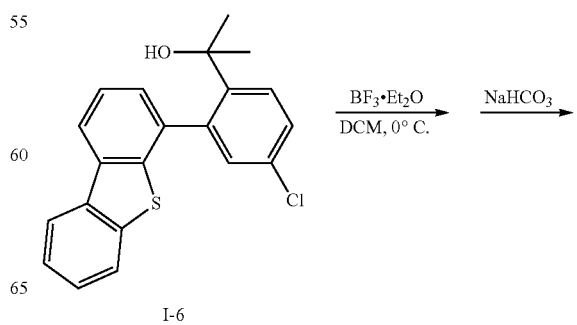

I-6

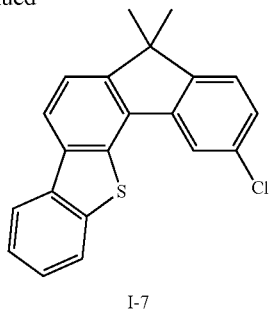

I-7

40 g (113 mmol) of the intermediate I-6 was dissolved in 0.6 L of dichloromethane (DCM) under a nitrogen atmosphere and then, cooled down to 0° C. Then, 24.1 g (170 mmol) of borontrifluoride dissolved in diethyl etherate was slowly added thereto in a dropwise fashion over one hour. The mixture was agitated at room temperature for 5 hours. When the reaction was complete, 14.3 g (170 mmol) of sodium bicarbonate dissolved in 0.14 L of water was added thereto to neutralize the reaction solution. Then, the obtained mixture was extracted with dichloromethane (DCM) and treated with anhydrous MgSO$_4$ to remove moisture, and a residue obtained therefrom was separated and purified through flash column chromatography, obtaining 29.9 g (79%) of the intermediate I-7.

HRMS (70 eV, EI+): m/z calcd for C2H15ClS: 334.0583. found: 334.

Elemental Analysis: C, 75%; H, 5%

Synthesis Example 8

Synthesis of Intermediate I-8

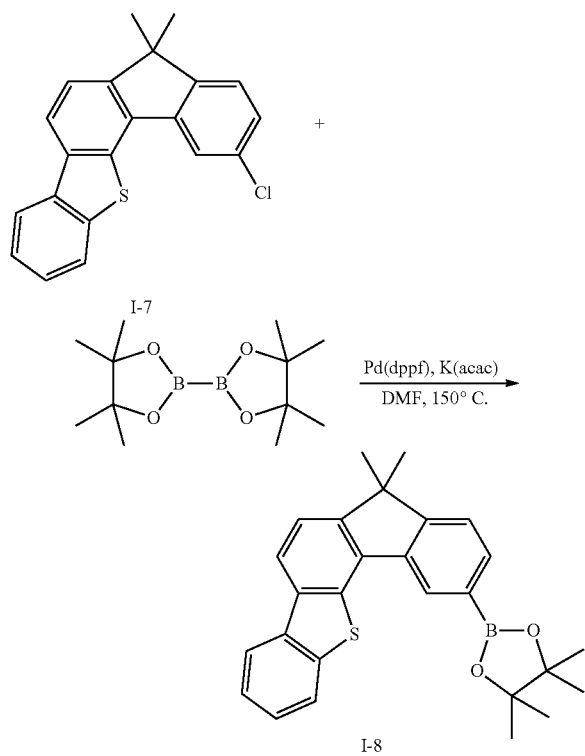

100 g (299 mmol) of the intermediate I-7 was dissolved in 1.0 L of dimethyl formamide (DMF) under a nitrogen atmosphere, 91.0 g (358 mmol) of bis(pinacolato)diboron, 2.44 g (2.99 mmol) of 1,1'-bis(diphenylphosphine)ferrocene)dichloropalladium (II) and 73.4 g (748 mmol) of potassium acetate were heated and refluxed at 150° C. for 32 hours. When the reaction was complete, water was added to the reaction solution, and the mixture was filtered and dried in a vacuum oven. Then, a residue obtained therefrom was separated and purified through flash column chromatography, obtaining 89.2 g (70%) of the intermediate I-8.

HRMS (70 eV, EI+): m/z calcd for C27H27BO2S: 426.1825. found: 426.

Elemental Analysis: C, 76%; H, 6%

Synthesis Example 9

Preparation of Intermediate I-9

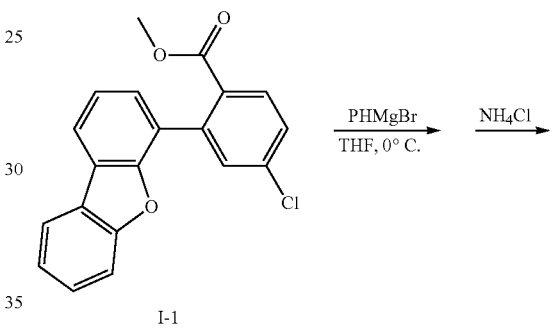

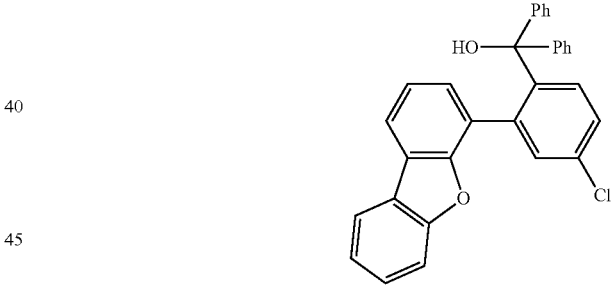

50 g (148 mmol) of the intermediate I-1 was dissolved in 0.5 L of tetrahydrofuran (THF) under a nitrogen atmosphere and then, cooled down to 0° C. Then, 3.0 M (0.12 L, 370 mmol) of phenyl magnesium bromide dissolved in diethyl ether were slowly added thereto in a dropwise fashion over one hour. Then, the obtained mixture was agitated at room temperature for 30 hours. When the reaction was complete, 23.7 g (444 mmol) of ammonium chloride dissolved in 0.12 L of water was added thereto to neutralize the reaction solution. Then, the mixture was extracted with dichloromethane (DCM) and treated with anhydrous MgSO$_4$ to remove moisture and then, filtered and concentrated under a reduced pressure. 68.2 g (100%) of the intermediate I-9 was obtained.

HRMS (70 eV, EI+): m/z calcd for C31H21ClO2: 460.1230. found: 460.

Elemental Analysis: C, 81%; H, 5%

Synthesis Example 10

Preparation of Intermediate I-10

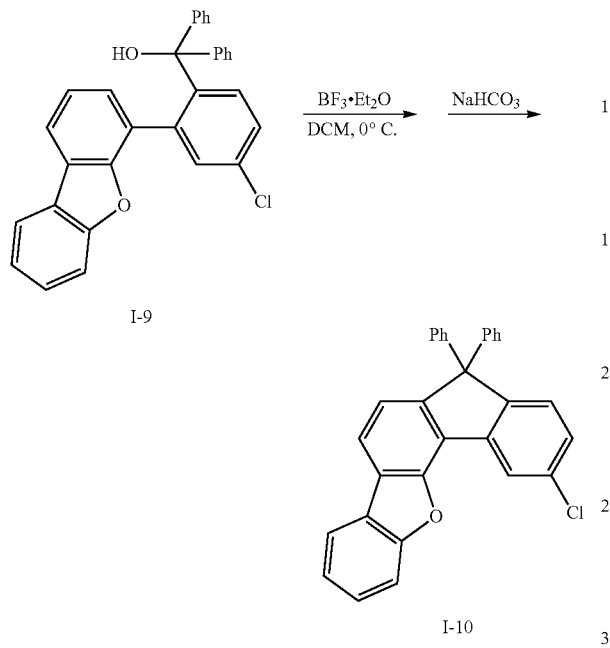

68.2 g (148 mmol) of the intermediate I-9 was dissolved in 0.34 L of dichloromethane (DCM) under a nitrogen atmosphere and then, cooled down to 0° C. Then, 23.1 g (163 mmol) of borontrifluoride dissolved in diethyl etherate was slowly added thereto in a dropwise fashion over one hour. The obtained mixture was agitated at room temperature for 6 hours. When the reaction was complete, 13.7 g (163 mmol) of sodium bicarbonate dissolved in 0.14 L of water was added thereto to neutralize the reaction solution. Then, the resultant was extracted with dichloromethane (DCM) and treated with anhydrous MgSO$_4$ to remove moisture, and a residue obtained therefrom was separated and purified through flash column chromatography, obtaining 60.3 g (92%) of the intermediate I-10.

HRMS (70 eV, EI+): m/z calcd for C31H19ClO: 442.1124. found: 442.

Elemental Analysis: C, 84%; H, 4%

Synthesis Example 11

Synthesis of Intermediate I-11

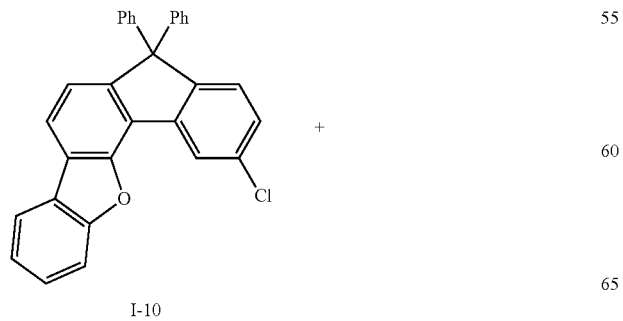

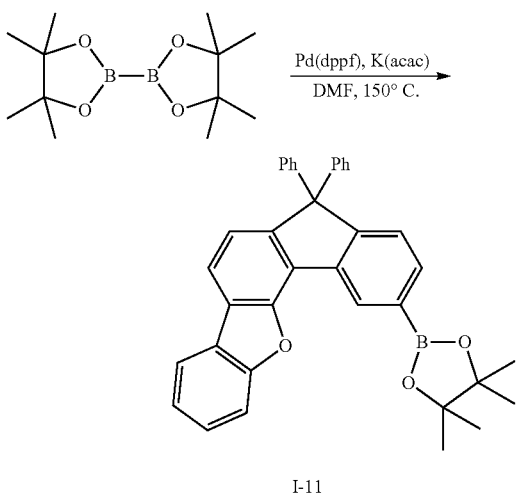

60 g (112 mmol) of the intermediate I-10 was dissolved in 0.5 L of dimethyl formamide (DMF) under a nitrogen atmosphere, 34.2 g (135 mmol) of bis(pinacolato)diboron, 0.91 g (1.12 mmol) of (1,1'-bis(diphenylphosphine)ferrocene)dichloropalladium (II) and 27.5 g (280 mmol) of potassium acetate were added thereto, and the mixture was heated an refluxed at 150° C. for 70 hours. When the reaction was complete, water was added to the reaction solution, and the mixture was filtered and then, dried in a vacuum oven. Then, a residue obtained therefrom was separated and purified through flash column chromatography, obtaining 41.3 g (69%) of the intermediate I-11.

HRMS (70 eV, EI+): m/z calcd for C37H31BO3: 534.2366. found: 534.

Elemental Analysis: C, 83%; H, 6%

Synthesis Example 12

Synthesis of Intermediate I-12

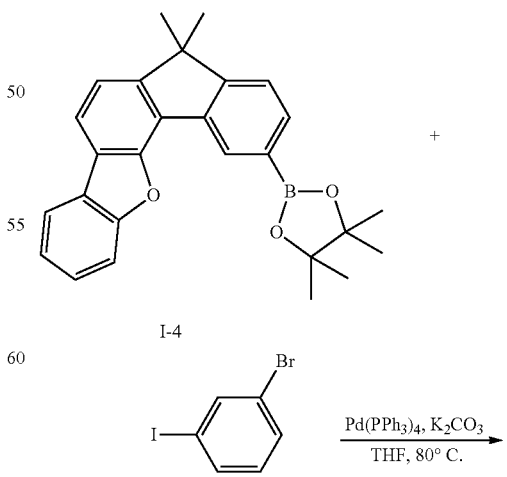

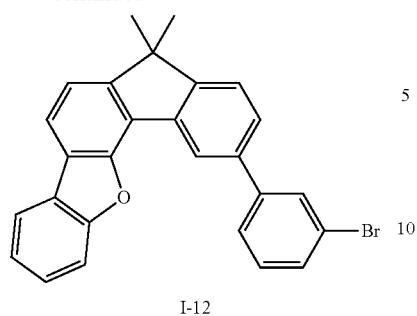

I-12

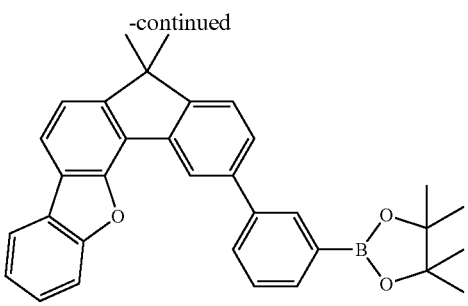

I-13

50 g (122 mmol) of the intermediate I-4 was dissolved in 0.45 L of tetrahydrofuran (THF) under a nitrogen atmosphere, 41.4 g (146 mmol) of 1-bromo-3-iodobenzene and palladium and 1.41 g (1.22 mmol) of tetrakis(triphenylphosphine) were added thereto, and the mixture was agitated. Then, 42.2 g (305 mmol) of potassium carbonate saturated in water was added thereto, and the mixture was heated and refluxed at 80° C. for 15 hours. When the reaction was complete, water was added to the reaction solution, and the mixture was extracted with dichloromethane (DCM) and treated with anhydrous MgSO₄ to remove moisture and then, filtered and concentrated under a reduced pressure. Then, a residue obtained therefrom was separated and purified through flash column chromatography, obtaining 42.9 g (80%) of the intermediate I-12.

HRMS (70 eV, EI+): m/z calcd for C27H19BrO: 438.0619. found: 438.

Elemental Analysis: C, 74%; H, 4%

Synthesis Example 13

Synthesis of Intermediate I-13

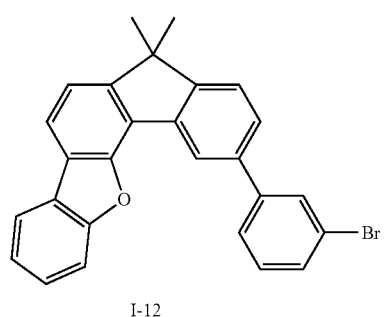

I-12

+

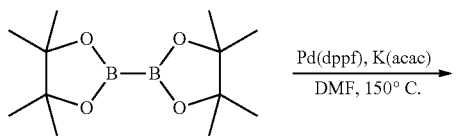

Pd(dppf), K(acac)
———————→
DMF, 150° C.

40 g (91.0 mmol) of the intermediate I-12 was dissolved in 0.3 L of dimethyl formamide (DMF) under a nitrogen atmosphere, 27.7 g (109 mmol) of bis(pinacolato)diboron, 0.74 g (0.91 mmol) of (1,1'-bis(diphenylphosphine)ferrocene)dichloropalladium (11) and 22.3 g (228 mmol) of potassium acetate were added thereto, and the mixture was heated and refluxed at 150° C. for 20 hours. When the reaction was complete, water was added to the reaction solution, and the mixture was filtered and dried in a vacuum oven. Then, a residue obtained therefrom was separated and purified through flash column chromatography, obtaining 33.2 g (75%) of the intermediate I-13.

HRMS (70 eV, EI+): m/z calcd for C33H31BO3: 486.2366. found: 486.

Elemental Analysis: C, 81%; H, 6%

Synthesis Example 14

Synthesis of Intermediate I-14

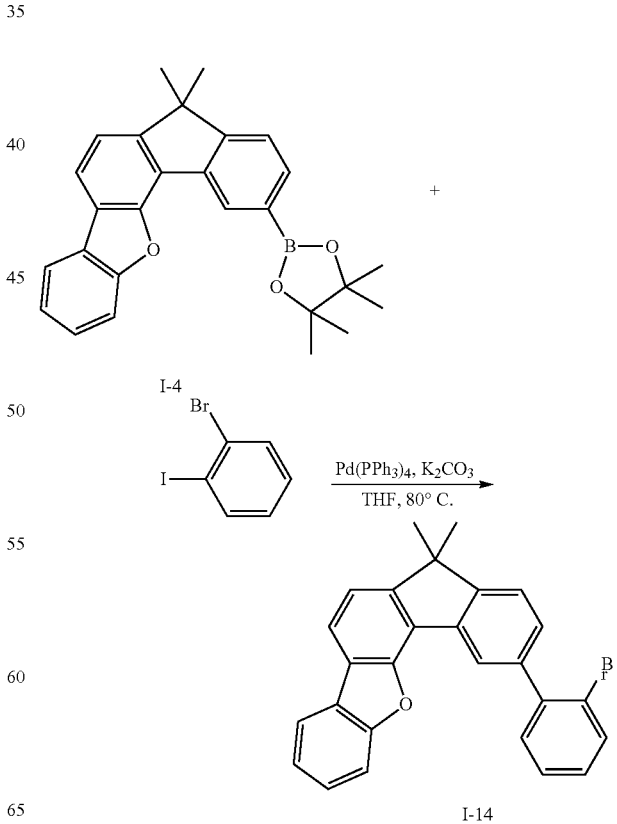

I-14

50 g (122 mmol) of the intermediate I-4 was dissolved in 0.45 L of tetrahydrofiran (THF) under a nitrogen atmosphere, 41.4 g (146 mmol) of 1-bromo-2-iodobenzene and 1.41 g (1.22 mmol) of tetrakis(triphenylphosphine)palladium were added thereto, and the mixture was agitated. Then, 42.2 g (305 mmol) of potassium carbonate saturated in water was added thereto, and the obtained mixture was heated and refluxed at 80° C. for 30 hours. When the reaction was complete, water was added to the reaction solution, and the mixture was extracted with dichloromethane (DCM) and treated with anhydrous MgSO$_4$ to remove moisture and then, filtered and concentrated under a reduced pressure. Then, a residue obtained therefrom was separated and purified through flash column chromatography, obtaining 38.1 g (71%) of the intermediate I-14.

HRMS (70 eV, EI+): m/z calcd for C27H19BrO: 438.0619. found: 438.

Elemental Analysis: C, 74%; H, 4%

Synthesis Example 15

Synthesis of Intermediate I-15

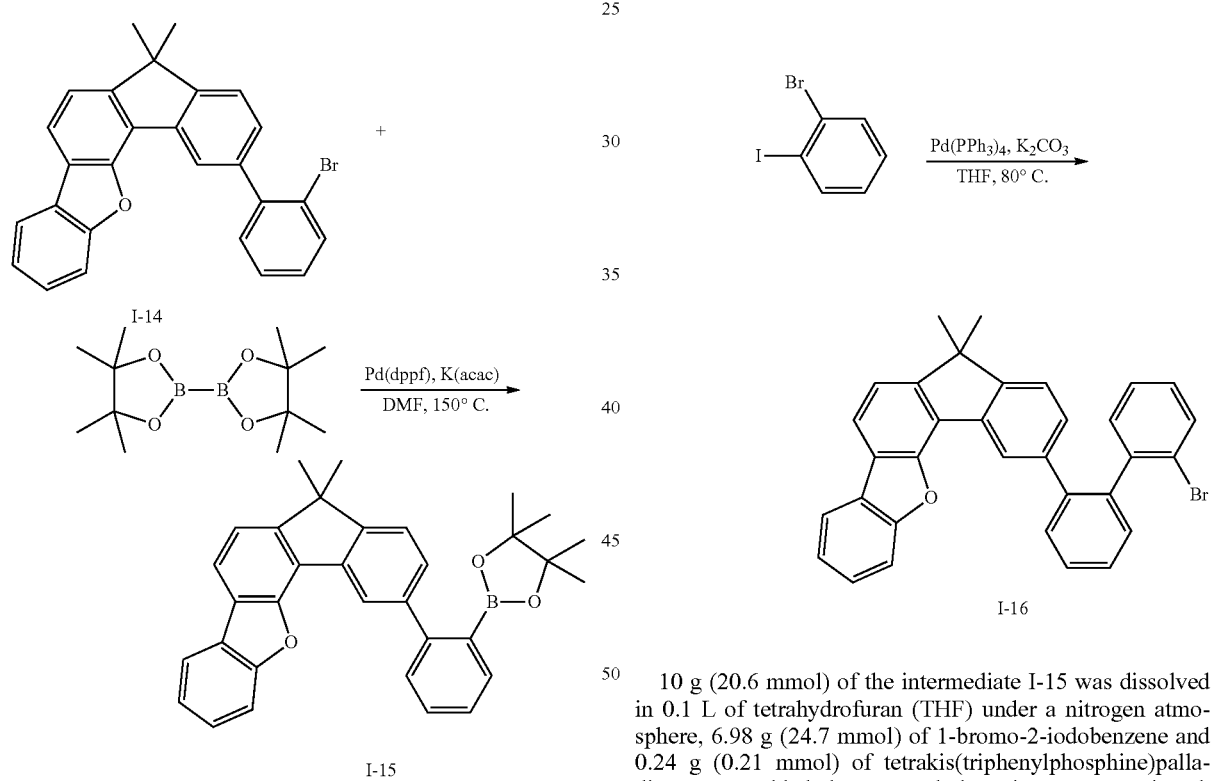

I-15

30 g (68.3 mmol) of the intermediate I-14 was dissolved in 0.3 L of dimethyl formamide (DMF) under a nitrogen atmosphere, 20.8 g (81.9 mmol) of bis(pinacolato)diboron, 0.56 g (0.68 mmol) of (1,1'-bis(diphenylphosphine)ferrocene)dichloropalladium (II) and 16.8 g (228 mmol) of potassium acetate were added thereto, and the mixture as heated and refluxed at 150° C. for 36 hours. When the reaction was complete, water was filtered and then, dried in a vacuum oven. Then, a residue obtained therefrom was separated and purified through flash column chromatography, obtaining 14.9 g (45%) of the intermediate I-15.

HRMS (70 eV, EI+): m/z calcd for C33H31BO3: 486.2366. found: 486.

Elemental Analysis: C, 81%; H, 6%

Synthesis Example 16

Synthesis of Intermediate I-16

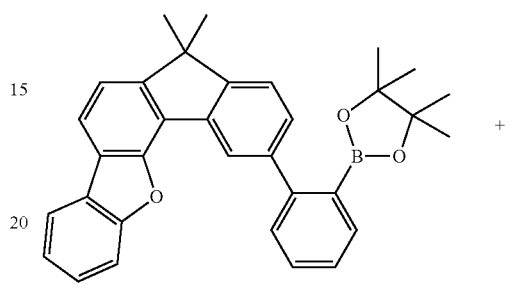

I-15

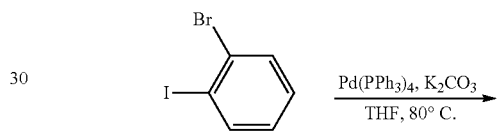

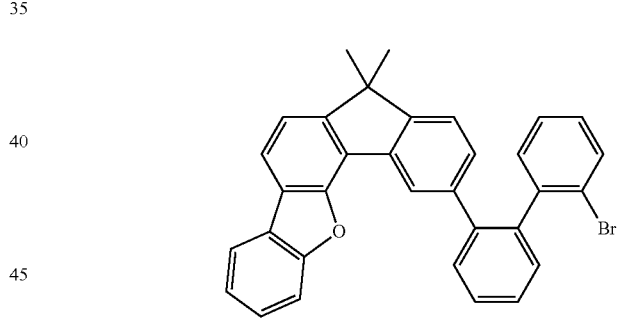

I-16

10 g (20.6 mmol) of the intermediate I-15 was dissolved in 0.1 L of tetrahydrofuran (THF) under a nitrogen atmosphere, 6.98 g (24.7 mmol) of 1-bromo-2-iodobenzene and 0.24 g (0.21 mmol) of tetrakis(triphenylphosphine)palladium were added thereto, and the mixture was agitated. Then, 7.12 g (51.5 mmol) of potassium carbonate saturated in water was heated and refluxed at 80° C. for 33 hours. When the reaction was complete, water was added to the reaction solution, and the mixture was extracted with dichloromethane (DCM) and treated with anhydrous MgSO$_4$ to remove moisture and then, filtered and concentrated under a reduced pressure. Then, a residue obtained therefrom was separated and purified through flash column chromatography, obtaining 7.96 g (75%) of the intermediate I-16.

HRMS (70 eV, EI+): m/z calcd for C33H23BrO: 514.0932. found: 514.

Elemental Analysis: C, 77%; H, 5%

Synthesis Example 17

Synthesis of Intermediate I-17

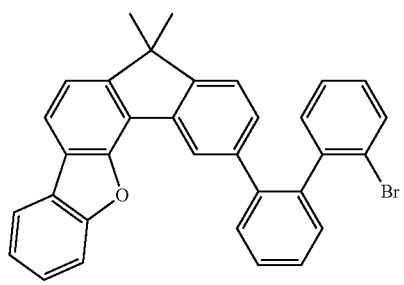

I-16

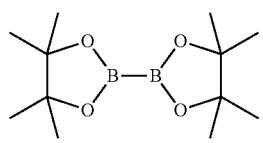

Pd(dppf), K(acac)
DMF, 150° C.

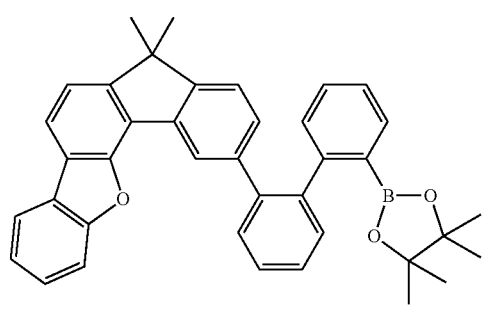

I-17

7 g (13.6 mmol) of the intermediate I-16 was dissolved in 0.06 L of dimethyl formamide (DMF) under a nitrogen atmosphere, 4.14 g (16.3 mmol) of bis(pinacolato)diboron, 0.11 g (0.14 mmol) of 1,1'-bis(diphenylphosphine)ferrocene)dichloropalladium (11) and 3.34 g (34.0 mmol) of potassium acetate were added thereto, and the mixture was heated and refluxed at 150° C. for 42 hours. When the reaction was complete, water was added to the reaction solution, and the mixture was filtered and dried in a vacuum oven. Then, a residue obtained therefrom was separated and purified through flash column chromatography, obtaining 3.83 g (50%) of the intermediate I-17.

HRMS (70 eV, EI+): m/z calcd for C39H35BO3: 562.2679. found: 562.

Elemental Analysis: C, 83%; H, 6%

Synthesis Example 18

Synthesis of Intermediate I-18

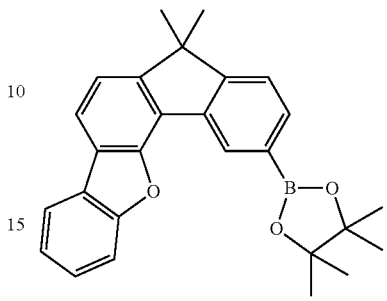

I-4

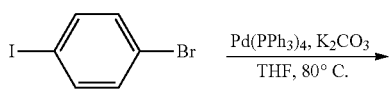

Pd(PPh3)4, K2CO3
THF, 80° C.

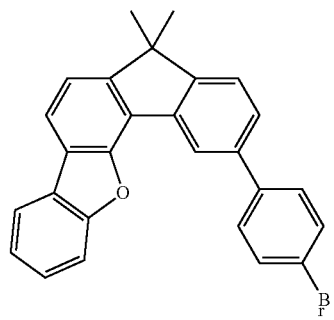

I-18

50 g (122 mmol) of the intermediate I-4 was dissolved in 0.46 L of tetrahydrofuran (THF) under a nitrogen atmosphere, 41.4 g (146 mmol) of 1-bromo-4-iodobenzene and 1.41 g (1.22 mmol) of tetrakis(triphenylphosphine)palladium were added thereto, and the mixture was agitated. Then, 42.2 g (305 mmol) of potassium carbonate saturated in water was added thereto, and the obtained mixture was heated and refluxed at 80° C. for 8 hours. When the reaction was complete, water was added to the reaction solution, and the mixture was extracted with dichloromethane (DCM) and treated with anhydrous MgSO4 to remove moisture and then, filtered and concentrated under a reduced pressure. Then, a residue obtained therefrom was separated and purified through flash column chromatography, obtaining 48.2 g (90%) of the intermediate I-18.

HRMS (70 eV, EI+): m/z calcd for C27H19BrO: 438.0619. found: 438.

Elemental Analysis: C, 74%; H, 4%

Synthesis Example 19

Synthesis of Intermediate I-19

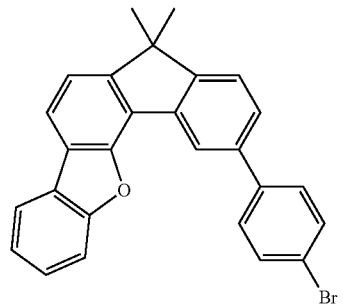

I-18

+

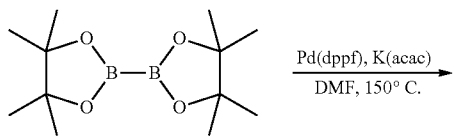

Pd(dppf), K(acac)
DMF, 150° C.

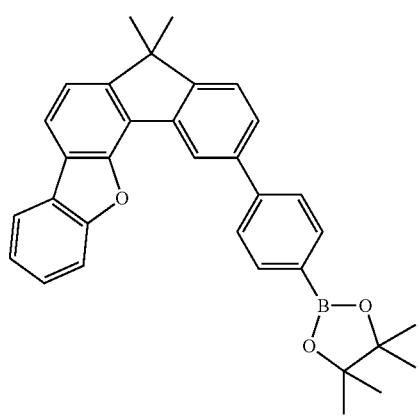

I-19

40 g (91.0 mmol) of the intermediate I-18 was dissolved in 0.35 L of dimethyl formamide (DMF) under a nitrogen atmosphere, 27.7 g (109 mmol) of bis(pinacolato)diboron, 0.74 g (0.91 mmol) of (1,1'-bis(diphenylphosphine)ferrocene)dichloropalladium (II), and 22.3 g (228 mmol) of potassium acetate were added thereto, and the mixture was heated and refluxed at 150° C. for 9 hours. When the reaction was complete, water was added to reaction solution, and the mixture was filtered and then, dried in a vacuum oven. Then, a residue obtained therefrom was purified through flash column chromatography, obtaining 42.1 g (95%) of the intermediate I-19.

HRMS (70 eV, EI+): m/z calcd for C33H31BO3: 486.2366. found: 486.

Elemental Analysis: C, 81%; H, 6%

Synthesis Example 20

Synthesis of Intermediate I-20

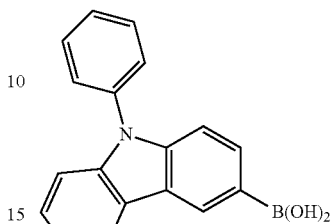

+

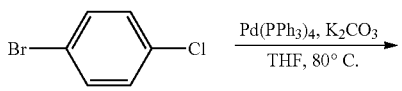

Pd(PPh3)4, K2CO3
THF, 80° C.

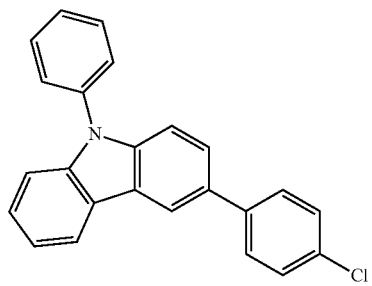

I-20

100 g (348 mmol) of 9-phenyl-9H-carbazol-3-ylboronic acid was dissolved in 0.9 L of tetrahydrofuran (THF) under a nitrogen atmosphere, 73.3 g (383 mmol) of 1-bromo-4-chlorobenzene and 4.02 g (3.48 mmol) of tetrakis(triphenylphosphine)palladium were added thereto, and the mixture was agitated. Then, 128 g (870 mmol) of potassium carbonate was added thereto, and the mixture was heated and refluxed at 80° C. for 8 hours. When the reaction was complete, water was added to the reaction solution, and the mixture was extracted with dichloromethane (DCM) and treated with anhydrous MgSO4 to remove moisture and then, filtered and concentrated under a reduced pressure. Then, a residue obtained therefrom was separated and purified through flash column chromatography, obtaining 119 g (97%) of the intermediate I-20.

HRMS (70 eV, EI+): m/z calcd for C24H16ClN: 353.0971. found: 353.

Elemental Analysis: C, 81%; H, 5%

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example 1

Synthesis of Compound 1

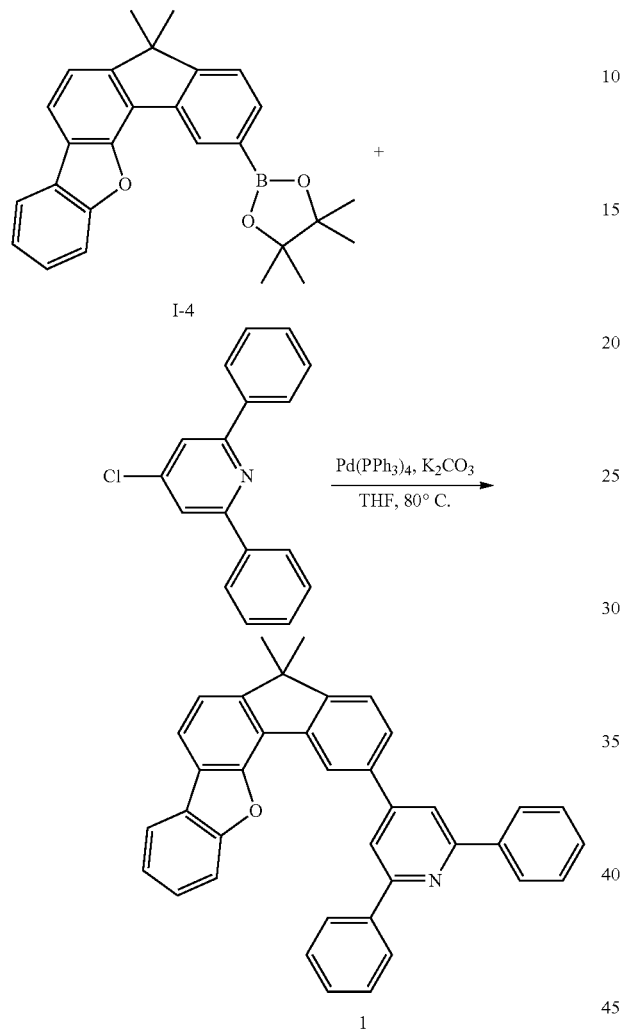

20 g (48.7 mmol) of the intermediate I-4 was dissolved in 0.17 L of tetrahydrofuran (THF) under a nitrogen atmosphere, 13.0 g (48.7 mmol) of 4-chloro-2,6-diphenylpyridine and 1.69 g (1.46 mmol) of tetrakis(triphenylphosphine) palladium were added thereto, and the mixture was agitated. Then, 16.8 g (122 mmol) of potassium carbonate saturated in water was added thereto, and the obtained mixture was heated and refluxed at 80° C. for 8 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 21.3 g (85%) of the compound 1.

HRMS (70 eV. EI+): m/z calcd for $C_{38}H_{27}NO$: 513.2093. found: 459.

Elemental Analysis: C, 89%; H, 5%

Example 2

Synthesis of Compound 2

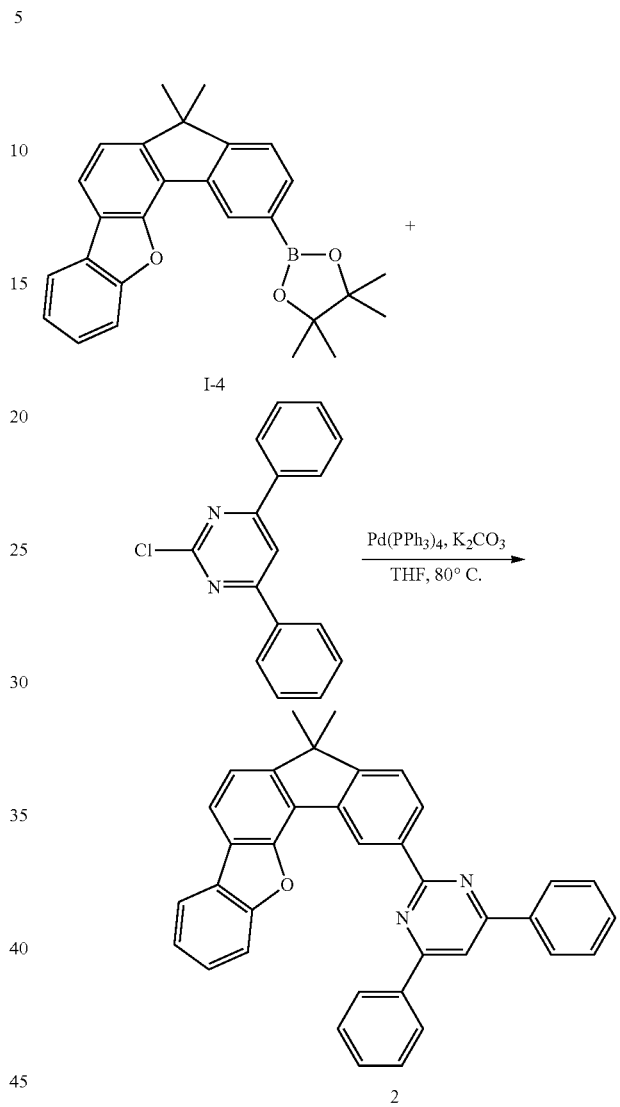

20 g (48.7 mmol) of the intermediate I-4 was dissolved in 0.17 L of tetrahydrofuran (THF) under a nitrogen atmosphere, 13.0 g (48.7 mmol) of 2-chloro-4,6-diphenylpyrimidine and 1.69 g (1.46 mmol) of tetrakis(triphenylphosphine) palladium were added thereto, and the mixture was agitated. 16.8 g (122 mmol) of potassium carbonate saturated in water was added thereto, and the obtained mixture was heated and refluxed at 80° C. for 6 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 22.8 g (91%) of the compound 2.

HRMS (70 eV, EI+): m/z calcd for $C_{37}H_{26}N_2O$: 514.2045. found: 514.

Elemental Analysis: C, 86%; H, 5%

Example 3

Synthesis of Compound 3

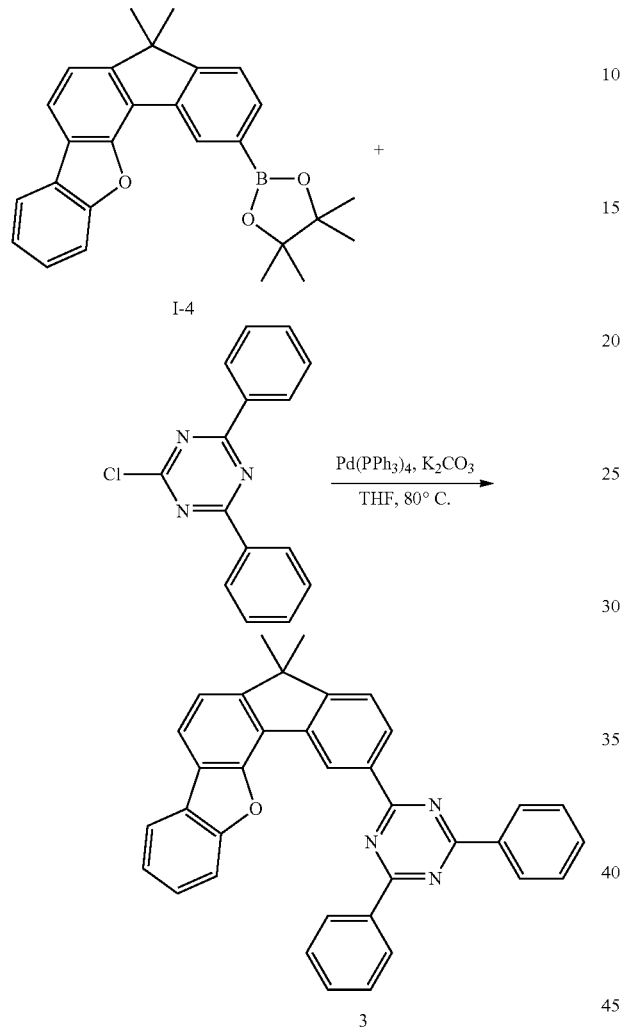

20 g (48.7 mmol) of the intermediate I-4 was dissolved in 0.17 L of tetrahydrofuran (THF) under a nitrogen atmosphere, 13.0 g (48.7 mmol) of 2-chloro-4,6-diphenyl-1,3,5-triazine and 1.69 g (1.46 mmol) of tetrakis(triphenylphosphine)palladium were added thereto, and the mixture was agitated. Then, 16.8 g (122 mmol) of potassium carbonate was added thereto, and the obtained mixture was heated and refluxed at 80° C. for 7 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue therefrom was separated and purified through flash column chromatography, obtaining 21.8 g (87%) of the compound 3.

HRMS (70 eV, EI+): m/z calcd for C36H25N3O: 515.1998. found: 515.

Elemental Analysis: C, 84%; H, 5%

Example 4

Synthesis of Compound 4

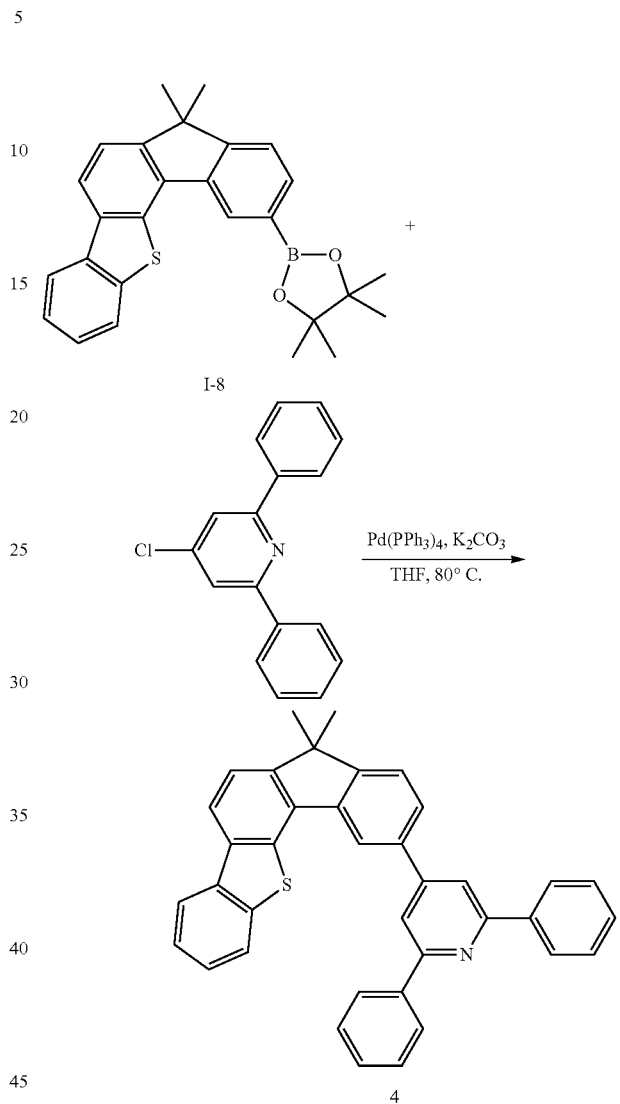

20 g (46.9 mmol) of the intermediate I-8 was dissolved in 0.16 L of tetrahydrofuran (THF) under a nitrogen atmosphere, 12.5 g (46.9 mmol) of 4-chloro-2,6-diphenylpyridine and 1.63 g (1.41 mmol) of tetrakis(triphenylphosphine) palladium were added thereto, and the mixture was agitated. Then, 16.2 g (117 mmol) of potassium carbonate saturated in water was added thereto, and the obtained mixture was heated and refluxed at 80° C. for 6 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 22.1 g (89%) of the compound 4.

HRMS (70 eV, EI+): m/z calcd for C38H27NS: 529.1864. found: 529.

Elemental Analysis: C, 86%; H, 5%

Example 5

Synthesis of Compound 5

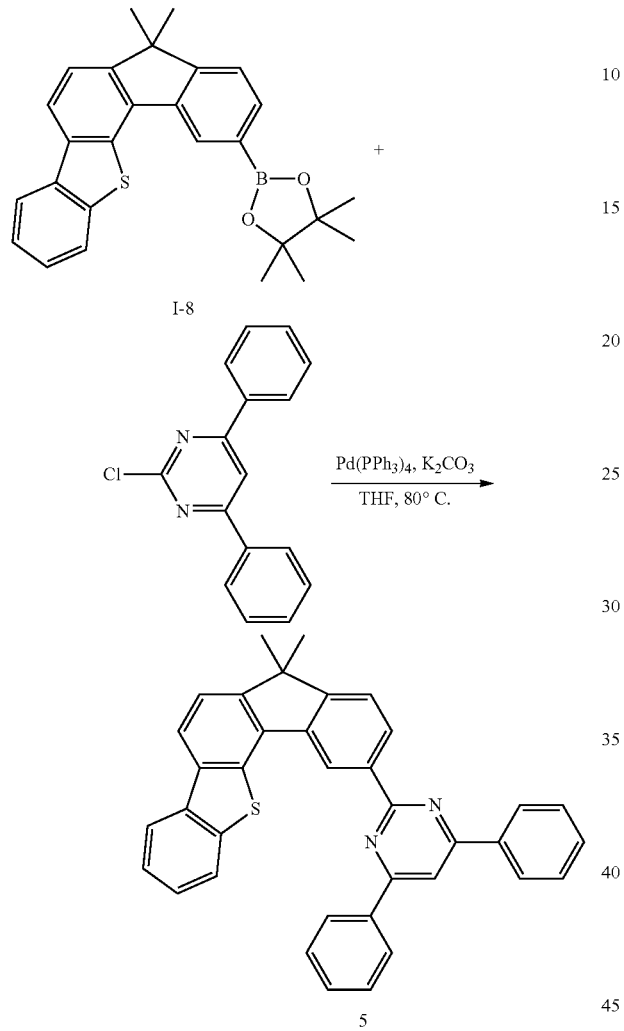

20 g (46.9 mmol) of the intermediate I-8 was dissolved in 0.16 L of tetrahydrofuran (THF) under a nitrogen atmosphere, 12.5 g (46.9 mmol) of 2-chloro-4,6-diphenylpyrimidine and 1.63 g (1.41 mmol) of tetrakis(triphenylphosphine)palladium were added thereto, and the mixture was agitated. Then, 16.2 g (117 mmol) of potassium carbonate was added thereto, and the obtained mixture was heated and refluxed at 80° C. for 6 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 23.6 g (95%) of the compound 5.

HRMS (70 eV, EI+): m/z calcd for $C_{37}H_{26}N_2S$: 530.1817. found: 530.

Elemental Analysis: C, 84%; H, 5%

Example 6

Synthesis of Compound 6

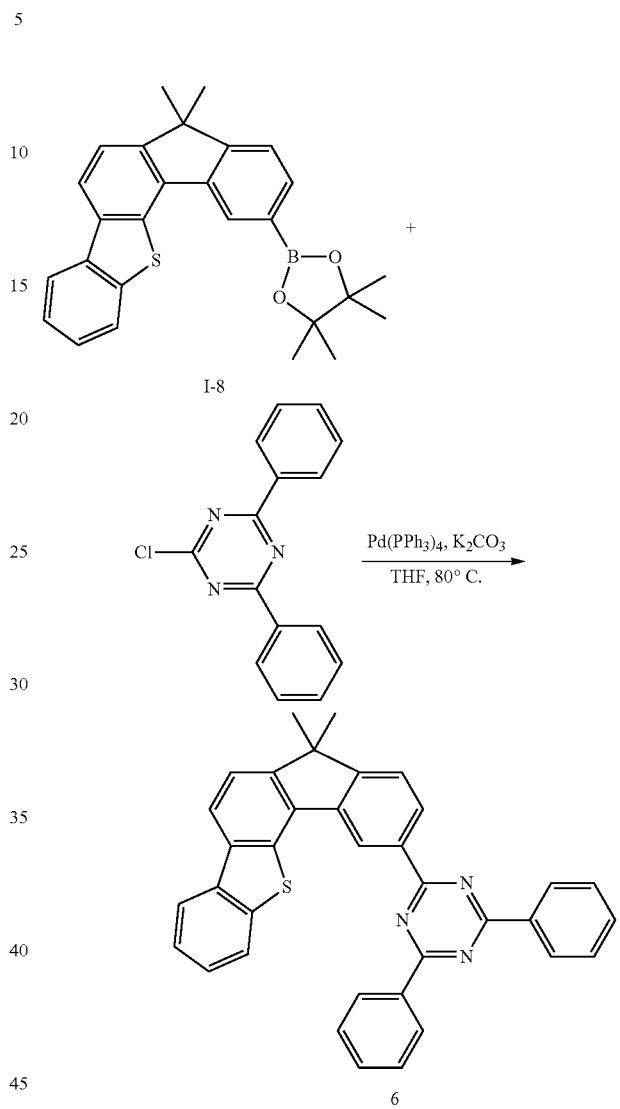

20 g (46.9 mmol) of the intermediate I-8 was dissolved in 0.16 L of tetrahydrofuran (THF) under a nitrogen atmosphere, 12.6 g (48.7 mmol) of 2-chloro-4,6-diphenyl-1,3,5-triazine and 1.63 g (1.41 mmol) of tetrakis(triphenylphosphine)palladium were added thereto, and the mixture was agitated. Then, 16.2 g (117 mmol) of potassium carbonate saturated in water was added thereto, and the obtained mixture was heated and refluxed at 80° C. for 6 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 21.2 g (85%) of the compound 6.

HRMS (70 eV, EI+): m/z calcd for $C_{36}H_{25}N_3S$: 531.1769. found: 531.

Elemental Analysis: C, 81%; H, 5%

Example 7

Synthesis of Compound 9

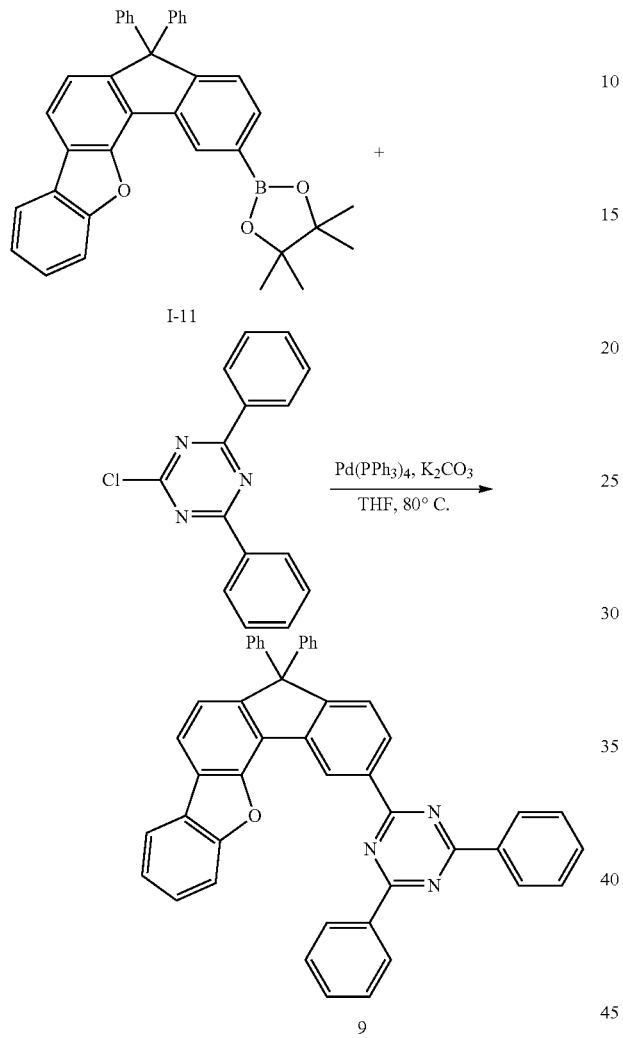

20 g (37.4 mmol) of the intermediate I-11 was dissolved in 0.15 L of tetrahydrofuran (THF) under a nitrogen atmosphere, 10.0 g (37.4 mmol) of 2-chloro-4,6-diphenyl-1,3,5-triazine and 1.30 g (1.12 mmol) of tetrakis(triphenylphosphine)palladium were added thereto, and the mixture was agitated. Then, 12.9 g (93.5 mmol) of potassium carbonate was added thereto, and the obtained mixture was heated and refluxed at 80° C. for 11 hours. When the reaction was complete, water was added to the reaction solution, and the mixture was extracted with dichloromethane (DCM) and treated with anhydrous MgSO$_4$ to remove moisture and then, filtered and concentrated under a reduced pressure. Then, a residue obtained therefrom was separated and purified through flash column chromatography, obtaining 19.4 g (81%) of the compound 9.

HRMS (70 eV, EI+): m/z calcd for C46H29N3O: 639.2311. found: 639.

Elemental Analysis: C, 86%; H, 5%

Example 8

Synthesis of Compound 27

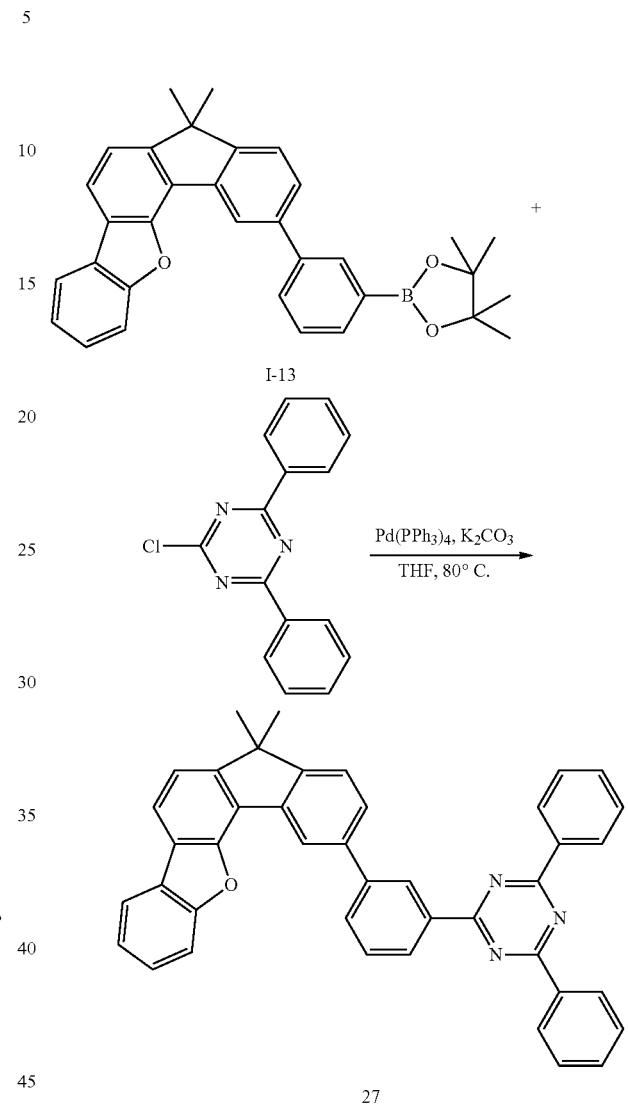

20 g (41.1 mmol) of the intermediate I-13 was dissolved in 0.16 L of tetrahydrofuran (THF) under a nitrogen atmosphere, 12.6 g (48.7 mmol) of 2-chloro-4,6-diphenyl-1,3,5-triazine and 1.42 g (1.46 mmol) of tetrakis(triphenylphosphine)palladium were added thereto, and the mixture was agitated. Then, 14.2 g (103 mmol) of potassium carbonate saturated in water was added thereto, and the obtained mixture was heated and refluxed at 80° C. for 8 hours. When the reaction was complete, water was added to the reaction solution, and the mixture was extracted with dichloromethane (DCM) and treated with anhydrous MgSO$_4$ to remove moisture and then, filtered and concentrated under a reduced pressure. Then, a residue obtained therefrom was separated and purified through flash column chromatography, obtaining 20.2 g (83%) of the compound 27.

HRMS (70 eV, EI+): m/z calcd for C42H29N3O: 591.2311. found: 591.

Elemental Analysis: C, 85%; H, 5%

Example 9

Synthesis of Compound 33

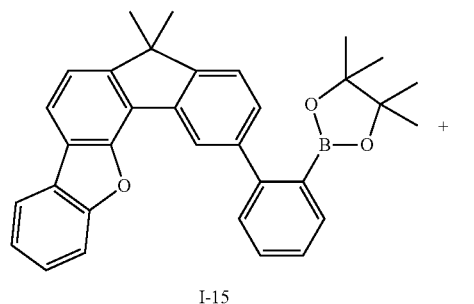

I-15

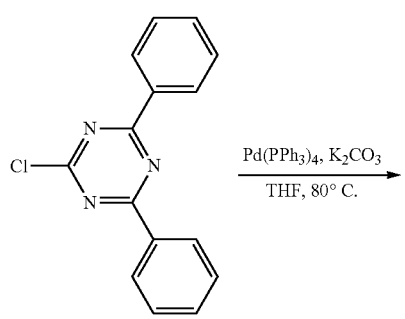

Pd(PPh₃)₄, K₂CO₃
THF, 80° C.

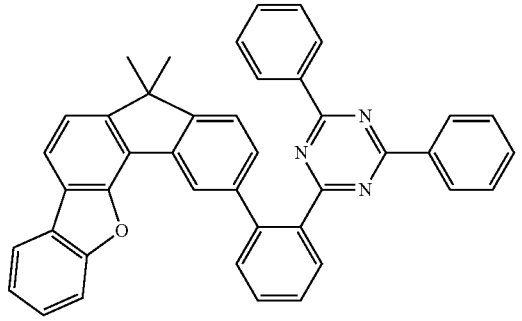

33

20 g (41.1 mmol) of the intermediate I-15 was dissolved in 0.16 L of tetrahydrofuran (THF) under a nitrogen atmosphere, 11.0 g (41.1 mmol) of 2-chloro-4,6-diphenyl-1,3,5-triazine and 1.42 g (1.46 mmol) of tetrakis(triphenylphosphine)palladium were added thereto, and the mixture was agitated. Then, 14.2 g (103 mmol) of potassium carbonate saturated in water was added thereto, and the obtained mixture was heated and refluxed at 80° C. for 8 hours. When the reaction was complete, water was added to the reaction solution, and the mixture was extracted with dichloromethane (DCM) and treated with anhydrous MgSO₄ to remove moisture and then, filtered and concentrated under a reduced pressure. Then, a residue obtained therefrom was separated and purified through flash column chromatography, obtaining 16.3 g (67%) of the compound 33.

HRMS (70 eV, EI+): m/z calcd for C42H29N3O: 591.2311. found: 591.

Elemental Analysis: C, 85%; H, 5%

Example 10

Synthesis of Compound 45

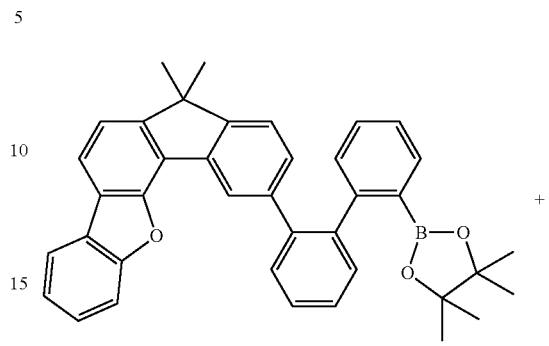

I-17

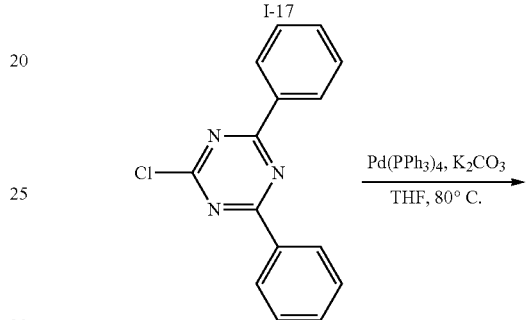

Pd(PPh₃)₄, K₂CO₃
THF, 80° C.

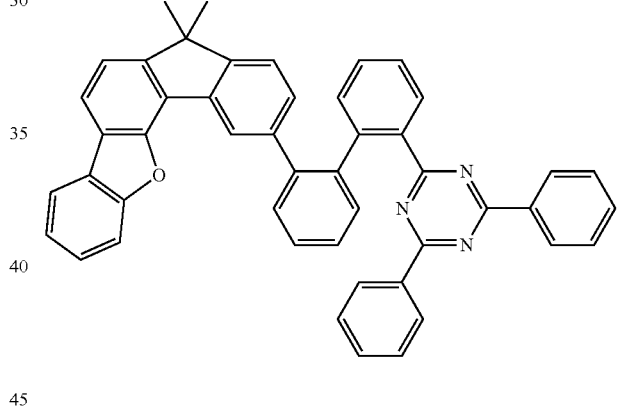

45

3 g (4.49 mmol) of the intermediate I-17 was dissolved in 0.16 L of tetrahydrofuran (THF) under a nitrogen atmosphere, 1.20 g (4.49 mmol) of 2-chloro-4,6-diphenyl-1,3,5-triazine and 0.16 g (0.13 mmol) of tetrakis(triphenylphosphine)palladium were added thereto, and the mixture was agitated. Then, 1.55 g (11.2 mmol) of potassium carbonate saturated in water was added thereto, and the obtained mixture was heated and refluxed at 80° C. for 15 hours. When the reaction was complete, water was added to the reaction solution, and the mixture was extracted with dichloromethane (DCM) and treated with anhydrous MgSO₄ to remove moisture and then, filtered and concentrated under a reduced pressure. Then, a residue obtained therefrom was separated and purified through flash column chromatography, obtaining 1.83 g (61%) of the compound 45.

HRMS (70 eV, EI+): m/z calcd for C48H33N3O: 667.2624. found: 667.

Elemental Analysis: C, 86%; H, 5%

Example 11

Synthesis of Compound 60

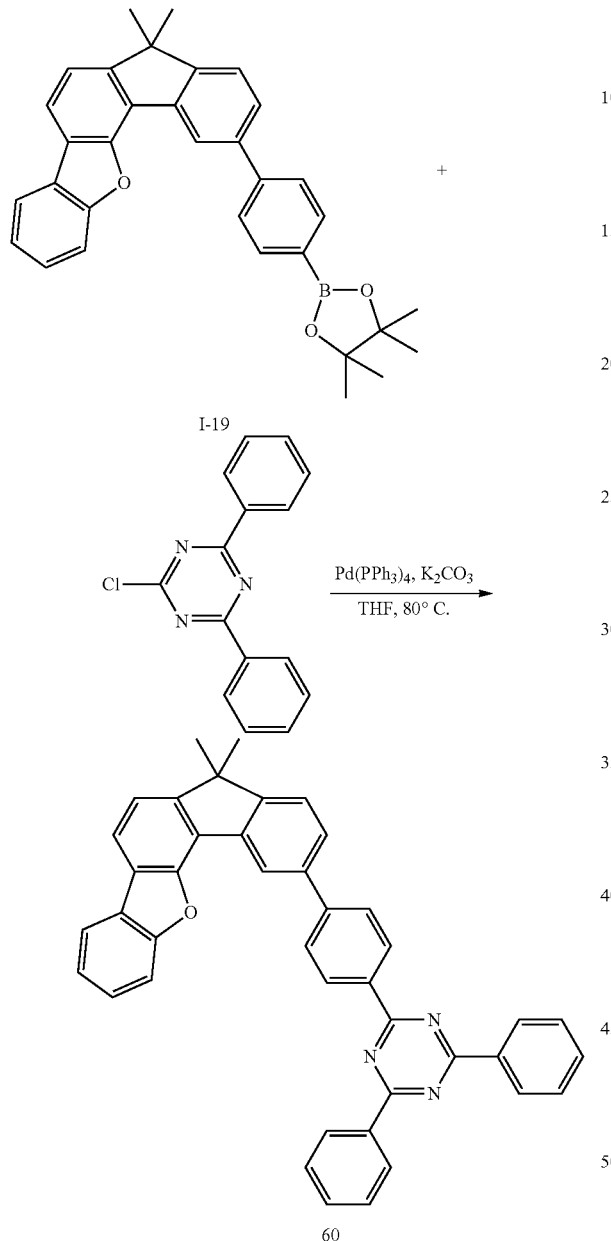

20 g (41.1 mmol) of the intermediate I-19 was dissolved in 0.16 L of tetrahydrofuran (THF) under a nitrogen atmosphere, 11.0 g (41.1 mmol) of 2-chloro-4,6-diphenyl-1,3,5-triazine and 1.42 g (1.46 mmol) of tetrakis(triphenylphosphine)palladium were added thereto, and the mixture was agitated. Then, 14.2 g (103 mmol) of potassium carbonate saturated in water was added thereto, and the obtained mixture was heated and refluxed at 80° C. for 8 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 23.1 g (95%) of the compound 60.

HRMS (70 eV, EI+): m/z calcd for C42H29N3O: 591.2311. found: 591.

Elemental Analysis: C, 85%; H, 5%

Example 12

Synthesis of Compound HT1

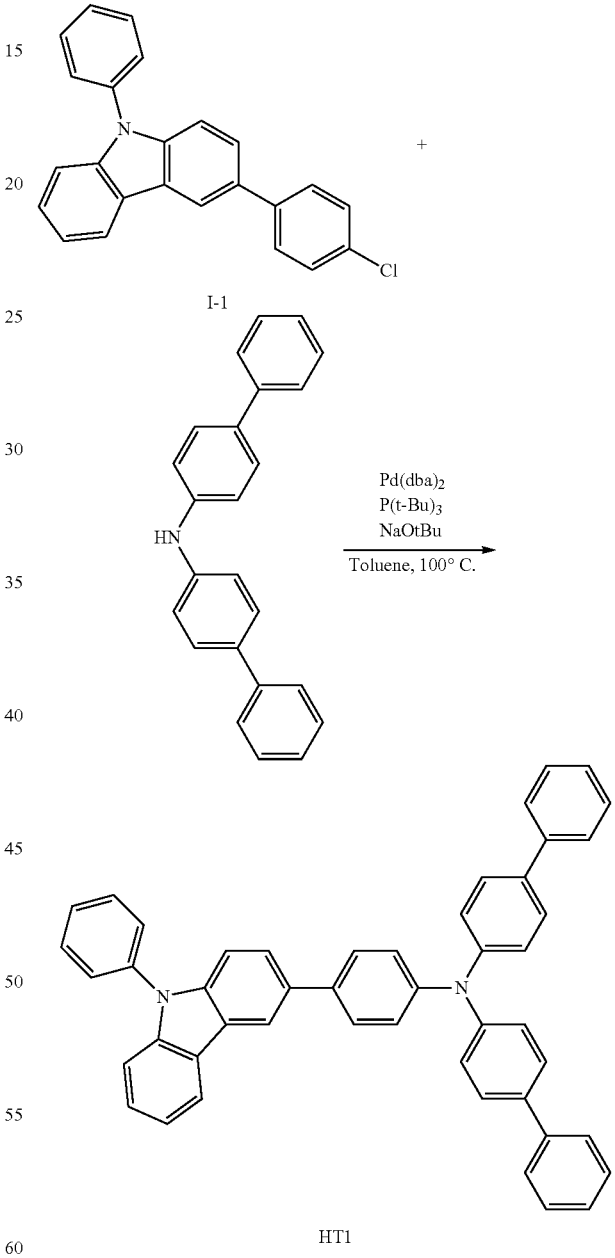

20 g (56.5 mmol) of the intermediate I-1 was dissolved in 0.2 L of toluene under a nitrogen atmosphere, 18.2 g (56.5 mmol) of dibiphenyl-4-ylamine made by Shenzhen gre-syn chemical technology (http://www.gre-syn.com/), 0.33 g (0.57 mmol) of bis(dibenzylideneacetone)palladium (o), 0.58 g (2.83 mmol) of tris-tert butylphosphine and 6.52 g (67.8 mmol) of sodium tert-butoxide were sequentially added thereto, and the mixture was heated and refluxed at 100° C. for 15 hours. When the reaction was complete, water was added to the reaction solution, and the mixture was extracted with dichloromethane (DCM) and treated with anhydrous $MgSO_4$ to remove moisture and then, filtered and concentrated under a reduced pressure. Then, a residue obtained therefrom was separated and purified through flash column chromatography, obtaining 32.5 g (90%) of the compound HT1.

HRMS (70 eV, EI+): m/z calcd for C48H34N2: 638.2722. found: 638.

Elemental Analysis: C, 90%; H, 5%

Manufacture of Organic Light Emitting Diode

Example 13

An organic light emitting diode was manufactured by using the compound 1 according to Example 1 as a host and Ir(PPy)$_3$ as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of sheet resistance into a size of 50 mm×50 mm×0.7 mm, ultrasonic wave-cleaning them in acetone, isopropylalcohol, and pure water for 15 minutes respectively, and UV ozone cleaning them for 30 minutes. On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) under a vacuum degree 650×10$^{-7}$ Pa at a deposition rate of 0.1 to 0.3 nm/s. Subsequently, A 300 Å-thick emission layer was formed by using the compound 1 of Example 1 under the same vacuum deposition condition, and herein, a phosphorescent dopant of Ir(PPy)$_3$ was simultaneously deposited. Herein, the phosphorescent dopant was deposited to be 7 wt % based on 100 wt % of the total weight of the emission layer by adjusting the deposition rate. On the emission layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer was formed by depositing Alq3 under the same vacuum deposition condition. On the electron transport layer, a cathode is formed by sequentially depositing LiF and Al, manufacturing an organic photoelectric device. The organic light emitting diode has a structure of ITO/NPB (80 nm)/EML (compound1 (93 wt %)+Ir(PPy)3 (7 wt %), 30 nm)/Balq (5 nm)/Alq3 (20 nm)/LiF (1 nm)/Al (100 nm).

Example 14

An organic light emitting diode was manufactured according to the same method as Example 13 except for using the compound 2 according to Example 2 instead of the compound 1 according to Example 1.

Example 15

An organic light emitting diode was manufactured according to the same method as Example 13 except for using the compound 3 according to Example 3 instead of the compound 1 according to Example 1.

Example 16

An organic light emitting diode was manufactured according to the same method as Example 13 except for using the compound 4 according to Example 4 instead of the compound 1 according to Example 1.

Example 17

An organic light emitting diode was manufactured according to the same method as Example 13 except for using the compound 5 according to Example 5 instead of the compound 1 according to Example 1.

Example 18

An organic light emitting diode was manufactured according to the same method as Example 13 except for using the compound 6 according to Example 6 instead of the compound 1 according to Example 1.

Example 19

An organic light emitting diode was manufactured according to the same method as Example 13 except for using the compound 9 according to Example 7 instead of the compound 1 according to Example 1.

Example 20

An organic light emitting diode was manufactured according to the same method as Example 13 except for using the compound 27 according to Example 8 instead of the compound 1 according to Example 1.

Example 21

An organic light emitting diode was manufactured according to the same method as Example 13 except for using the compound 33 according to Example 9 instead of the compound 1 according to Example 1.

Example 22

An organic light emitting diode was manufactured according to the same method as Example 13 except for using the compound 45 according to Example 10 instead of the compound 1 according to Example 1.

Example 23

An organic light emitting diode was manufactured according to the same method as Example 13 except for using the compound 60 according to Example 11 instead of the compound 1 according to Example 1.

Comparative Example 1

An organic light emitting diode was manufactured according to the same method as Example 13 except for using CBP instead of the compound 1 according to Example 1. The CBP has the following structure.

Comparative Example 2

An organic light emitting diode was manufactured according to the same method as Example 13 except for using HOST1 instead of the compound 1 according to Example 1. The HOST1 has the following structure.

Comparative Example 3

An organic light emitting diode was manufactured according to the same method as Example 13 except for using HOST2 instead of the compound 1 according to Example 1. The HOST2 has the following structure.

The structures of NPB, BAlq, CBP, Ir(PPy)3, HOST1 and HOST2 used to manufacture the organic light emitting diodes are as follows.

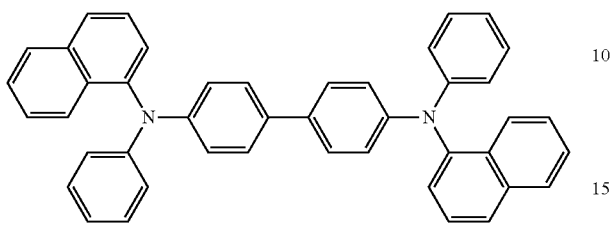

[NPB]

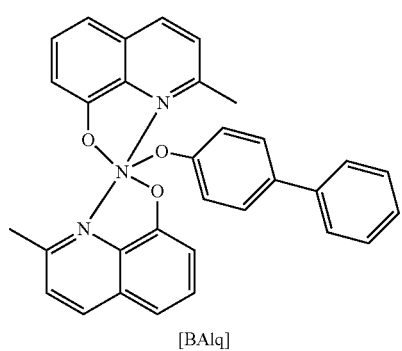

[BAlq]

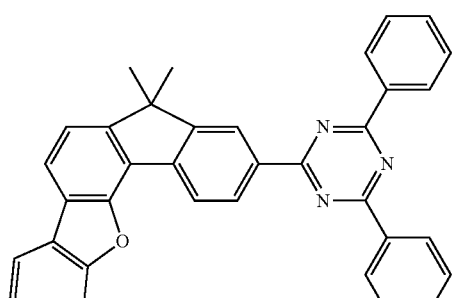

[HOST1]

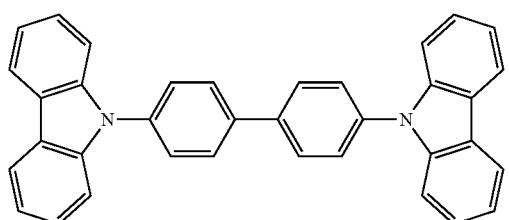

[CBP]

-continued

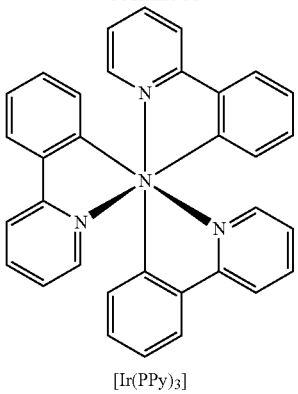

[Ir(PPy)3]

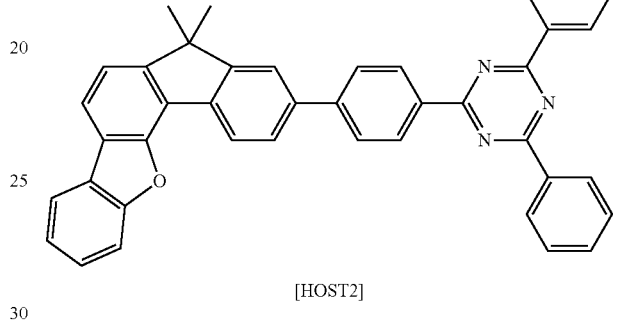

[HOST2]

Example 24

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor.

This obtained ITO transparent electrode was used as a anode, and a 600 Å-thick hole injection layer was formed by vacuum-depositing 4,4'-bis[N-[4-{N,N-bis(3-methylphenyl)amino}-phenyl]-N-phenylamino]biphenyl (DNTPD) on the ITO substrate. Subsequently, a 300 Å-thick hole transport layer was formed by vacuum-depositing HT1 synthesize in Example 12.

On the hole transport layer, 9,10-di-2-naphthyl)anthracene (AND) as a host doped with 3 wt % of 2,5,8,11-tetra(tert-butyl)perylene (TBPe) as a dopant to form a 250 Å-thick emission layer. Then, the compound 27 synthesized in Example 8 was vacuum-deposited on the emission layer to form a 50 Å-thick electron transport auxiliary layer. Then, Alq3 was vacuum-deposited thereon to form a 250 Å-thick electron transport layer. LiF 10 Å and Al 1000 Å were sequentially vacuum-deposited on the electron transport layer to form a cathode, manufacturing an organic light emitting diode.

The organic light emitting diode had a five-layered organic thin film structure and specifically, Al (1000 Å)/LiF 10 Å/Alq3 250 Å/electron transportauxiliary layer 50 Å/EML [AND:TBPe=97: 3]250 Å/hole transport layer 300 Å/DNTPD 600 Å/ITO (1500 Å).

Example 25

An organic light emitting diode was manufactured according to the same method as Example 24, except for using the compound 33 synthesized in Example 9 for an electron transport auxiliary layer, instead of the compound 27 synthesized in Example 8.

Example 26

An organic light emitting diode was manufactured according to the same method as Example 24, except for using the compound 45 synthesized in Example 10 for an electron transport auxiliary layer, instead of the compound 27 synthesized in Example 8.

Comparative Example 4

An organic light emitting diode was manufactured according to the same method as Example 24, except for not using the electron transport auxiliary layer.

Comparative Example 5

An organic light emitting diode was manufactured according to the same method as Example 24, except for using HOST1 for an electron transport auxiliary layer, instead of the compound 27 synthesized in Example 8.

Comparative Example 6

An organic light emitting diode was manufactured according to the same method as Example 24, except for using HOST2 for an electron transport auxiliary layer, instead of the compound 27 synthesized in Example 8.

The structures of the DNTPD, AND, TBPe and NPB used for manufacturing the organic light emitting diode were as follows.

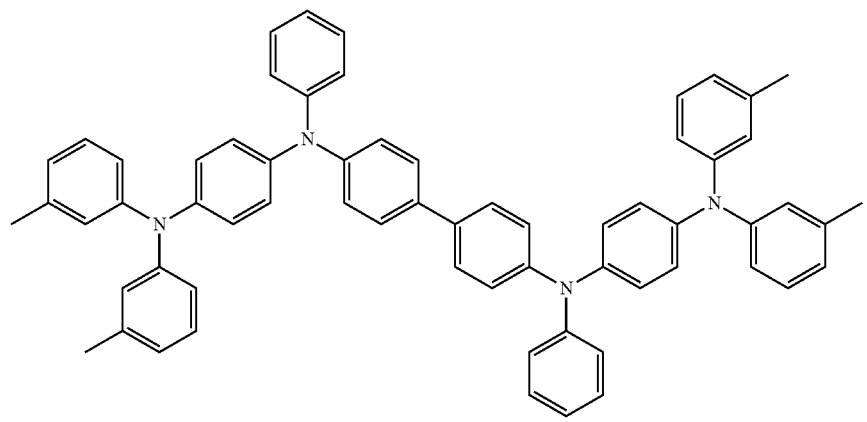

[DNTPD]

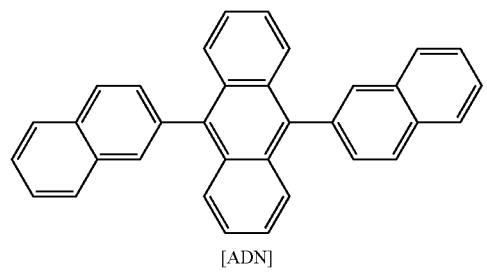

[ADN]

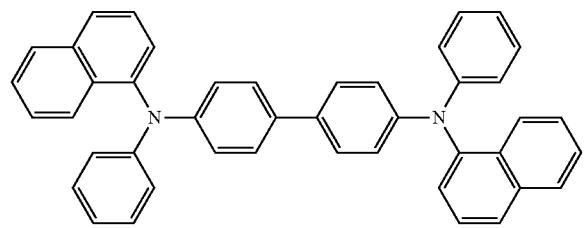

[NPB]

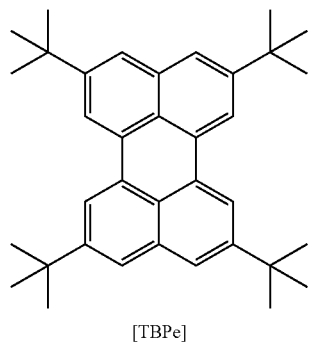

[TBPe]

Evaluation I

Current density and luminance changes depending on a voltage, and luminous efficiency of each organic light emitting diode according to Examples 13 to 23 and Comparative Examples 1 to 3 were measured.

Specific measurement methods were as follow, and the results were provided in Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm2) were calculated by using the luminance, current density, and voltages (V) from the items (1) and (2).

(4) Life-Span

Life-span was obtained by measuring time taken until current efficiency (cd/A) decreased while luminance (cd/m$^2$) was maintained at 5000 cd/m$^2$.

TABLE 1

| Devices | Compound used for host | Driving voltage (V) | Colore (EL color) | Efficiency (cd/A) | 90% life-span(h) @5000 cd/m$^2$ |
|---|---|---|---|---|---|
| Example 13 | compound 1 | 4.1 | Green | 53.5 | 140 |
| Example 14 | compound 2 | 4.2 | Green | 55.2 | 140 |
| Example 15 | compound 3 | 3.9 | Green | 58.3 | 170 |
| Example 16 | compound 4 | 3.8 | Green | 55.3 | 130 |
| Example 17 | compound 5 | 3.8 | Green | 60.0 | 120 |
| Example 18 | compound 6 | 3.6 | Green | 61.1 | 150 |
| Example 19 | compound 9 | 3.9 | Green | 58.2 | 200 |
| Example 20 | compound 27 | 4.0 | Green | 53.8 | 550 |
| Example 21 | compound 33 | 3.9 | Green | 55.0 | 620 |
| Example 22 | compound 45 | 4.5 | Green | 51.6 | 1,100 |
| Example 23 | compound 60 | 4.0 | Green | 50.0 | 480 |
| Comparative Example 1 | CBP | 4.8 | Green | 31.4 | 40 |
| Comparative Example 2 | HOST1 | 3.8 | Green | 55.0 | 50 |
| Comparative Example 3 | HOST2 | 4.0 | Green | 48.1 | 120 |

According to the results of Table 1, the organic light emitting diodes according to Examples 13 to 23 showed remarkably improved life-span characteristics without decrease of luminous efficiency and driving voltage compared with the organic light emitting diodes according to Comparative Example 1 to Comparative Example 3.

Evaluation II

Current density and luminance changes depending on a voltage, and luminous efficiency of each organic light emitting diode according to Examples 24 to 26 and Comparative Examples 4 to 6 were measured.

Specific measurement methods were as follow, and the results were provided in Table 2.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm2) were calculated by using the luminance, current density, and voltages (V) from the items (1) and (2).

(4) Life-Span

Life-span was obtained by measuring time taken until current efficiency (cd/A) decreased to 50% while luminance (cd/m$^2$) was maintained at 1000 cd/m$^2$.

TABLE 2

| Devices | Compound used in electron transport auxiliary layer | Driving voltage (V) | Colore (EL color) | Efficiency (cd/A) | Half-life life-span (h) @ 1000 cd/m$^2$ |
|---|---|---|---|---|---|
| Example 24 | compound 27 | 6.0 | Blue | 7.4 | 1,450 |
| Example 25 | compound 33 | 5.9 | Blue | 7.3 | 1,500 |
| Example 26 | compound 45 | 6.5 | Blue | 8.0 | 1,730 |
| Comparative Example 4 | None | 6.6 | Blue | 5.7 | 1,340 |
| Comparative Example 5 | HOST1 | 6.7 | Blue | 5.8 | 1,100 |
| Comparative Example 6 | HOST2 | 6.5 | Blue | 5.5 | 1,250 |

According to the results of Table 2, the organic light emitting diodes according to Examples 24 to 26 showed lower driving voltage, and higher efficiency and life-span characteristics compared with the organic light emitting diodes according to Comparative Example 4 to Comparative Example 6.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organic compound represented by Chemical Formula 1:

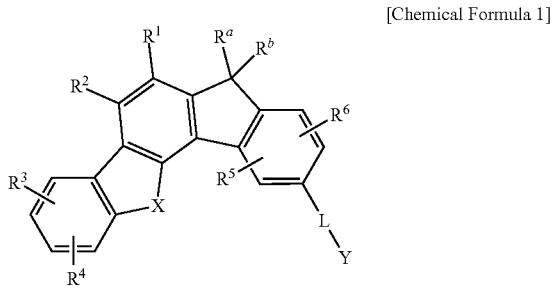

[Chemical Formula 1]

wherein, in Chemical Formula 1,
X is O, S, Se, SO, SO$_2$, PO, or CO,
Y is a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, or a combination thereof,
L is a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, a substituted or unsubstituted C3 to C30 heteroarylene group, a substituted or unsubstituted C6 to C30 aryleneamine group, a substituted or unsubstituted C6 to C30 heteroaryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, R$^a$ and R$^b$ are each independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof, and R$^1$ to R$^6$ are independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthio group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof.

2. The organic compound as claimed in claim 1, wherein the Y is selected from substituted or unsubstituted functional groups listed in Group 1:

[Group 1]

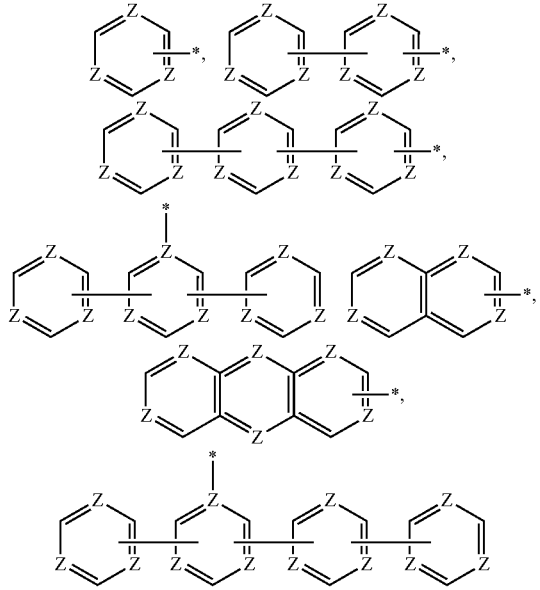

-continued

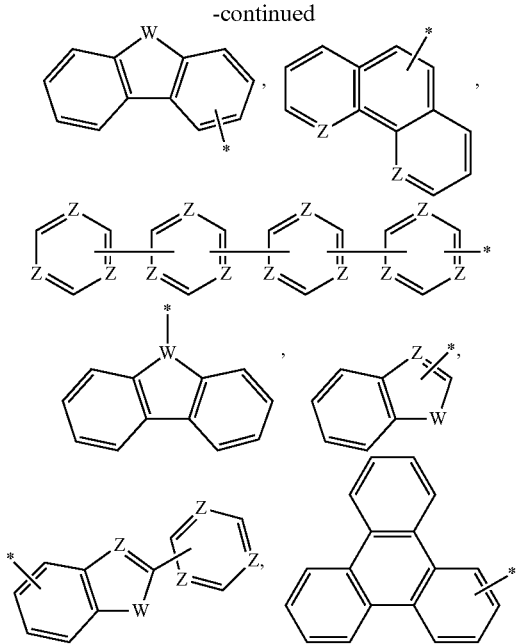

wherein, in Group 1,
W is N, O, S, SO, $SO_2$, $CR^c$, $CR^dR^e$, $SiR^f$, or $SiR^gR^h$,
Z is N, C or $CR^i$,
wherein $R^c$ to $R^i$ are each independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C3 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthio group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and
* is a linking point, and is positioned at one of elements consisting of the functional group.

3. The organic compound as claimed in claim 2, wherein the Y is represented by one of Chemical Formulae A1 to A8:

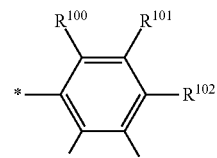
[Chemcial Formula A1]

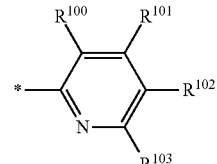
[Chemcial Formula A2]

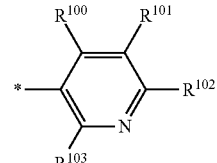
[Chemcial Formula A3]

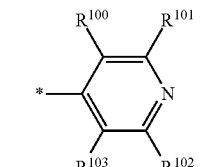
[Chemcial Formula A4]

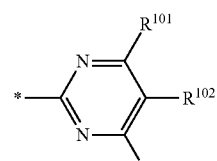
[Chemcial Formula A5]

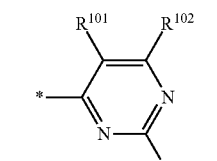
[Chemcial Formula A6]

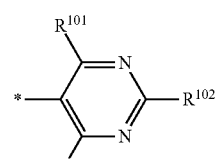
[Chemcial Formula A7]

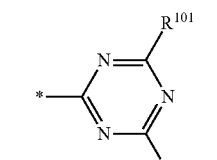
[Chemcial Formula A8]

wherein, in Chemical Formulae A1 to A8,
$R^{100}$ to $R^{104}$ are each independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and
* is a linking point.

4. The organic compound as claimed in claim 2, wherein the Y is represented by one of Chemical Formulae A23 to A32:
[Chemical Formula A23]
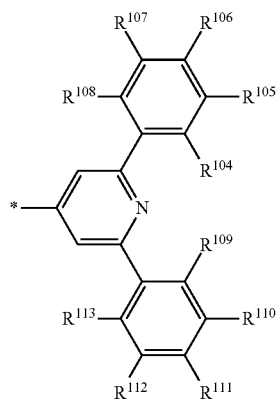
[Chemical Formula A24]
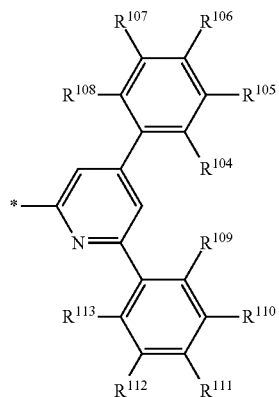
[Chemical Formula A25]
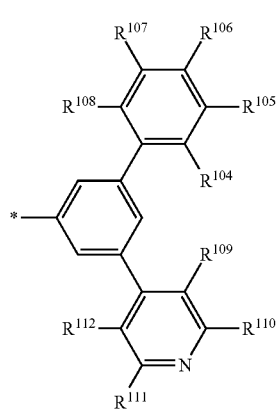
[Chemical Formula A26]
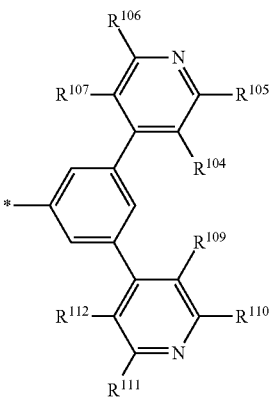
[Chemical Formula A27]
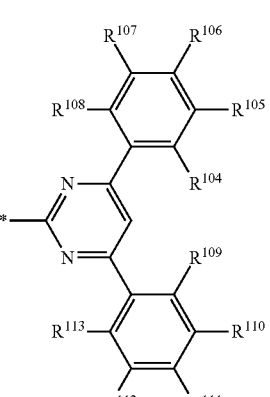
[Chemical Formula A28]
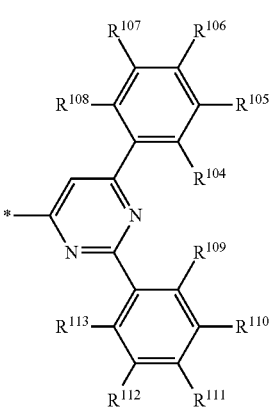
[Chemical Formula A29]
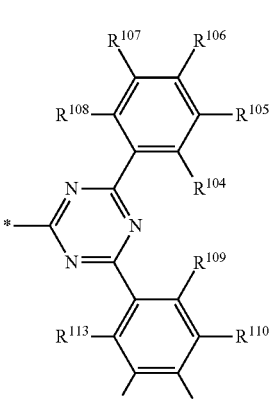

[Chemical Formula A30]

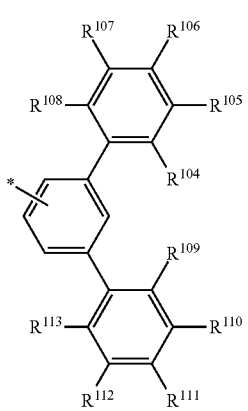

[Chemical Formula A31]

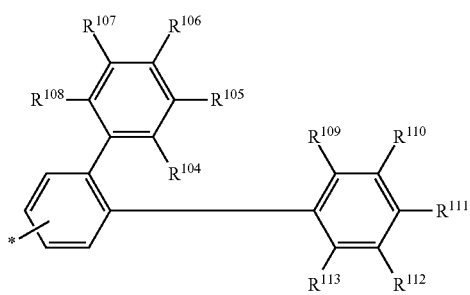

[Chemical Formula A32]

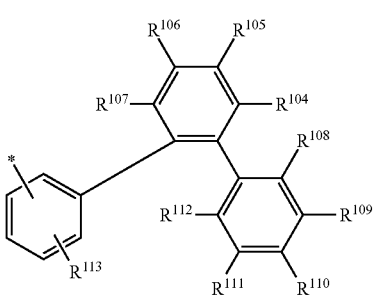

wherein, in Chemical Formulae A23 to A32, $R^{104}$ to $R^{113}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and

* is a linking point.

5. The organic compound as claimed in claim 2, wherein the Y is represented by one of Chemical Formulae A33 to A35:

[Chemical Formula A33]

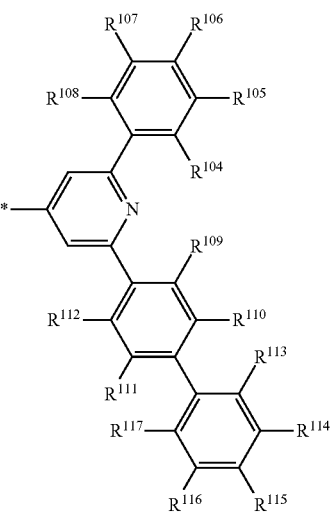

[Chemical Formula A34]

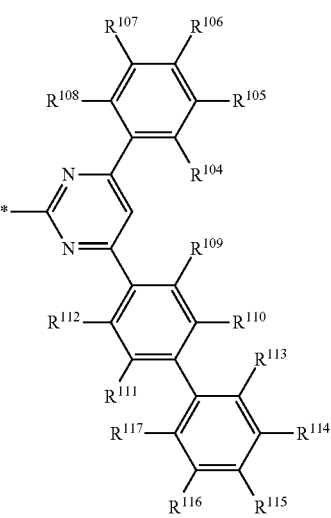

[Chemical Formula A35]

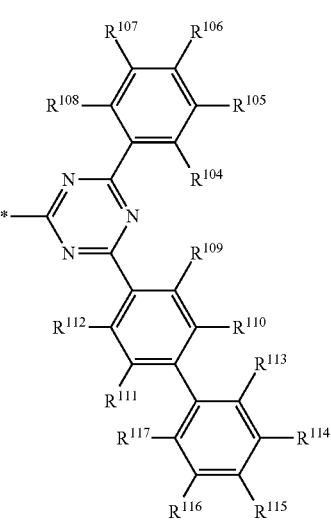

wherein, in Chemical Formulae A33 to A35, $R^{104}$ to $R^{117}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and

* is a linking point.

6. The organic compound as claimed in claim 2, wherein the Y is represented by one of Chemical Formulae A36 to A41:

[Chemical Formula A36]

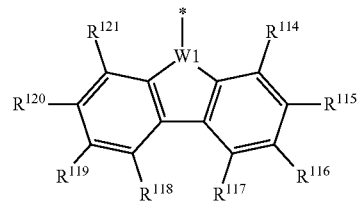

[Chemical Formula A37]

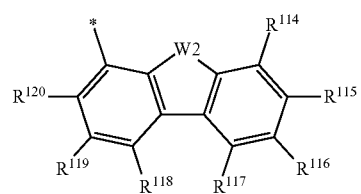

[Chemical Formula A38]

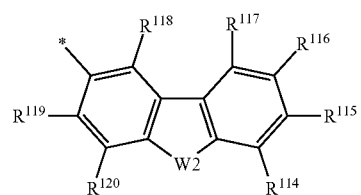

[Chemical Formula A39]

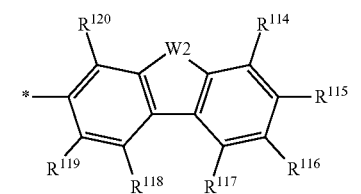

[Chemical Formula A40]

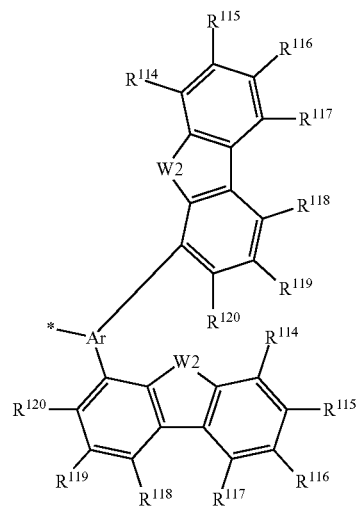

[Chemical Formula A41]

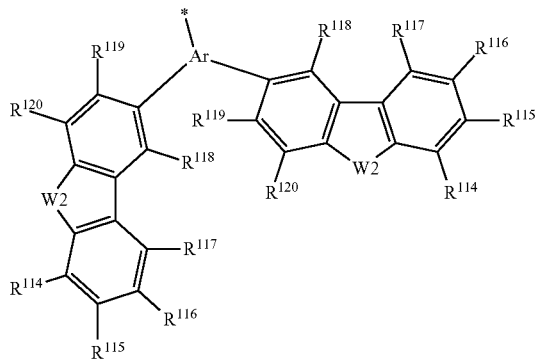

wherein, in Chemical Formulae A36 to A41,

W1 is N, $CR^c$ or $SiR^f$,

W2 is O, S, SO, $SO_2$, $CR^dR^e$ or $SiR^gR^h$,

Ar is a substituted or unsubstituted C6 to C30 arylene group, a substituted or unsubstituted C3 to C30 heteroarylene group, a substituted or unsubstituted C6 to C30 aryleneamine group, a substituted or unsubstituted C6 to C30 heteroaryleneamine group, a substituted or unsubstituted C1 to C30 aryloxylene group, or a combination thereof, $R^{114}$ to $R^{120}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and

* is a linking point.

7. The organic compound as claimed in claim 2, wherein the Y is represented by one of Chemical Formulae A42 to A50:

[Chemical Formula A42]

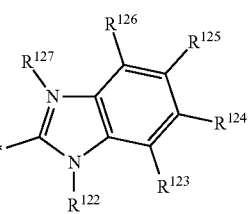

[Chemical Formula A43]

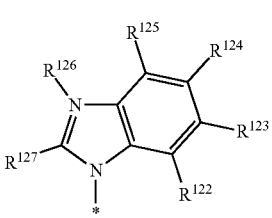

[Chemical Formula A44]

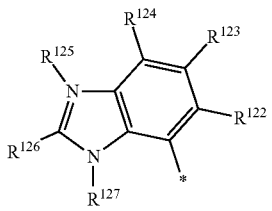

-continued

[Chemical Formula A45]
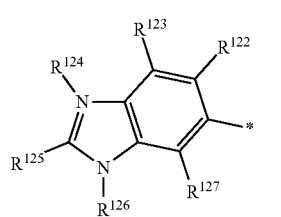

[Chemical Formula A46]
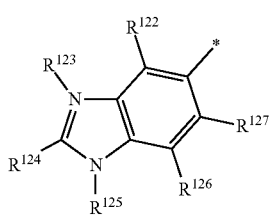

[Chemical Formula A47]
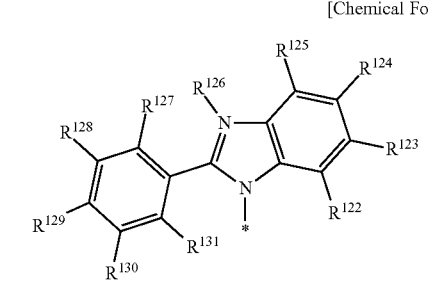

[Chemical Formula A48]
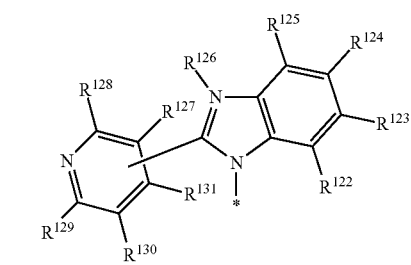

[Chemical Formula A49]
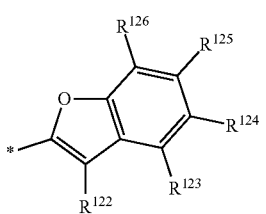

[Chemical Formula A50]
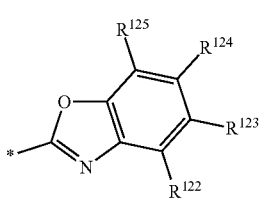

wherein, in Chemical Formulae A42 to A50, $R^{122}$ to $R^{131}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and

* is a linking point.

8. The organic compound as claimed in claim 2, wherein the Y is a substituted or unsubstituted pyridinyl group, a substituted or unsubstituted pyrimidinyl group, a substituted or unsubstituted triazinyl group, a substituted or unsubstituted phenyl group, a substituted or unsubstituted biphenyl group, a substituted or unsubstituted naphthyl group, a substituted or unsubstituted triphenyl group, a substituted or unsubstituted dibenzofuranyl group, a substituted or unsubstituted dibenzothiophenyl group, a substituted or unsubstituted fluorenyl group, a substituted or unsubstituted benzopyridinyl group, a substituted or unsubstituted benzoimidazolyl group or a substituted or unsubstituted benzofuranyl group.

9. The organic compound as claimed in claim 1, wherein the L is a single bond or selected from substituted or unsubstituted linking groups listed in Group 2:

[Group 2]

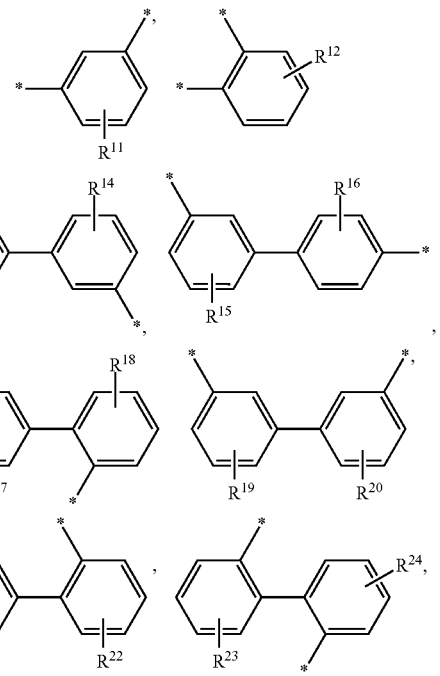

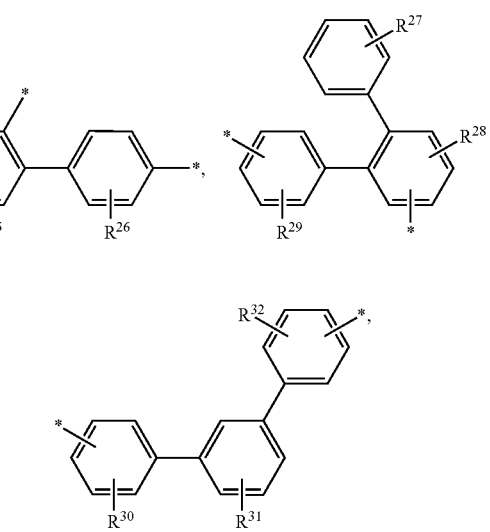

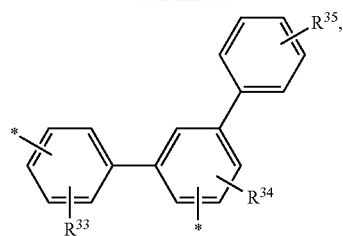

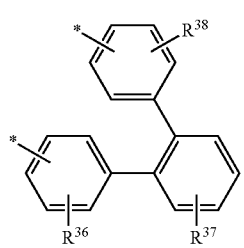

wherein, the $R^{11}$ to $R^{38}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof, and

* is a linking point.

10. The organic compound as claimed in claim 1, which is listed in Group 3:

[Group 3]

1

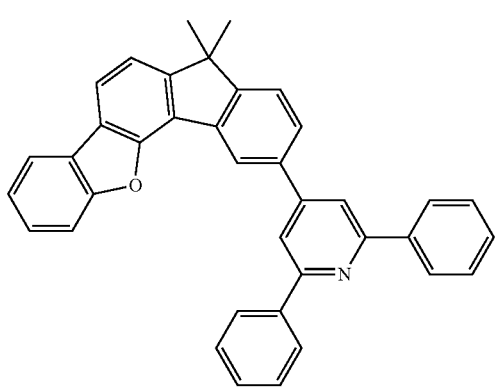

2

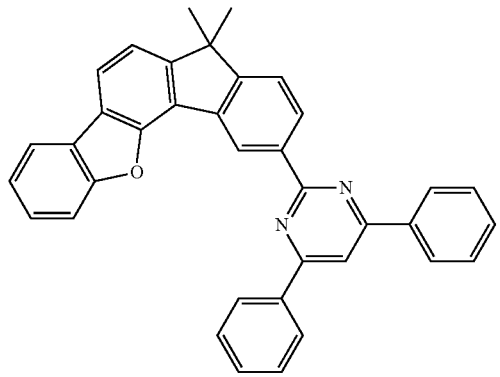

3

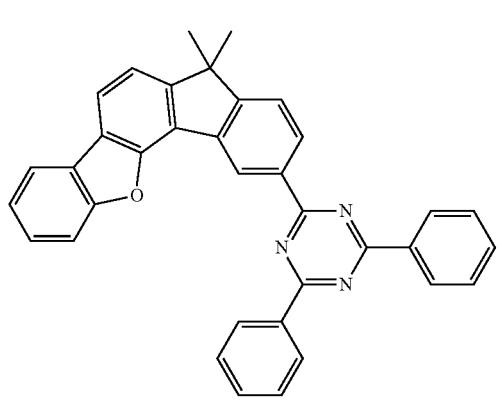

4

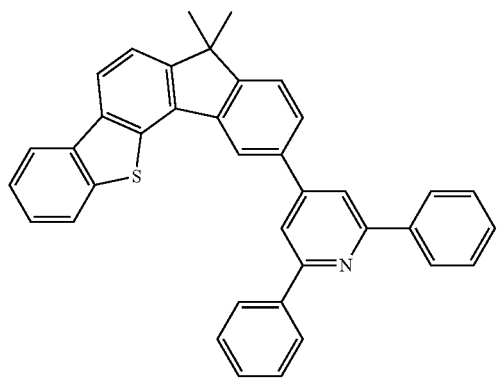

5

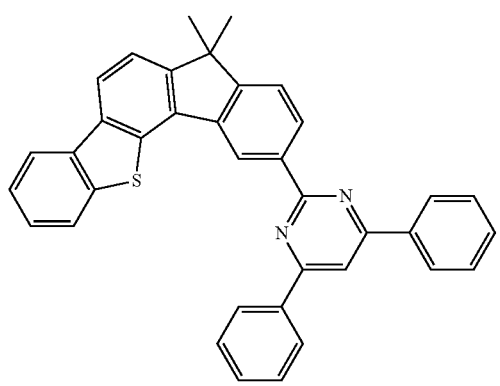

97
-continued
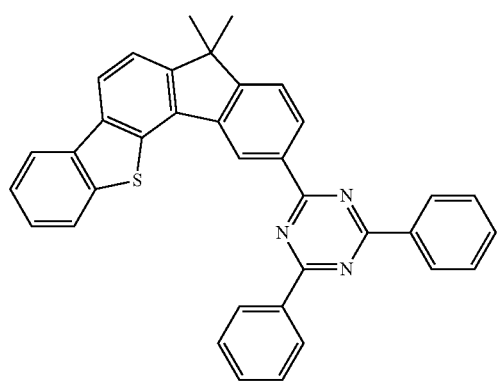
98
-continued
6
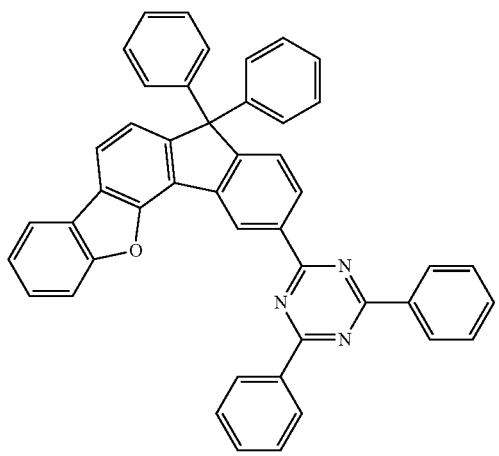
7
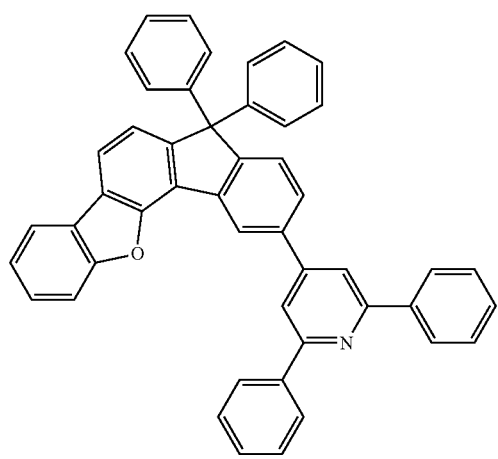
10
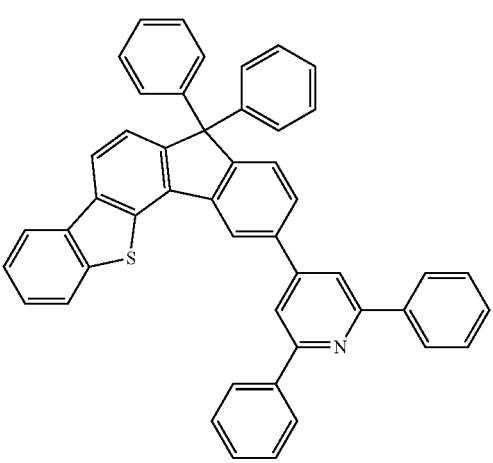
8
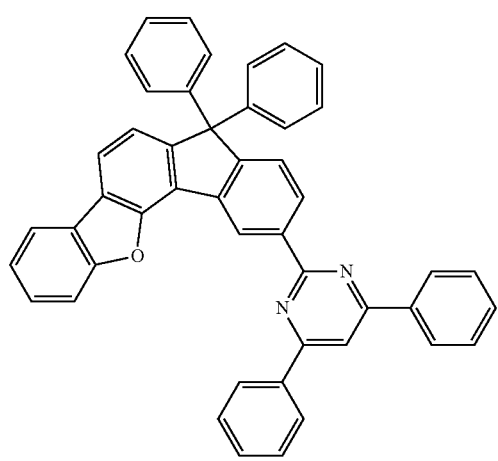
11
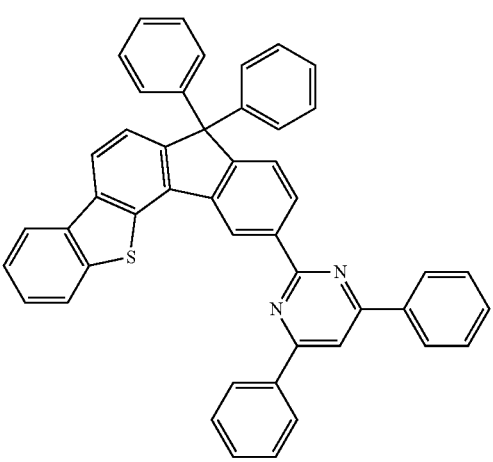

12
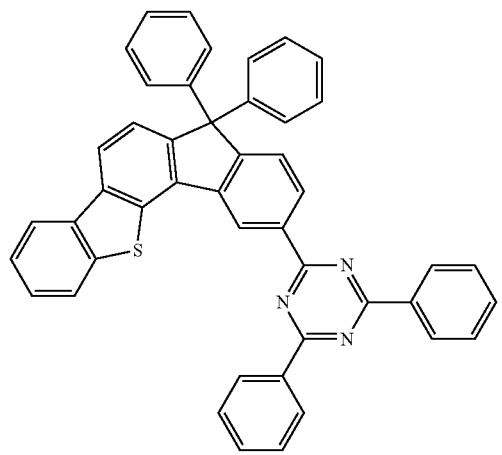
13
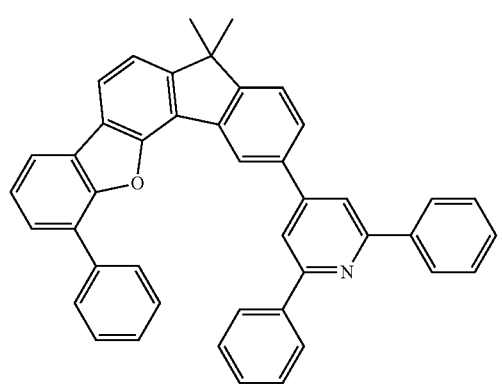
14
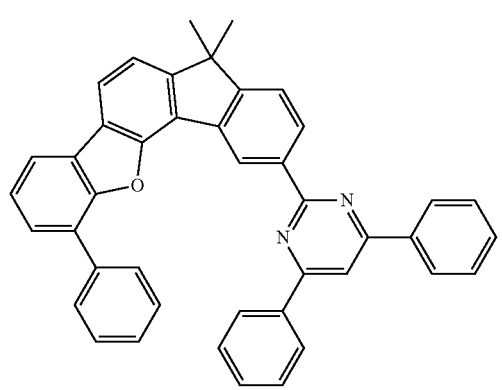
15
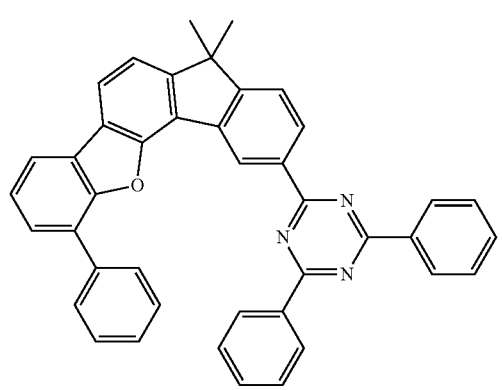
16
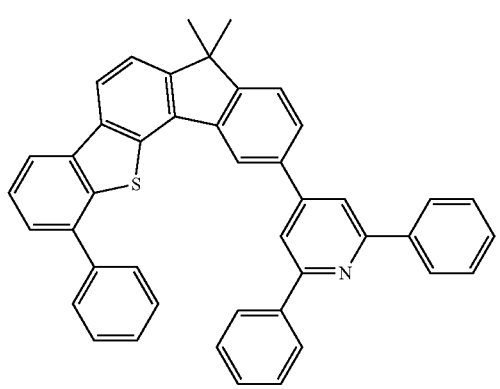
17
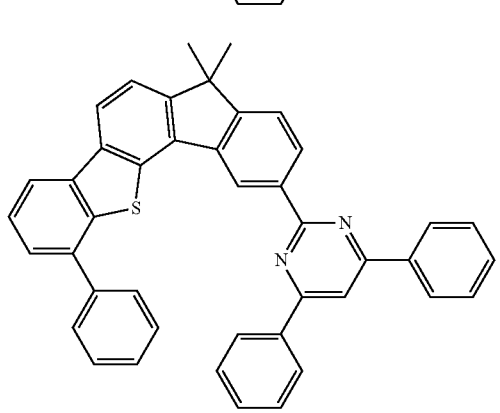
18
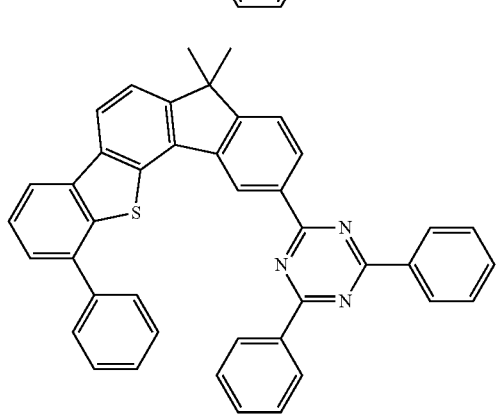
19
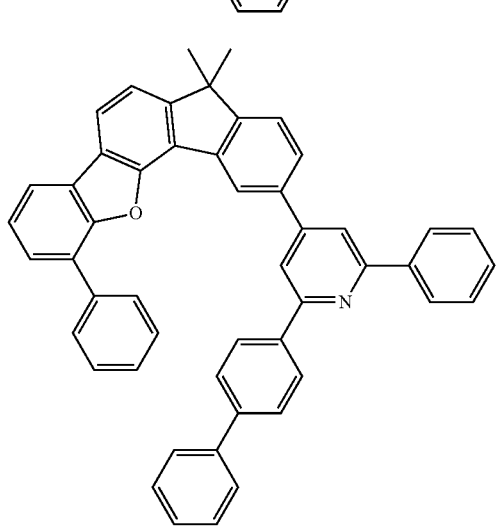

| 101 | 102 |
|---|---|
| -continued | -continued |
| 20 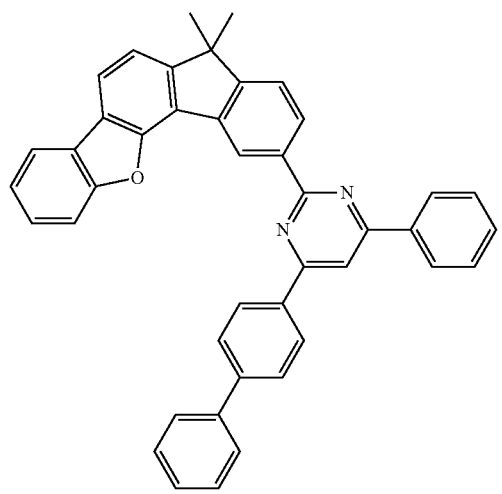 | 23 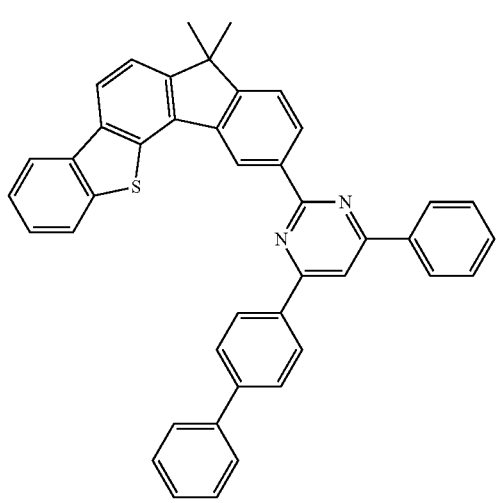 |
| 21 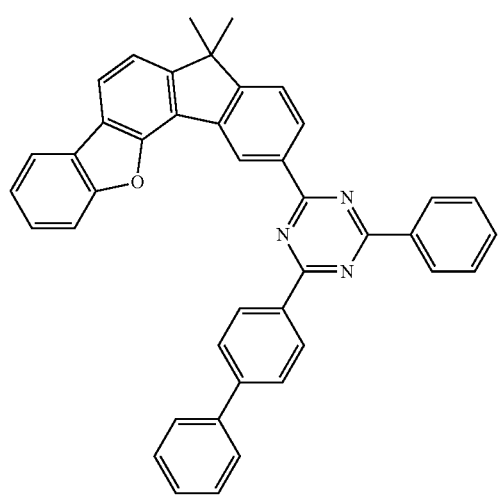 | 24 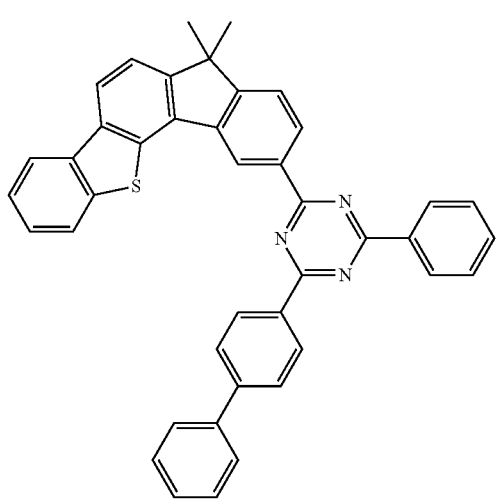 |
| 22 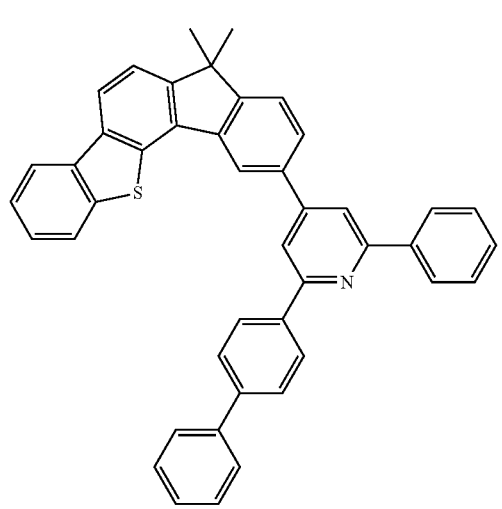 | 25 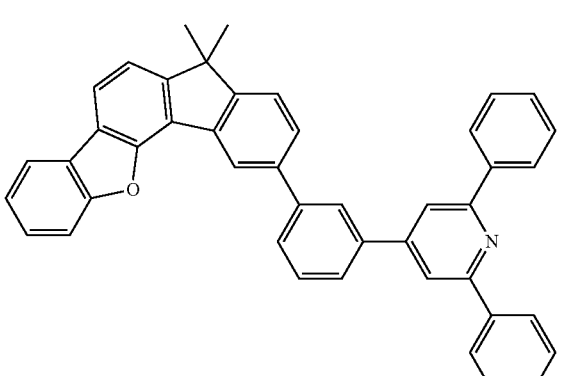 |

26
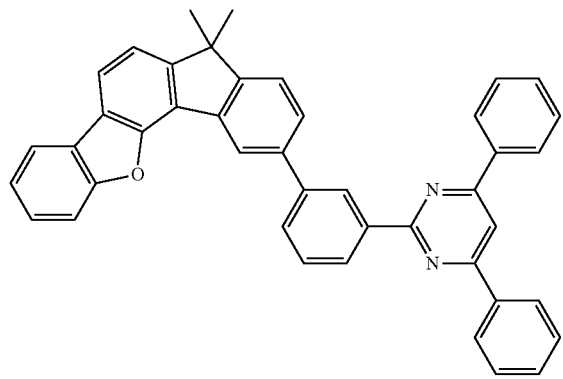
27
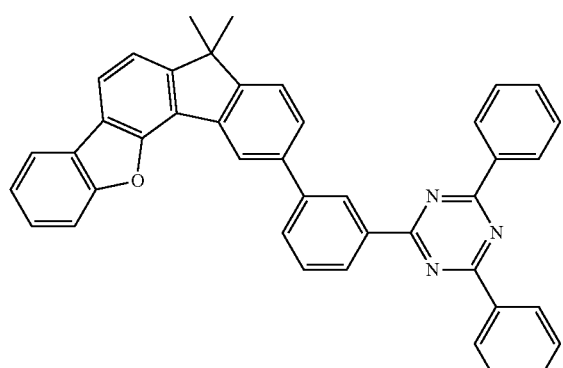
28
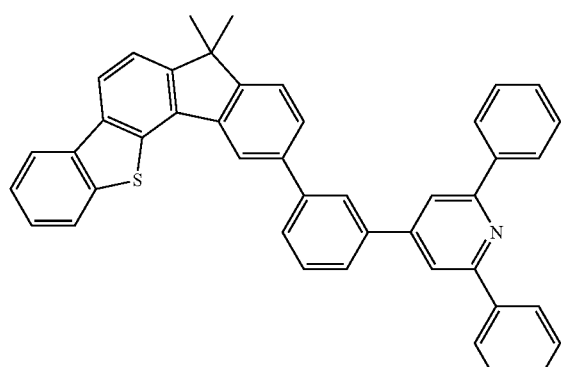
29
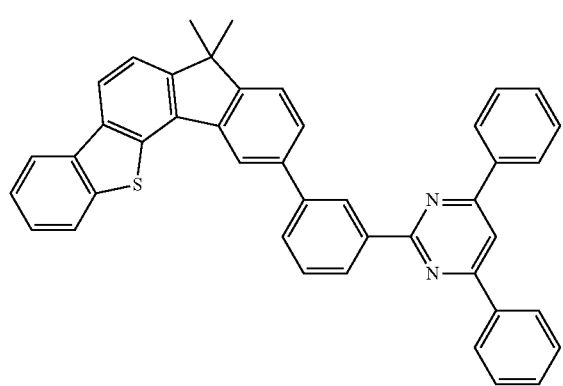
30
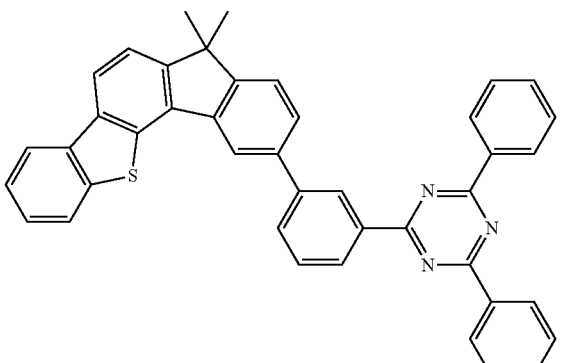
31
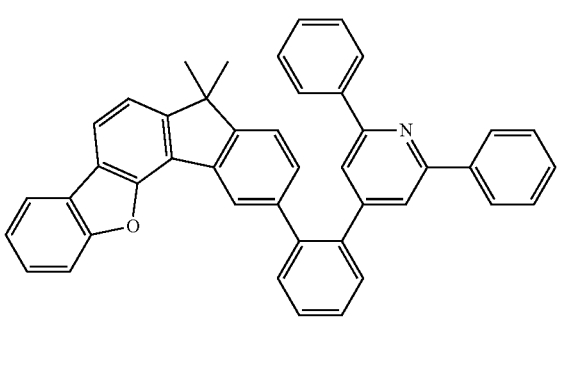
32
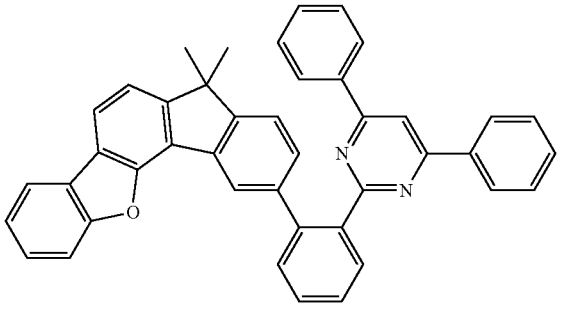
33
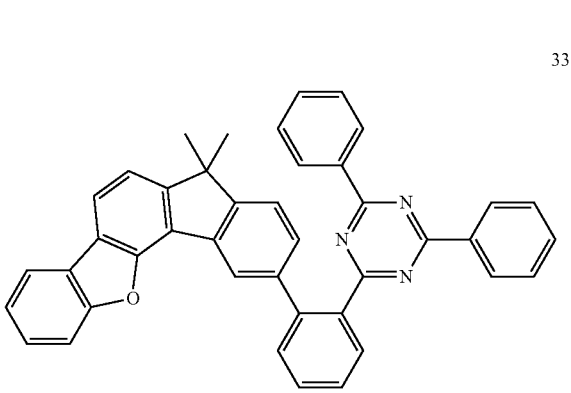

-continued

34

35

36

37

38

-continued

39

40

41

42

43

44
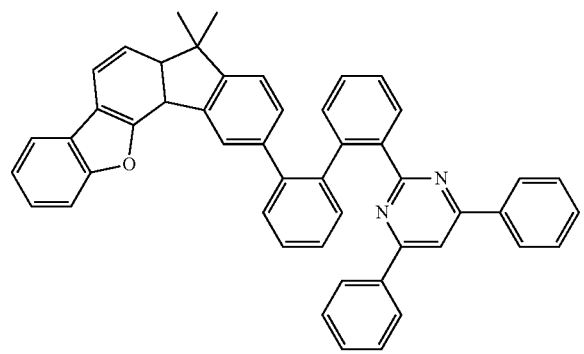
45
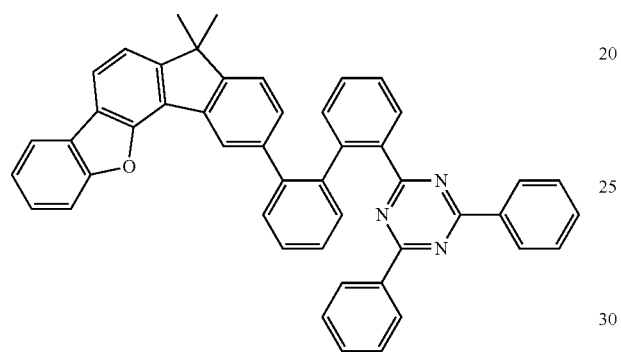
46
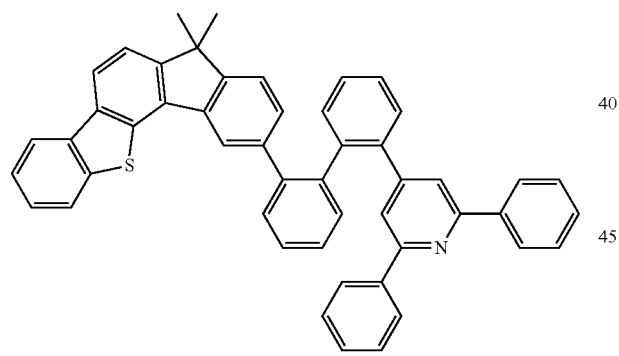
47
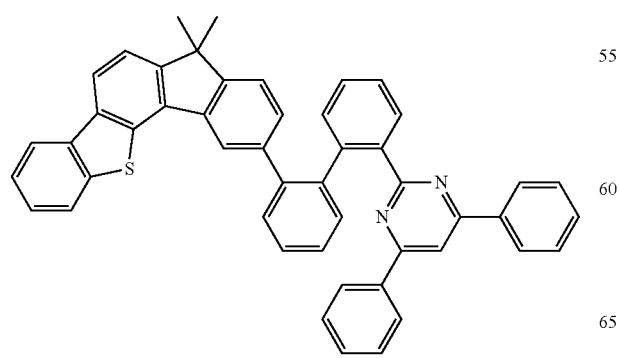
48
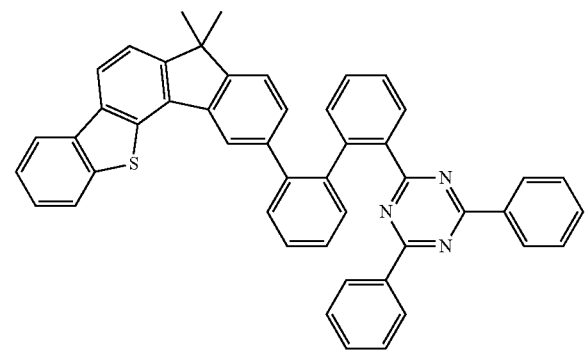
49
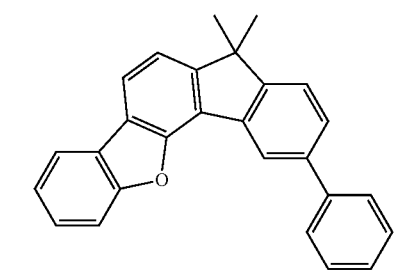
50
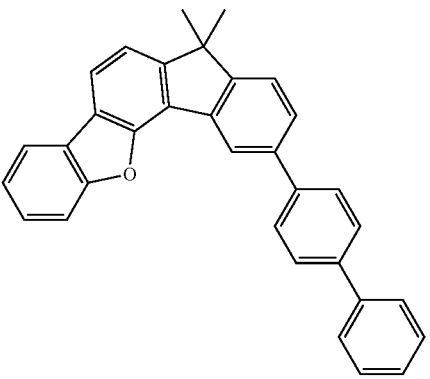
51
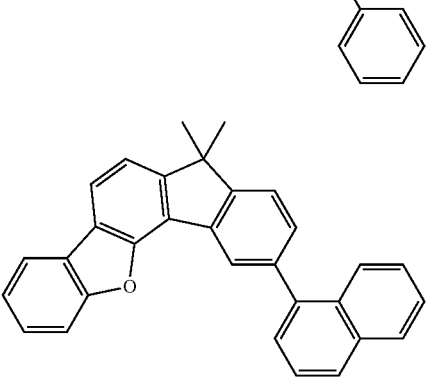
52
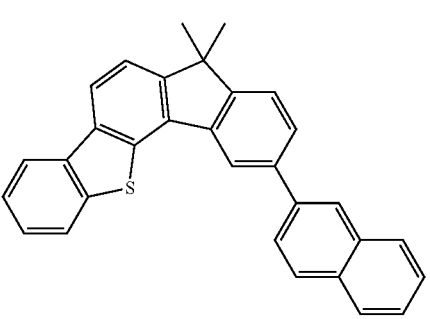

53
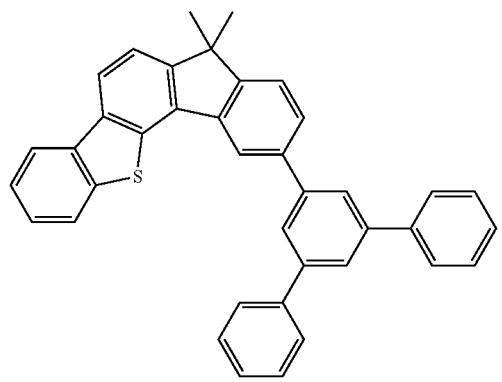
54
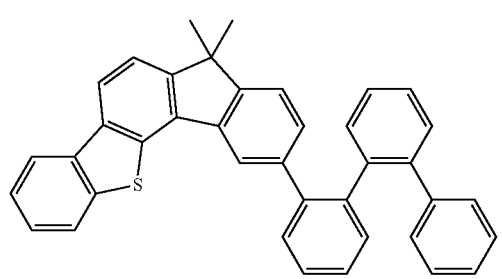
55
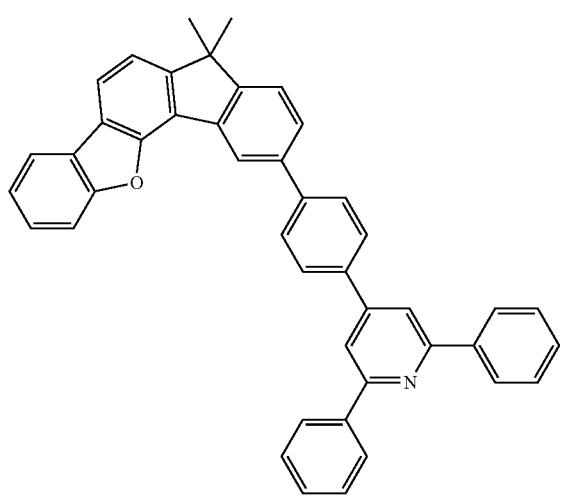
56
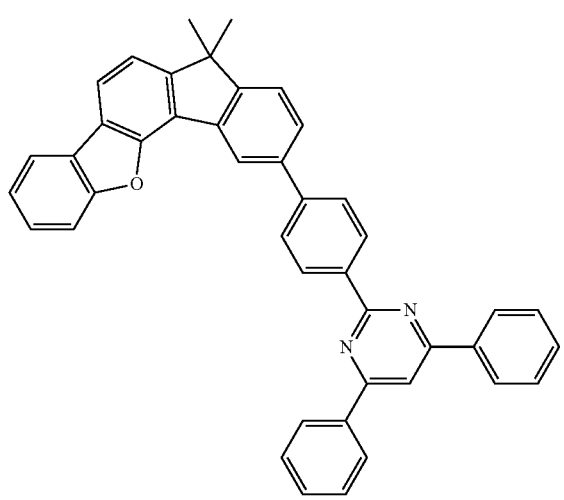
57
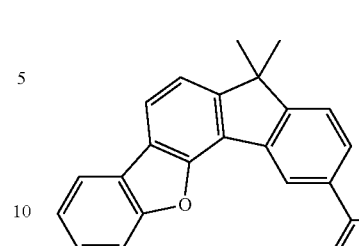
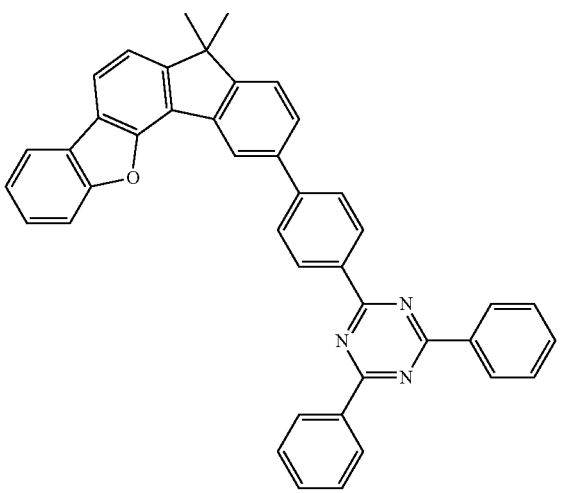
58
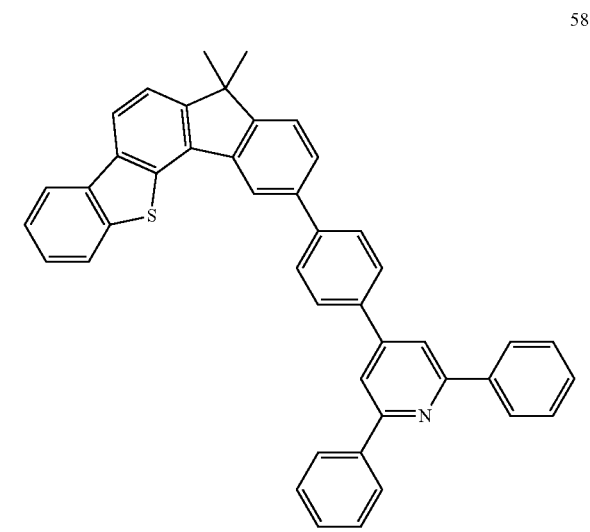
59
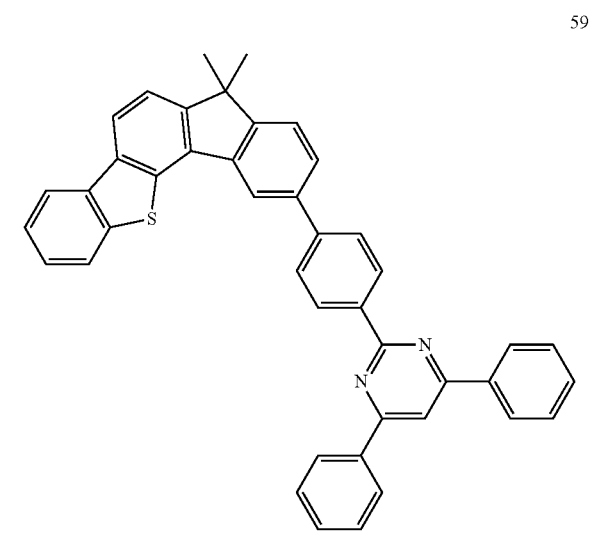

111
-continued
60
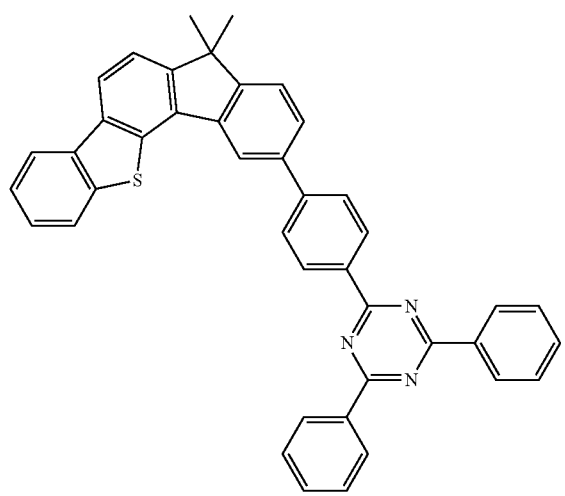
61
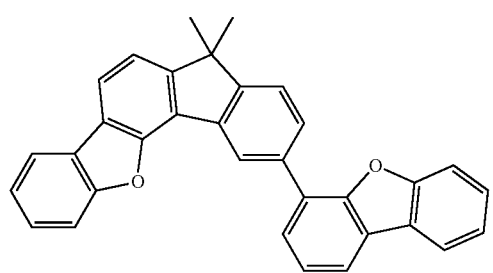
62
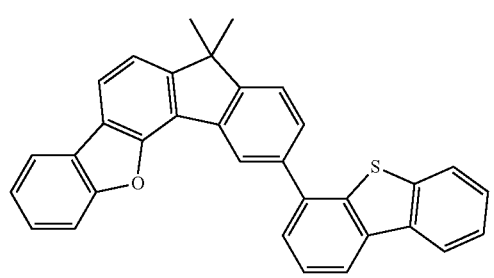
63
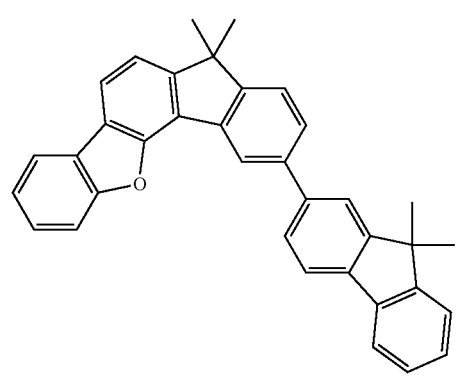
112
-continued
64
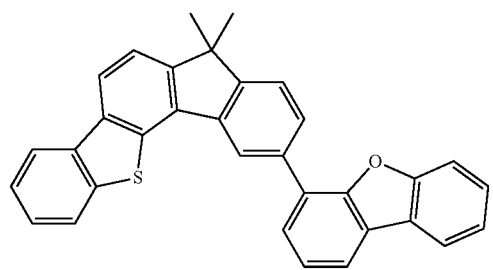
65
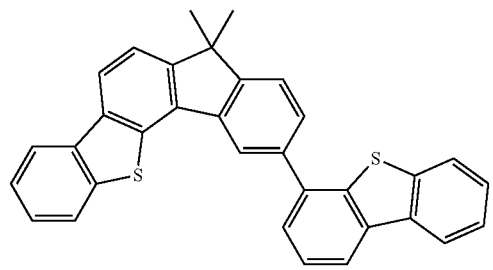
66
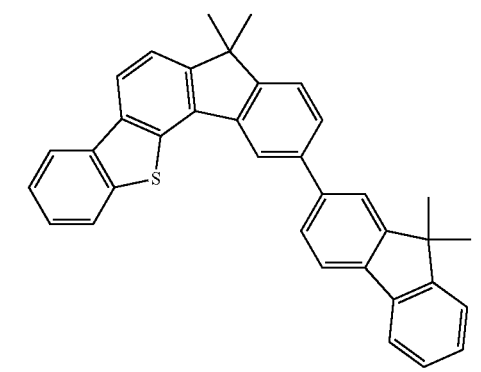
67
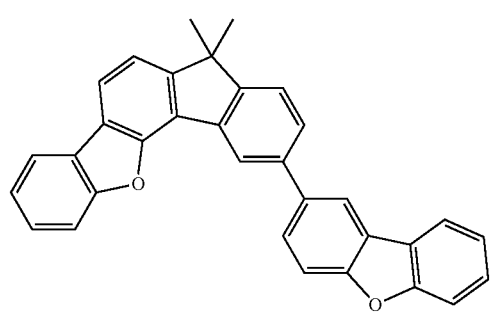
68
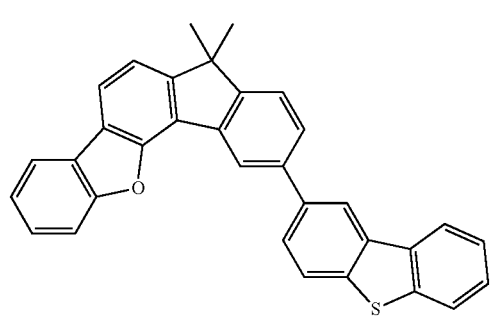

69
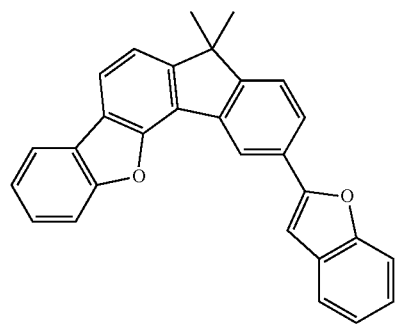
70
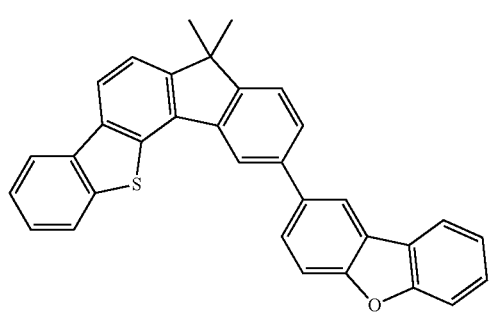
71
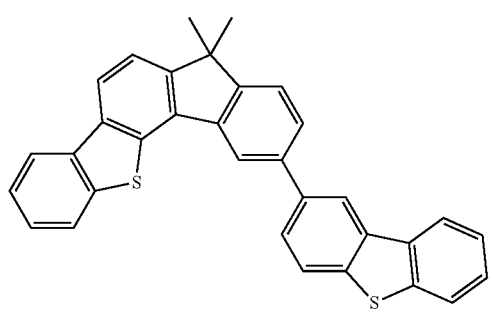
72
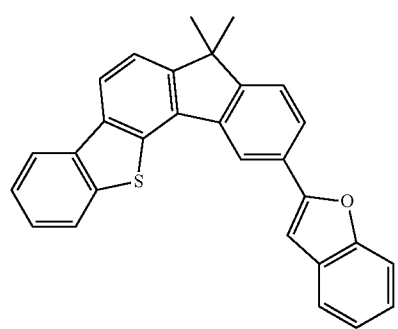
73
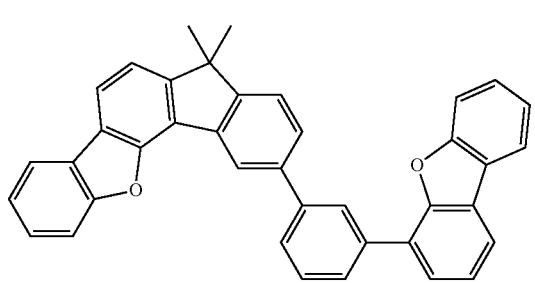
74
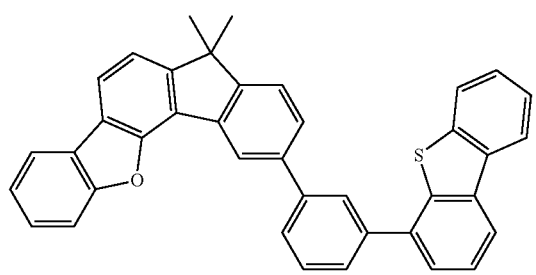
75
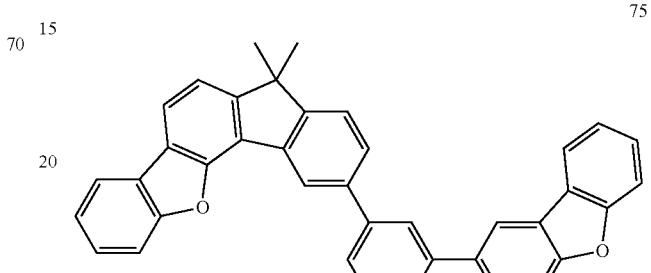
76
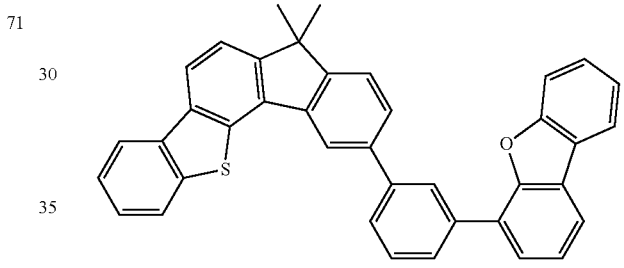
77
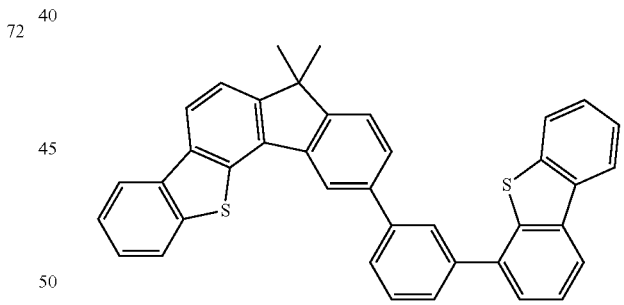
78
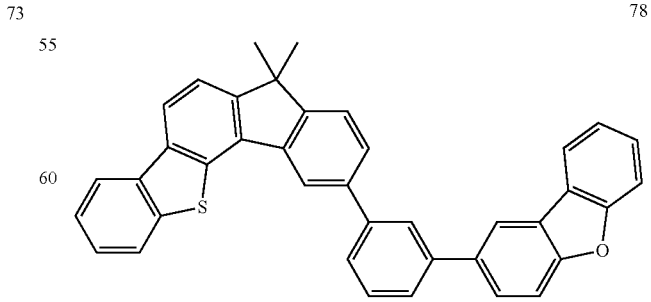

79
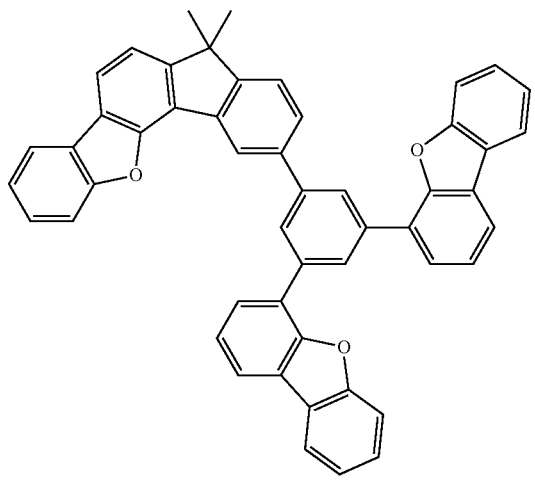
80
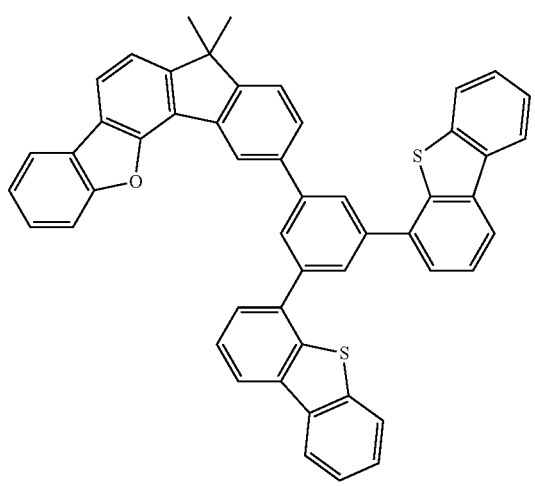
81
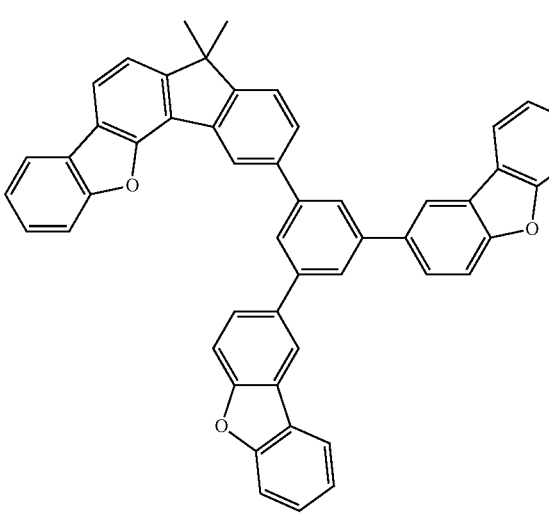
82
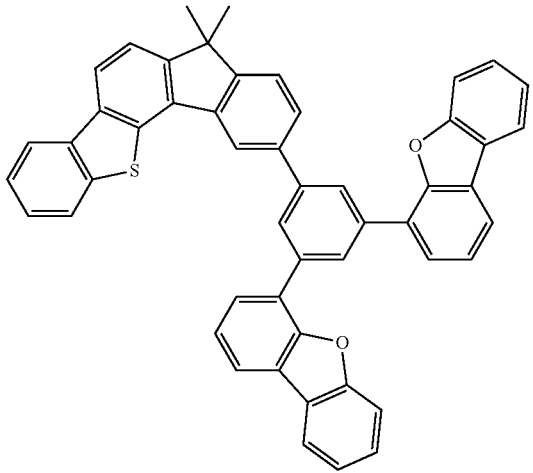
83
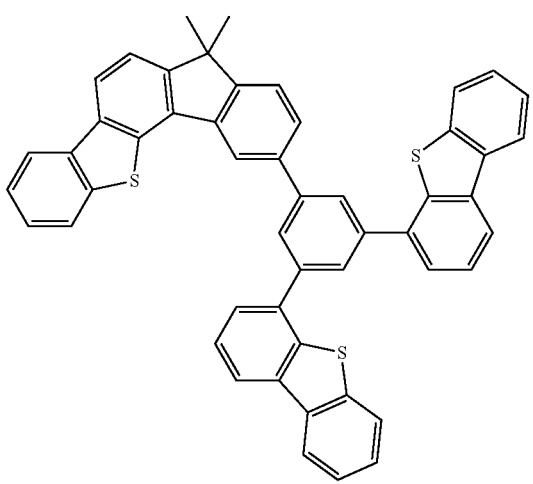
84
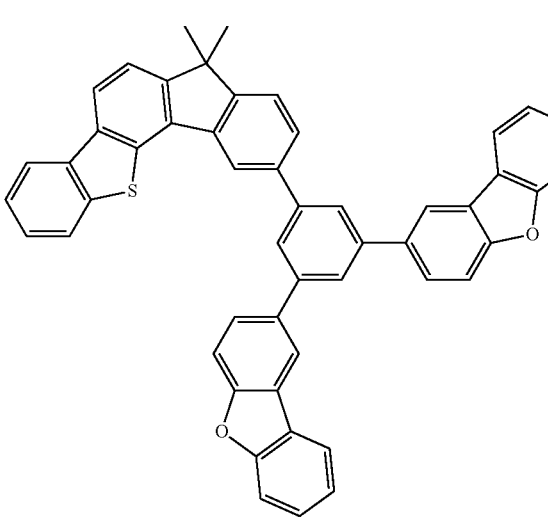

85 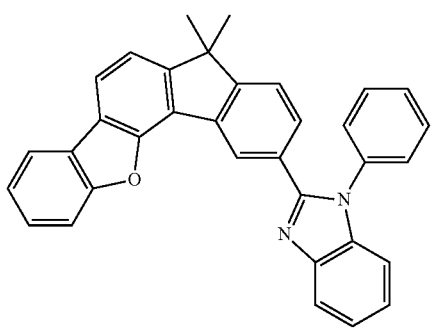

86 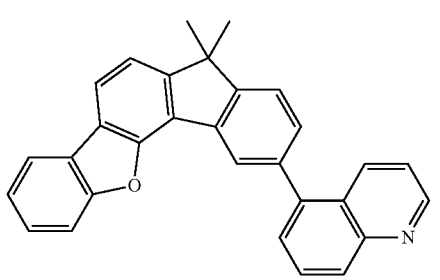

87 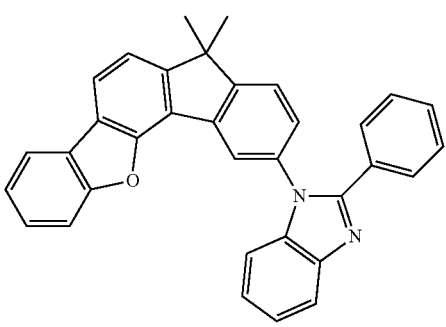

88 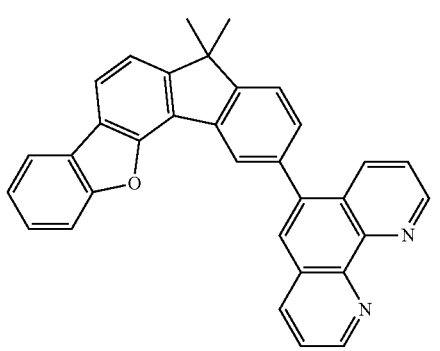

89 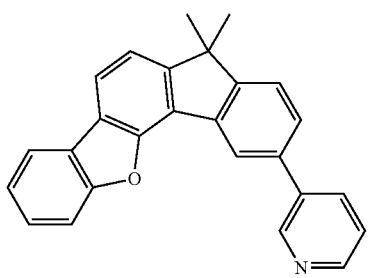

90 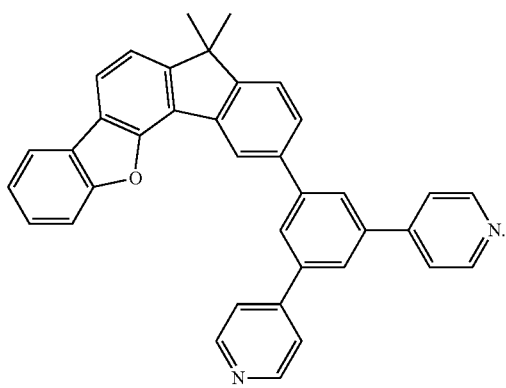

11. An organic optoelectric device comprising
an anode and a cathode facing each other,
at least one organic layer between the anode and the cathode,
wherein the organic layer comprises the organic compound as claimed in claim 1.

12. The organic optoelectric device as claimed in claim 11, wherein the organic layer comprises an emission layer, and
the emission layer comprises the organic compound.

13. The organic optoelectric device as claimed in claim 12, wherein
the organic compound is included in the emission layer as a host.

14. The organic optoelectric device as claimed in claim 11, wherein the organic layer comprises at least one auxiliary layer selected from a hole injection layer, a hole transport layer, an electron blocking layer, an electron transport layer, an electron injection layer, and a hole blocking layer, and
the auxiliary layer comprises the organic compound.

15. A display device comprising the organic optoelectric device as claimed in claim 11.

16. The organic compound as claimed in claim 1, wherein Y is a substituted or unsubstituted C3 to C30 heteroaryl group, a substituted or unsubstituted C6 to C30 heteroarylamine group, or a combination thereof.

17. An organic optoelectric device, comprising
an anode and a cathode facing each other,
at least one organic layer between the anode and the cathode,
wherein the organic layer includes one of the following Compounds 1 to 90:

1 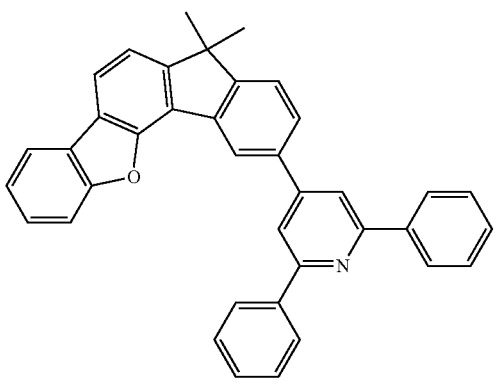

119
-continued
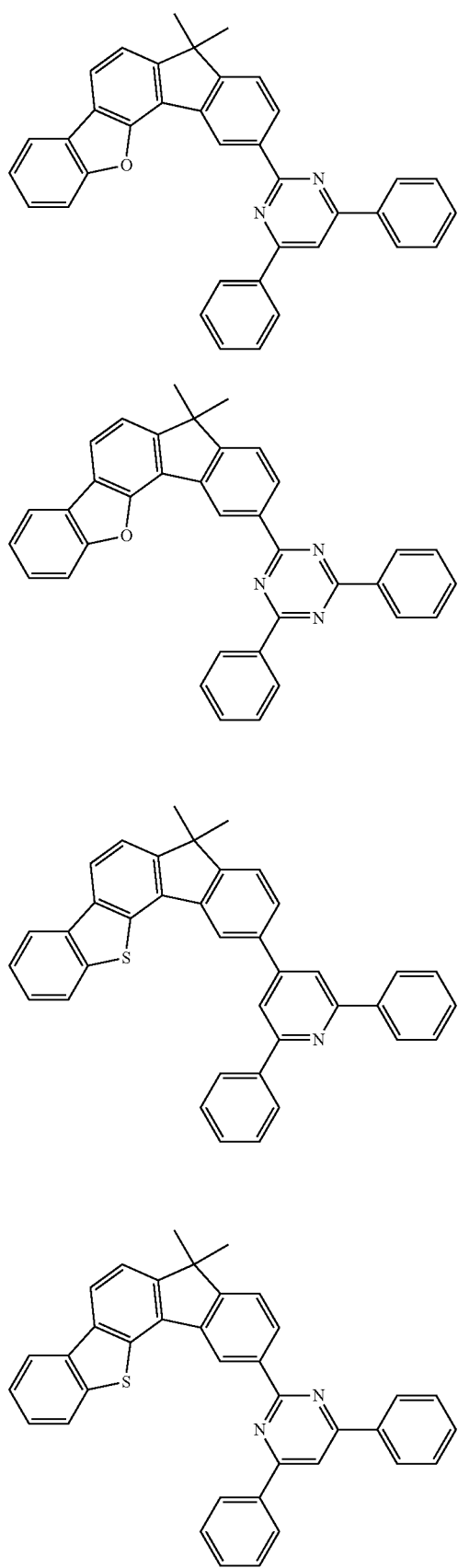
120
-continued
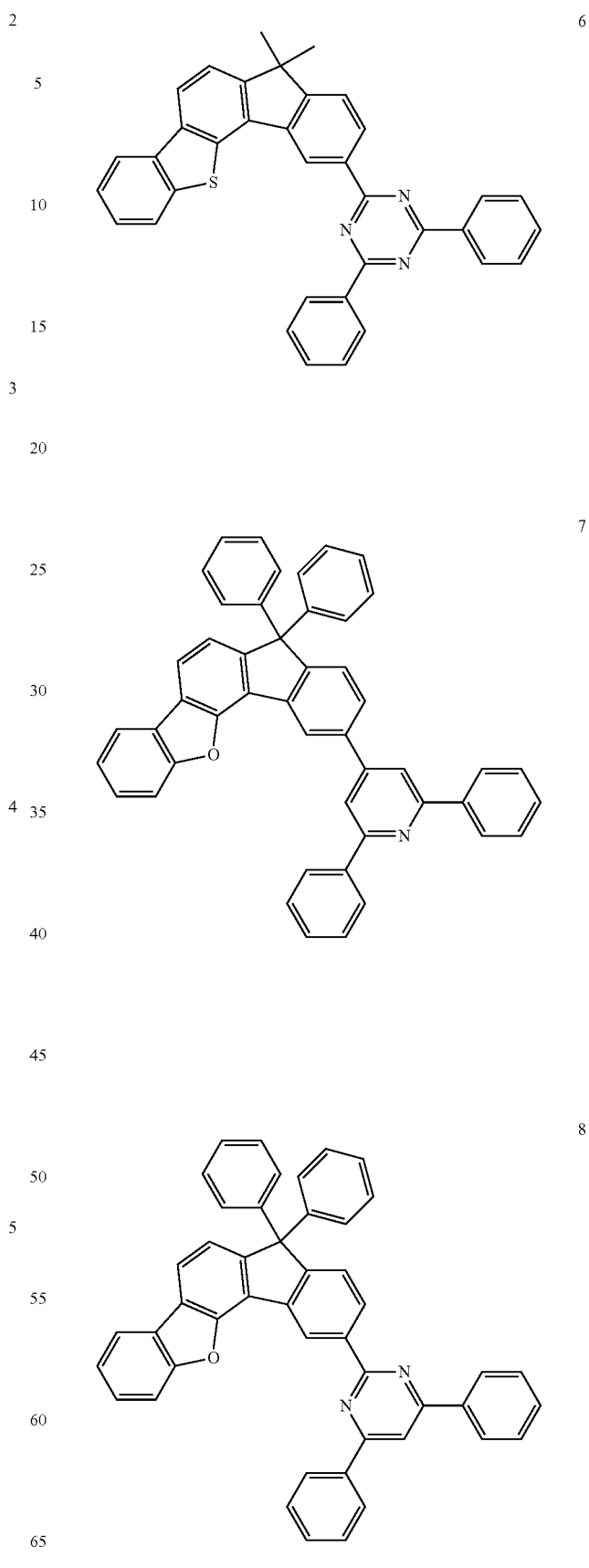

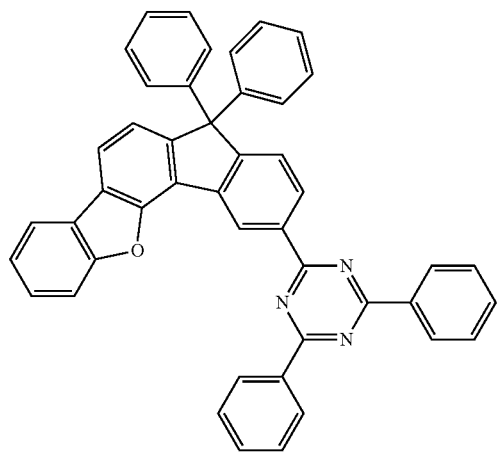
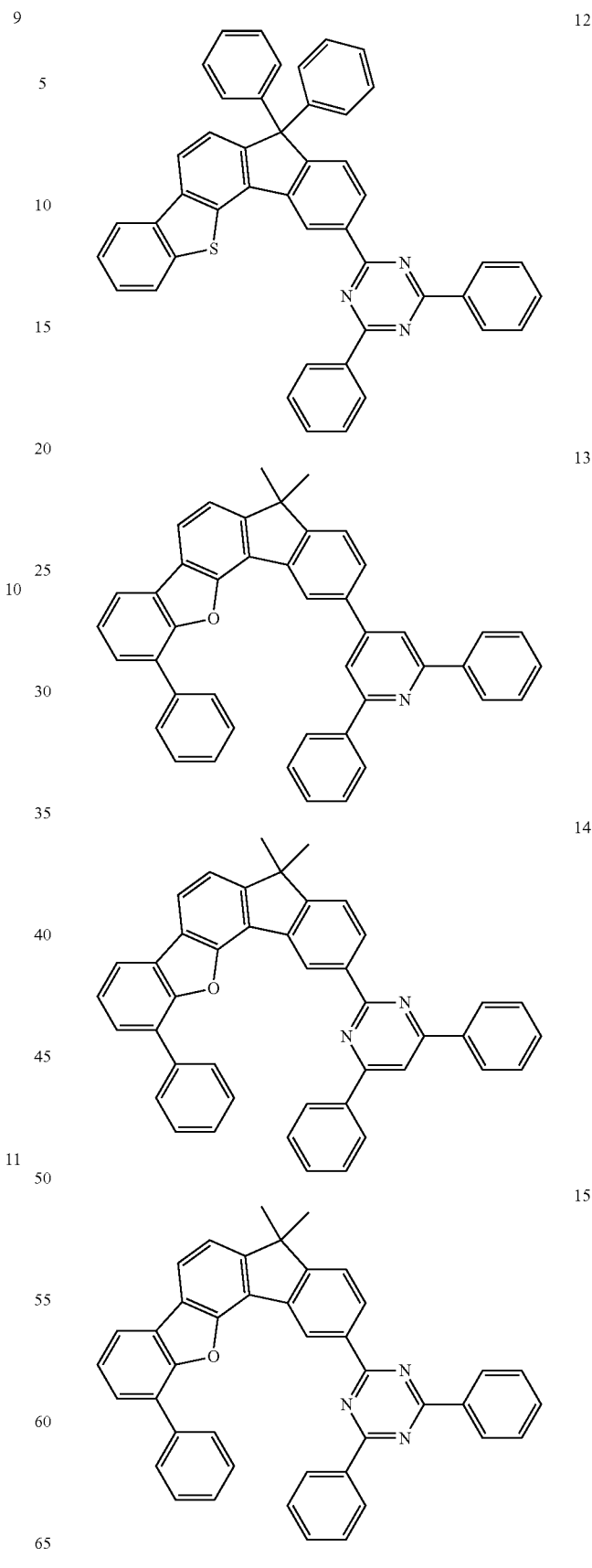

123
-continued
16
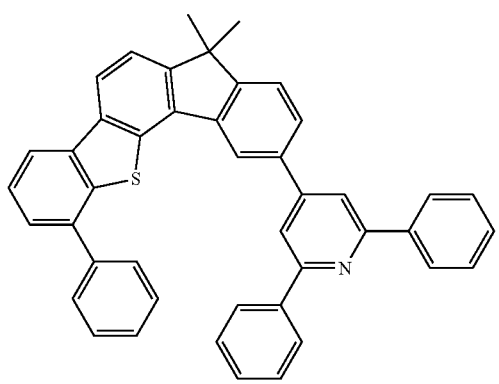
17
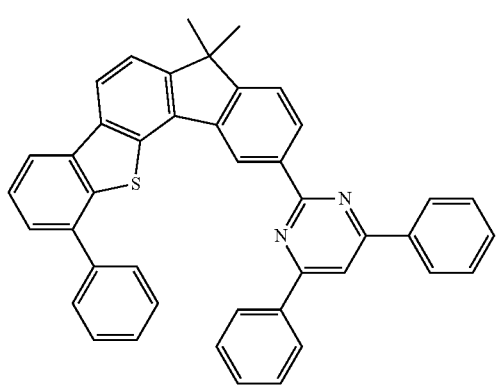
18
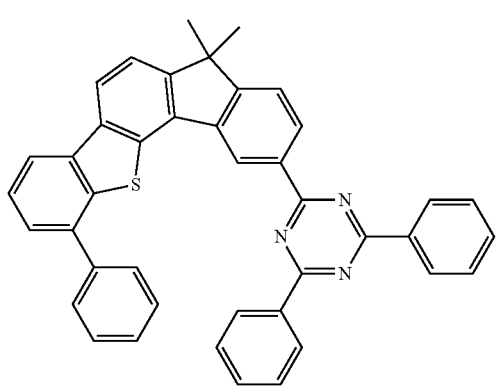
19
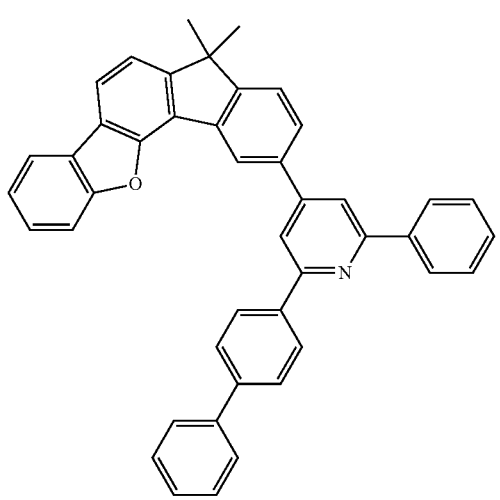
124
-continued
20
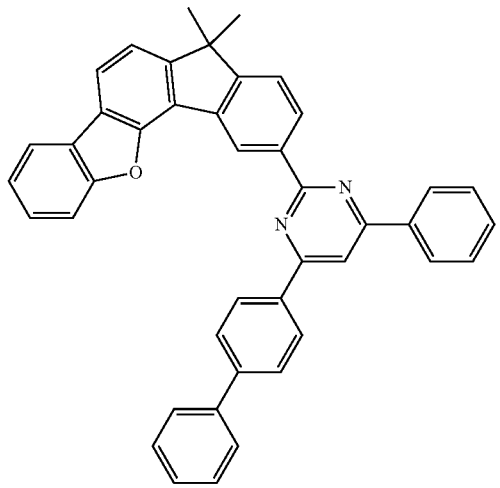
21
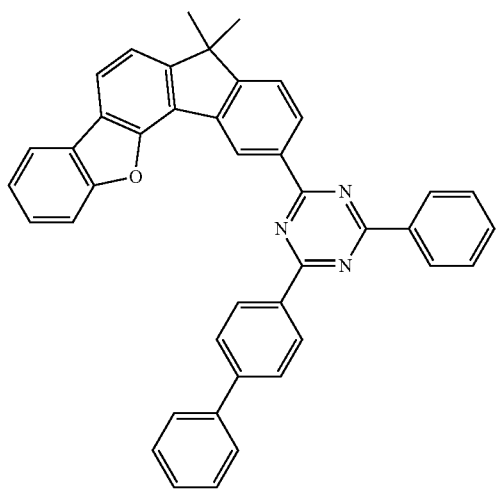
22
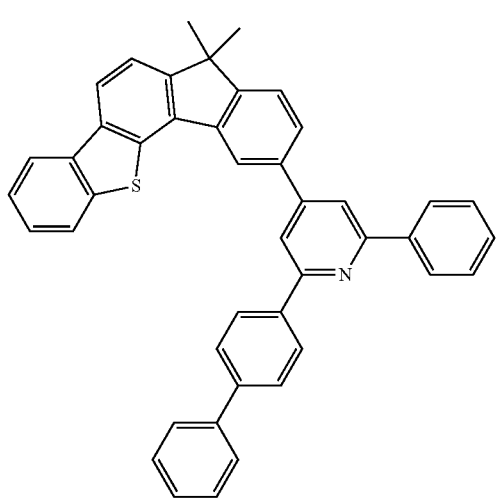

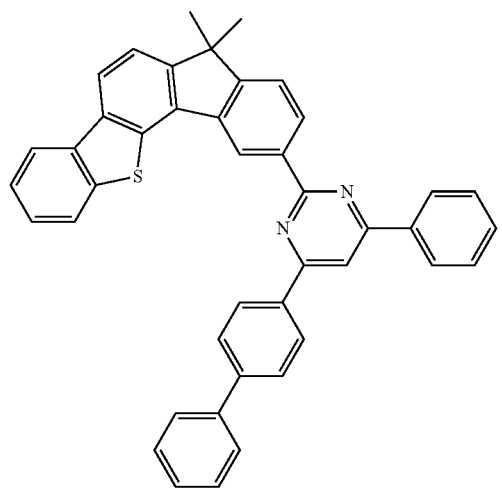
23
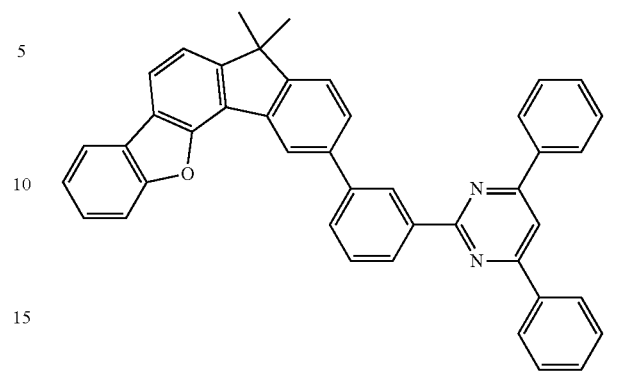
26
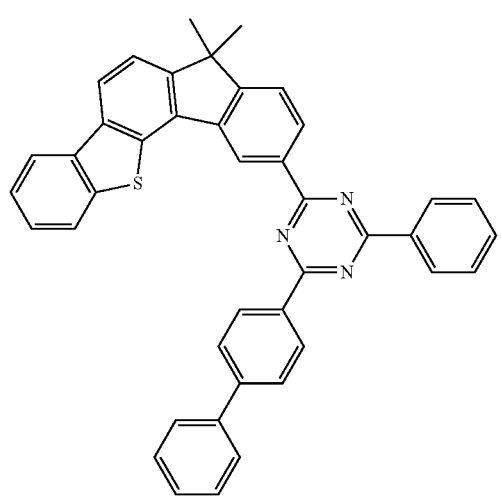
24
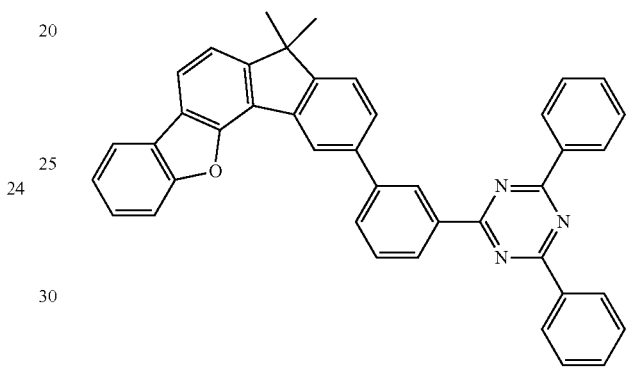
27
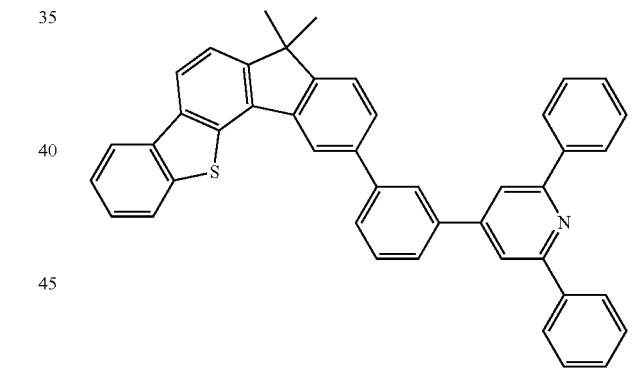
28
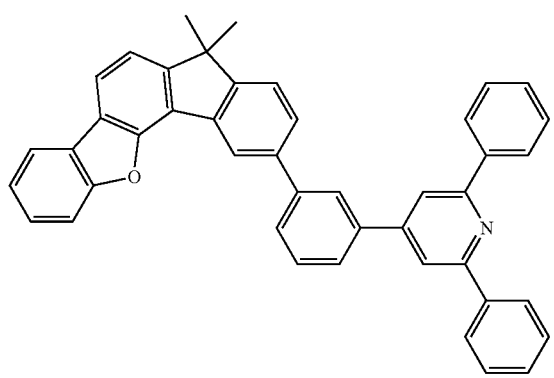
25
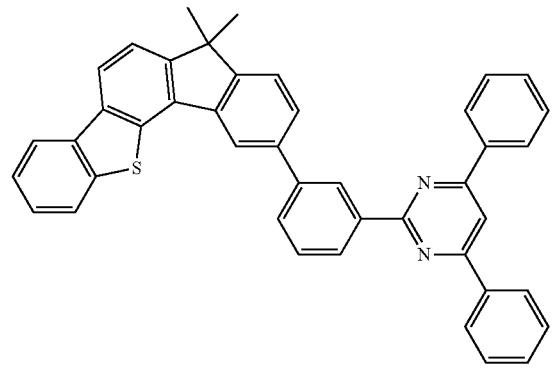
29

30
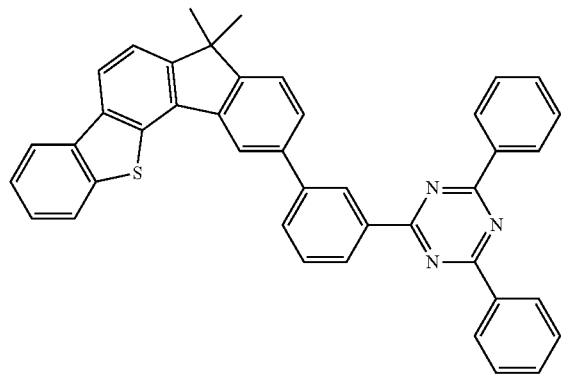
31
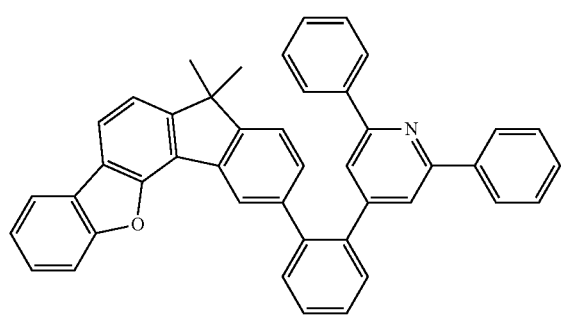
32
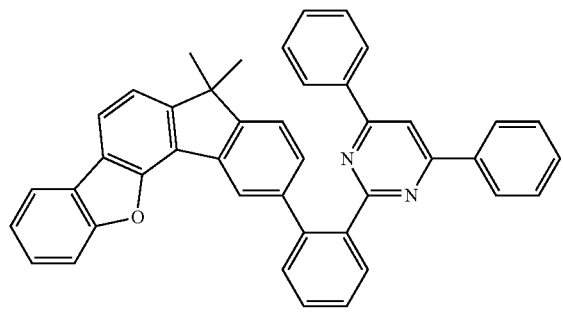
33
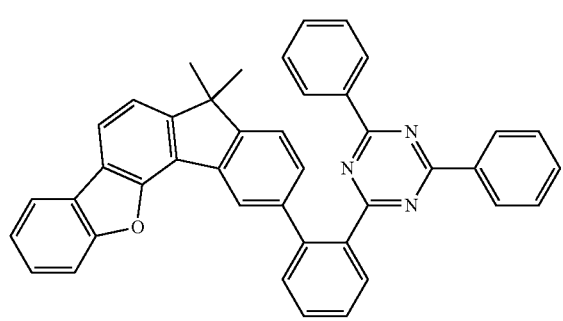
34
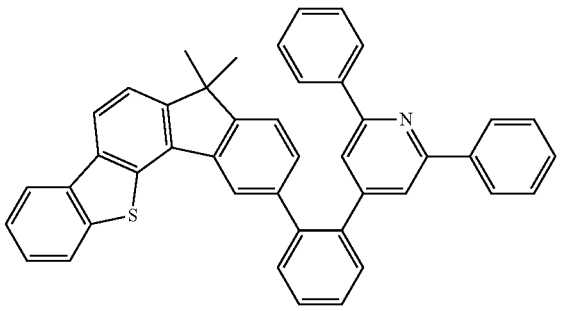
35
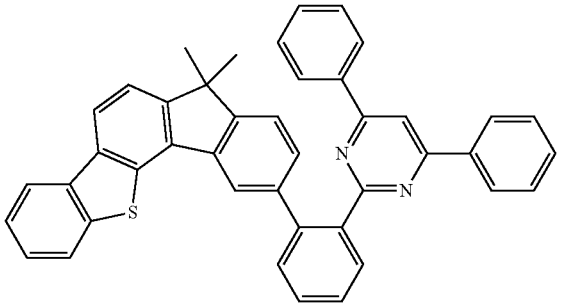
36
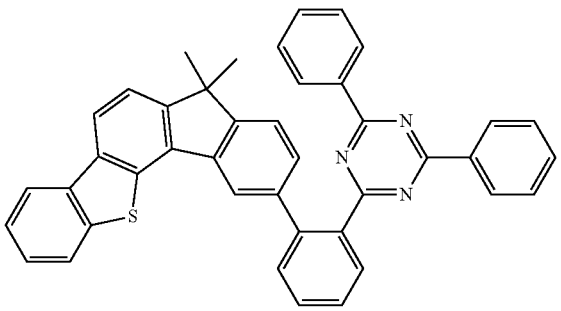
37
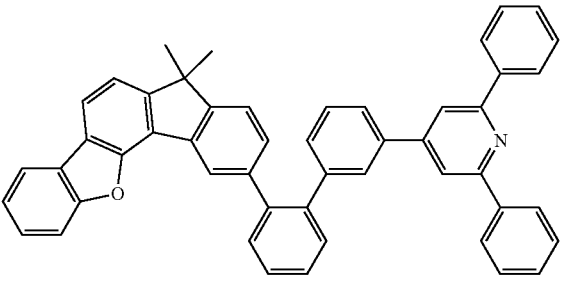
38
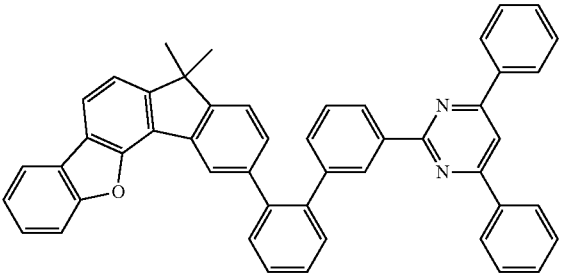

39
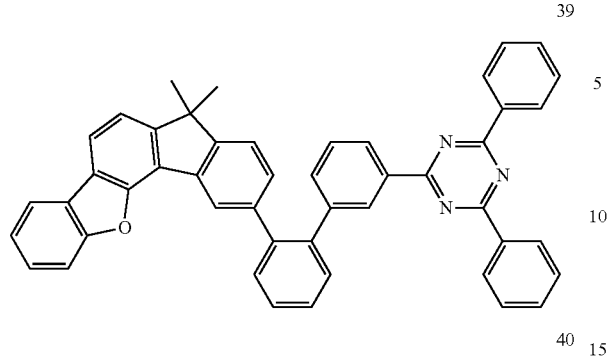
40
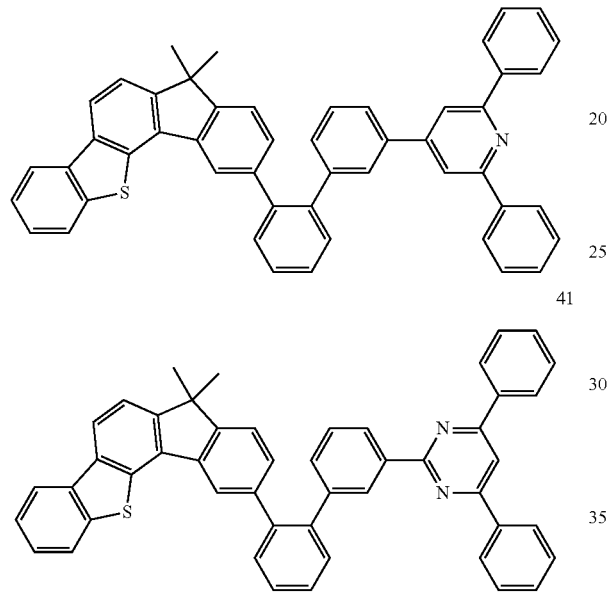
41
42
43
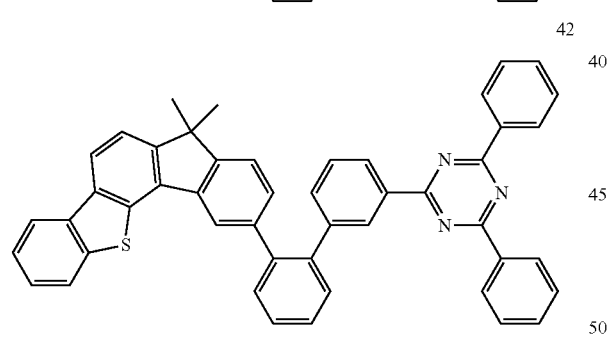
44
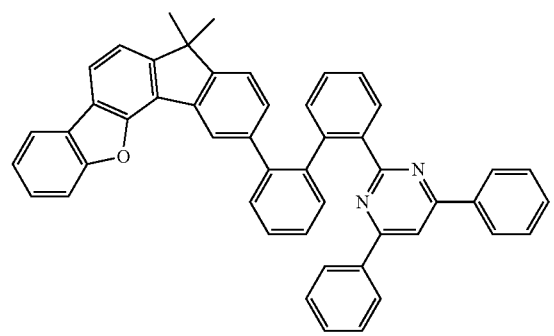
45
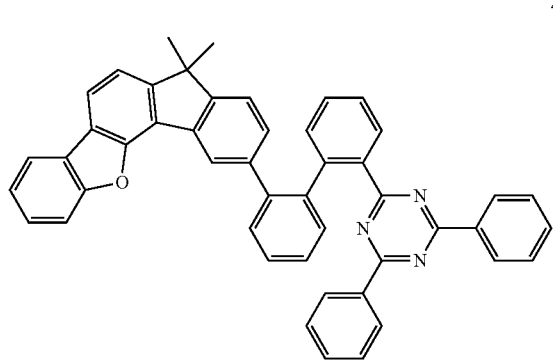
46
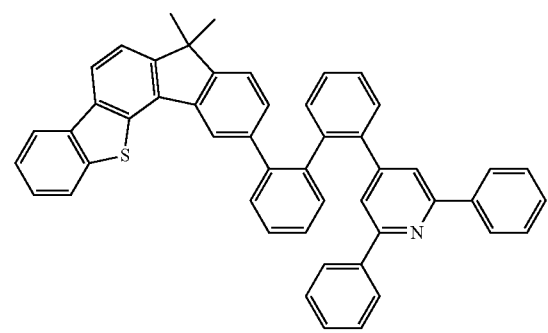
47
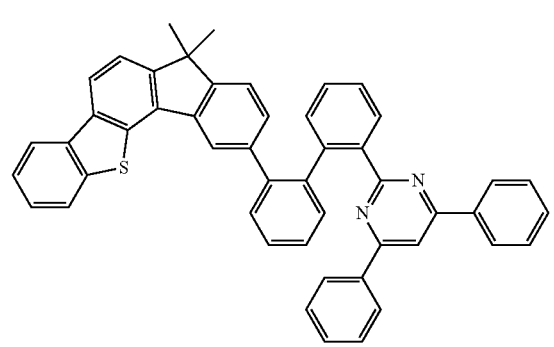

-continued
48
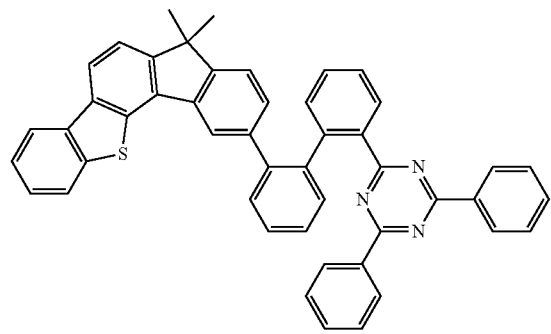
49
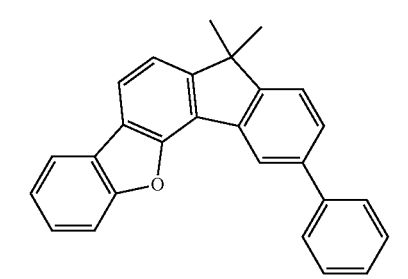
50
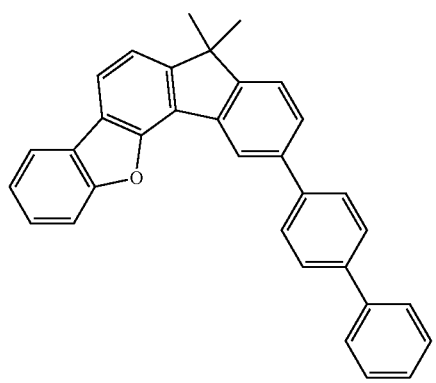
51
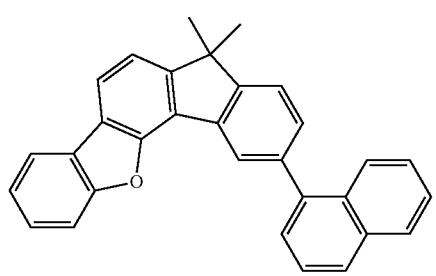
52
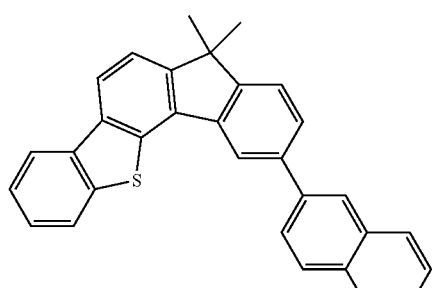
-continued
53
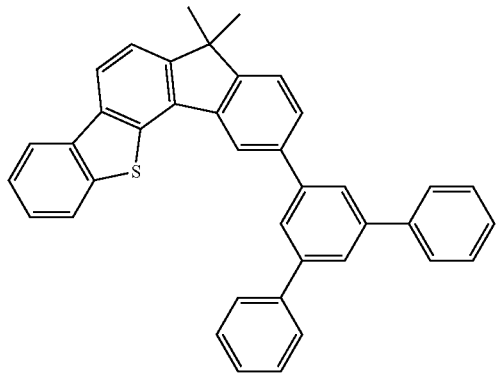
54
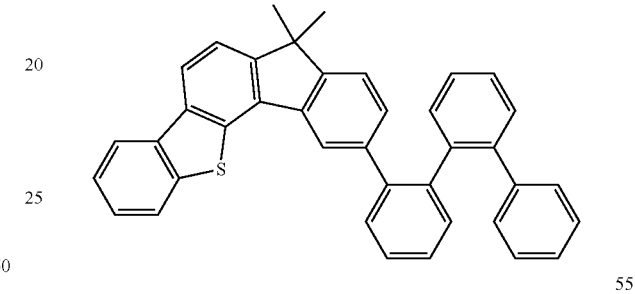
55
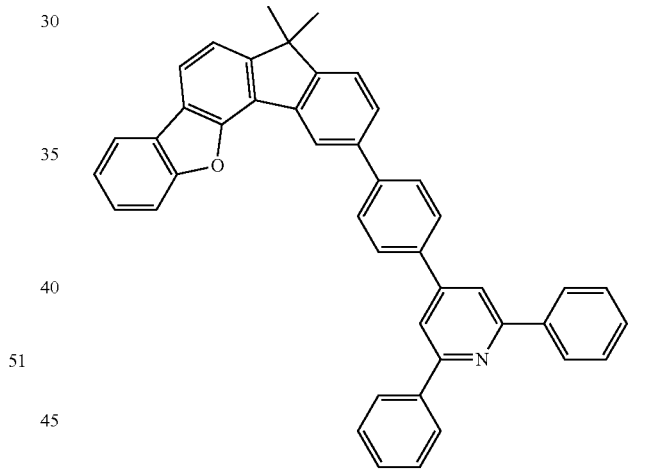
56
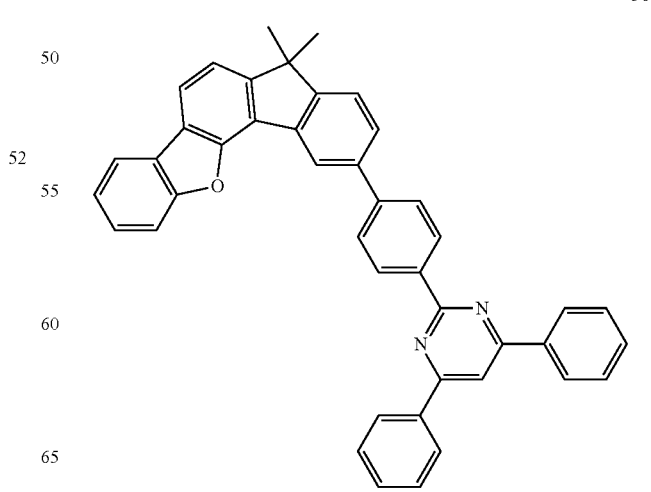

57
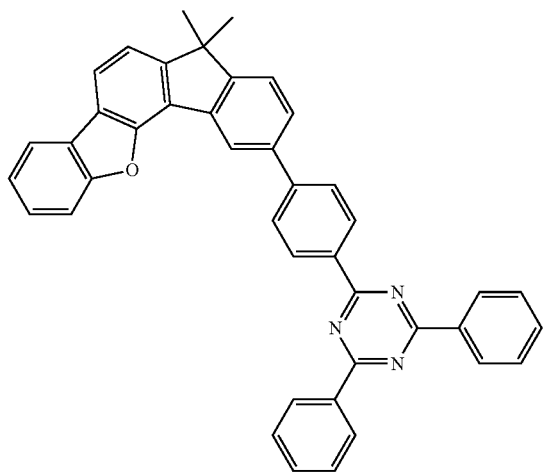
58
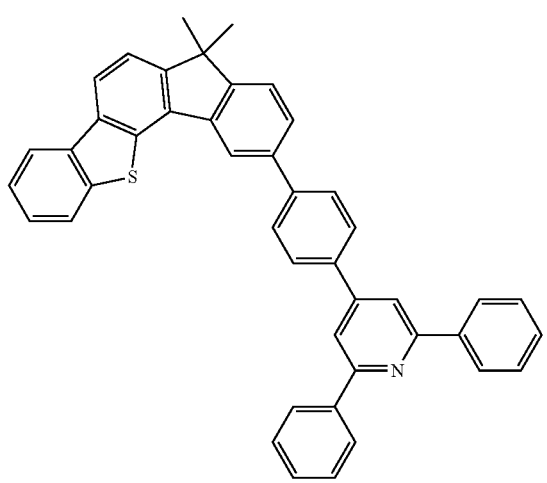
59
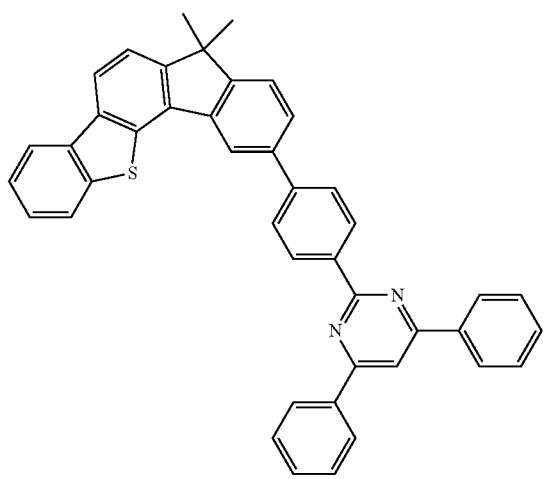
60
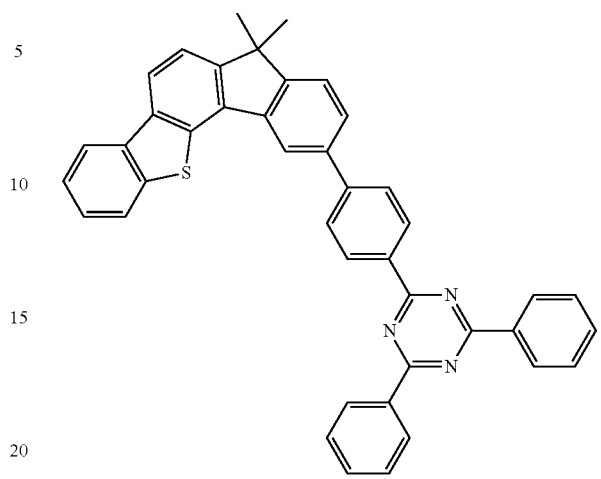
61
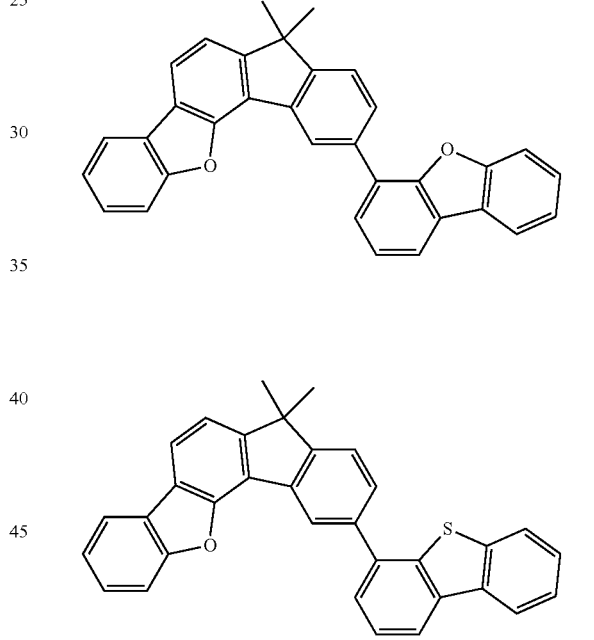
62
63
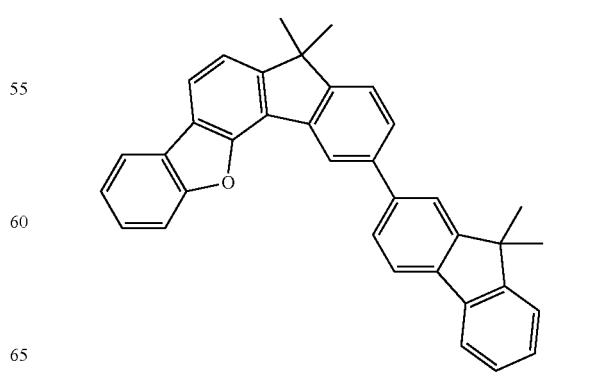

64
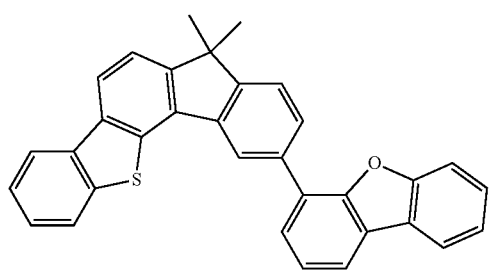
65
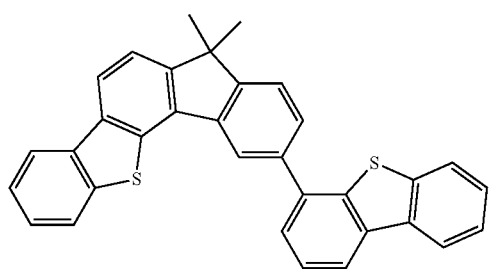
66
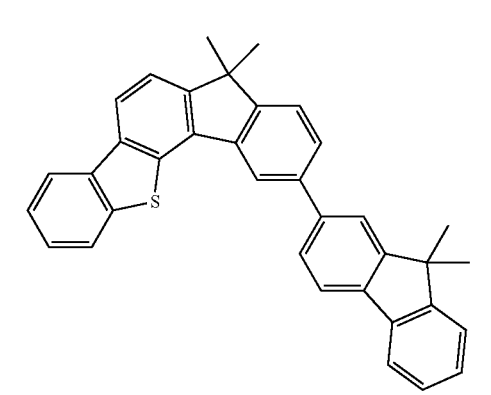
67
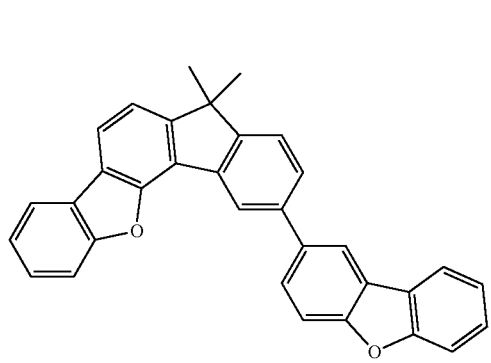
68
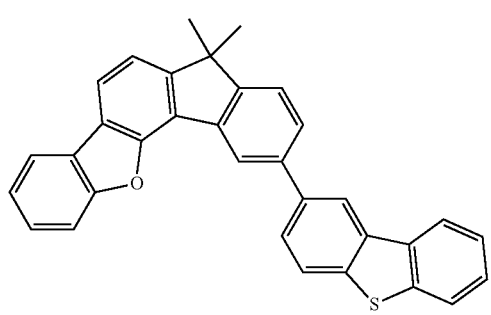
69
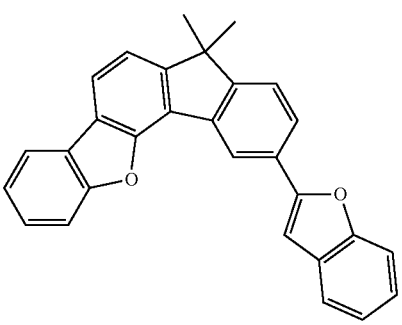
70
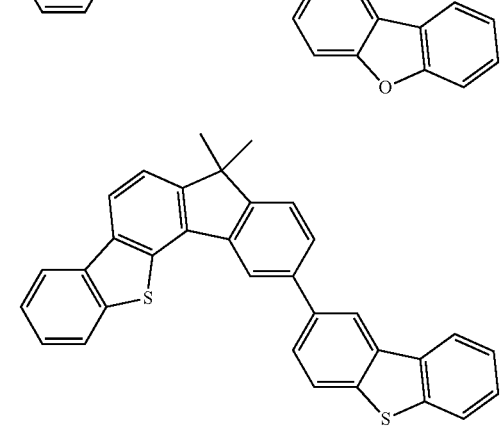
71
72
73
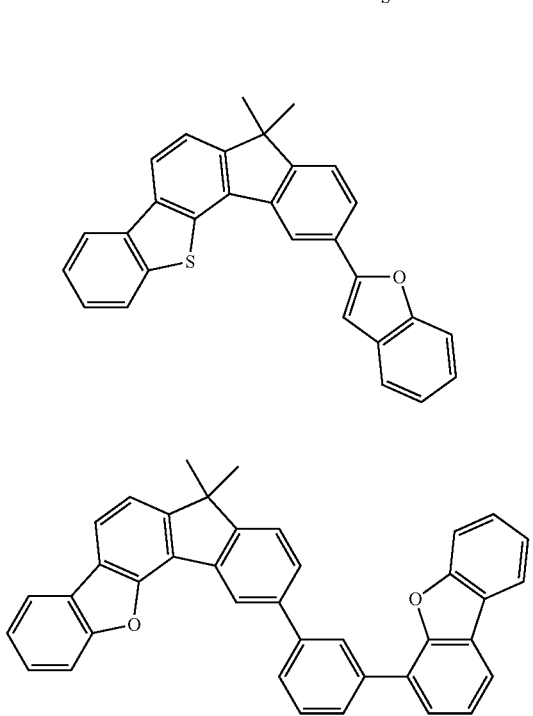

74
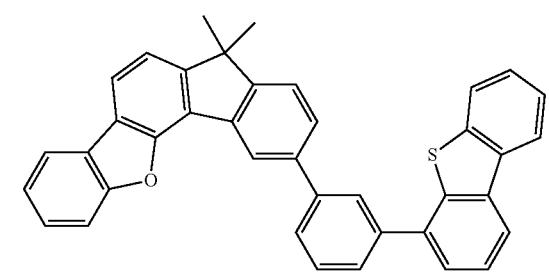
75
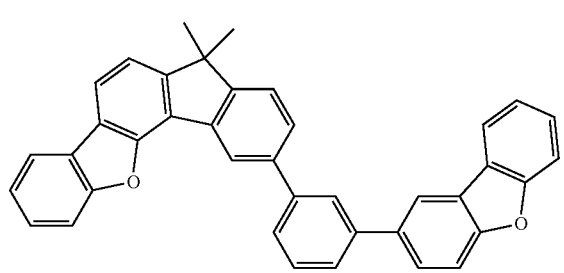
76
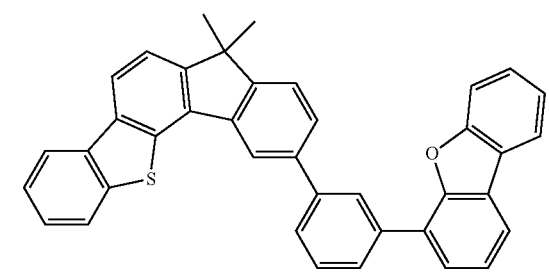
77
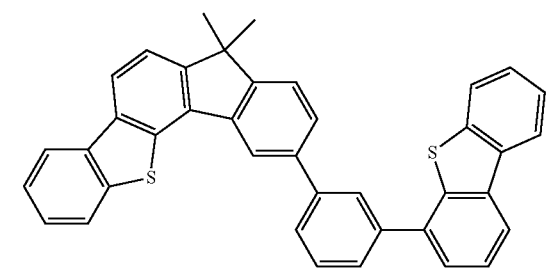
78
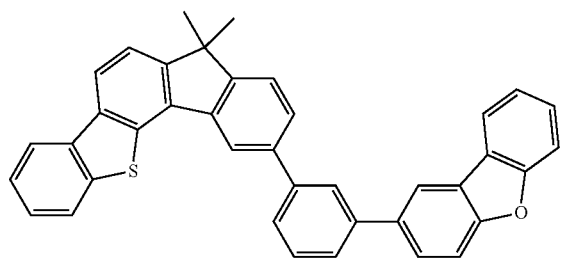
79
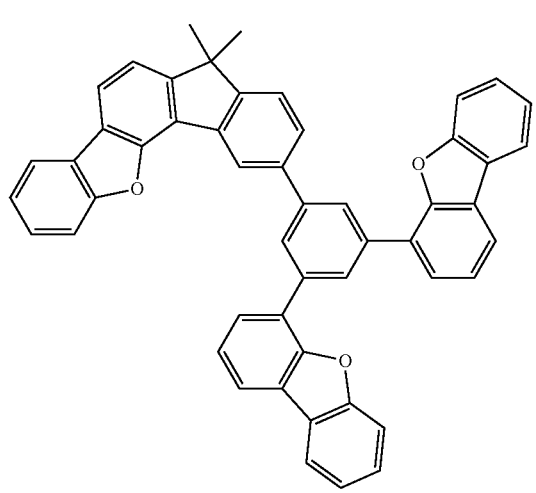
80
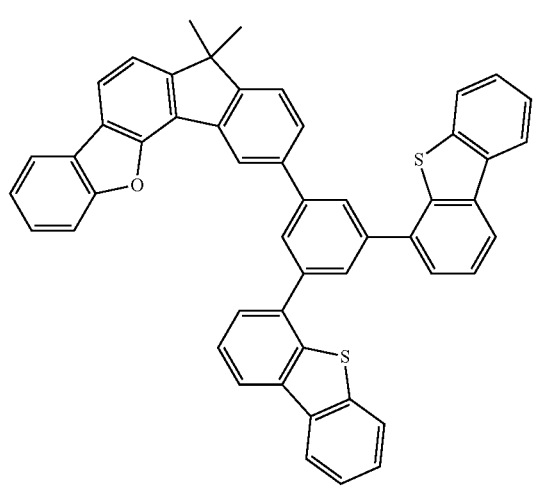
81
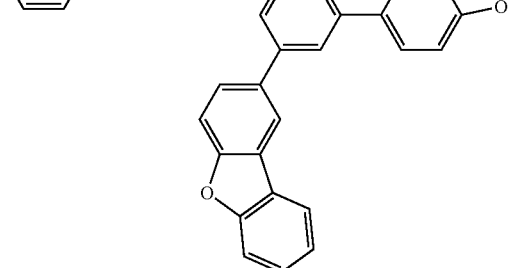

-continued
82
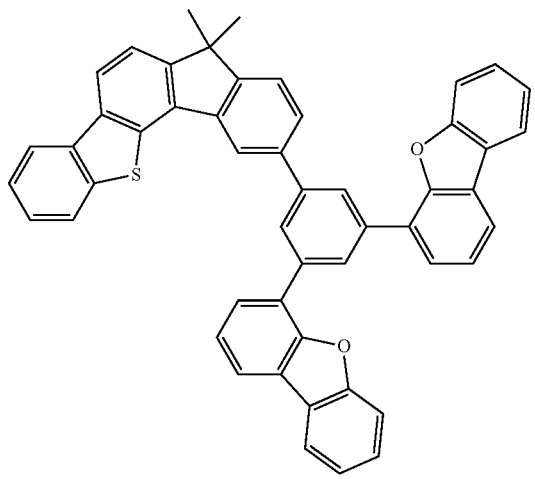
83
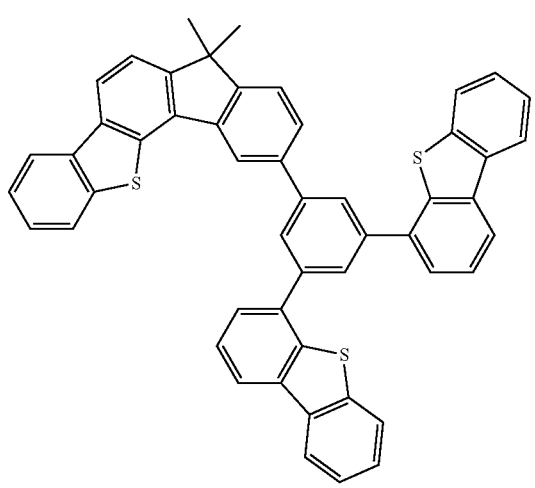
84
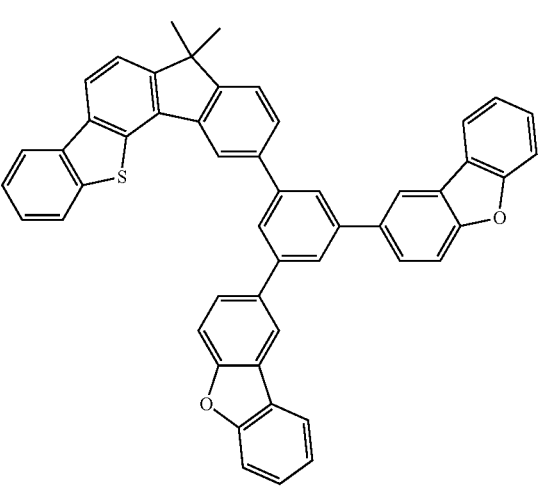
-continued
85
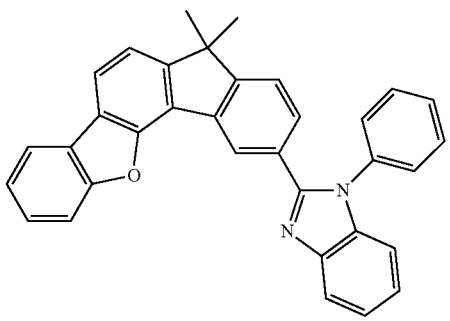
86
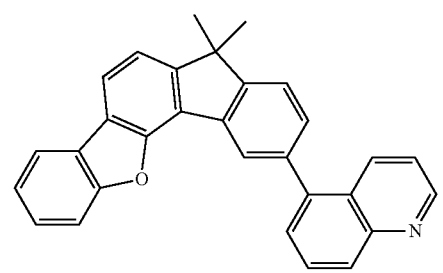
87
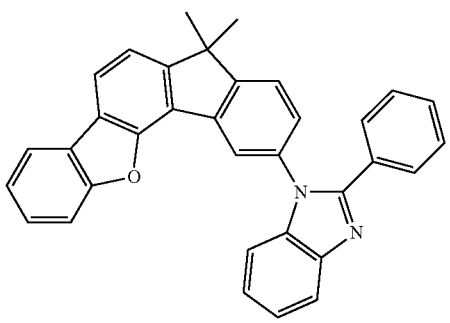
88
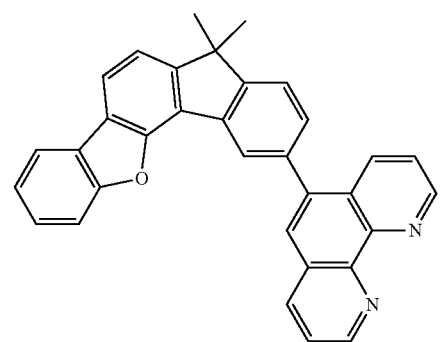
89
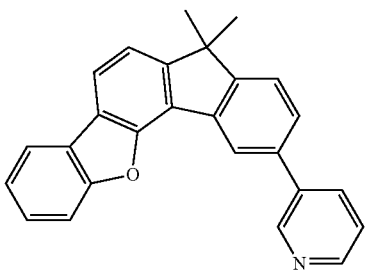

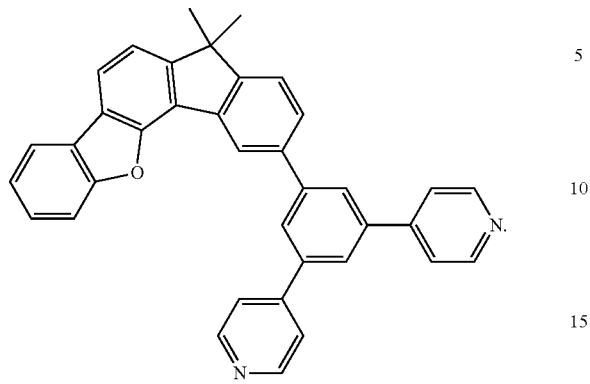
* * * * *